(12) United States Patent
Tan et al.

(10) Patent No.: US 9,889,449 B2
(45) Date of Patent: *Feb. 13, 2018

(54) INTEGRATED SYSTEMS FOR THE MULTIPLEXED AMPLIFICATION AND DETECTION OF SIX AND GREATER DYE LABELED FRAGMENTS

(71) Applicant: ANDE CORPORATION, Waltham, MA (US)

(72) Inventors: Eugene Tan, Arlington, MA (US); Heung Chuan Lam, Newton, MA (US); Valery Leonidovich Bogdanov, Woburn, MA (US); Gregory John Kellogg, Cambridge, MA (US); John A. Wright, Billerica, MA (US); Ulrich Hans Thomann, Stow, MA (US); Richard F. Selden, Lincoln, MA (US)

(73) Assignee: ANDE Corporation, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/151,147

(22) Filed: May 10, 2016

(65) Prior Publication Data

US 2017/0100718 A1 Apr. 13, 2017

Related U.S. Application Data

(63) Continuation of application No. 13/191,952, filed on Jul. 27, 2011, now Pat. No. 9,366,631, which is a
(Continued)

(51) Int. Cl.
*B01L 7/00* (2006.01)
*B01L 3/00* (2006.01)
(Continued)

(52) U.S. Cl.
CPC ............ *B01L 7/52* (2013.01); *B01L 3/502753* (2013.01); *G01N 21/6428* (2013.01);
(Continued)

(58) Field of Classification Search
CPC ............ G01N 21/6486; G01N 21/6452; G01N 27/44726; G01N 27/44782;
(Continued)

(56) References Cited

U.S. PATENT DOCUMENTS

| 4,832,815 A | 5/1989 | Kambara et al. |
| 4,855,225 A | 8/1989 | Fung et al. |

(Continued)

FOREIGN PATENT DOCUMENTS

| JP | 2000508539 | 7/2000 |
| JP | 2002530121 | 9/2002 |

(Continued)

OTHER PUBLICATIONS

Karlinsey, J.M., et al., "Pressure Injection on a Valved Microdevice for Electrophoretic Analysis of Submicroliter Samples," Analytical Chemistry, vol. 77, No. 11, Jun. 1, 2005, pp. 3637-3643.
(Continued)

*Primary Examiner* — Michael P Lapage
(74) *Attorney, Agent, or Firm* — Proskauer Rose LLP

(57) ABSTRACT

The present disclosure provides fully integrated microfluidic systems to perform nucleic acid analysis. These processes include sample collection, nucleic acid extraction and purification, amplification, sequencing, and separation and detection. The present disclosure also provides optical detection systems and methods for separation and detection of biological molecules. In particular, the various aspects of the invention enable the simultaneous separation and detection of a plurality of biological molecules, typically fluorescent dye-labeled nucleic acids, within one or a plurality
(Continued)

of microfluidic chambers or channels. The nucleic acids can be labeled with at least 6 dyes, each having a unique peak emission wavelength. The present systems and methods are particularly useful for DNA fragment sizing applications such as human identification by genetic fingerprinting and DNA sequencing applications such as clinical diagnostics.

13 Claims, 64 Drawing Sheets

Related U.S. Application Data continuation of application No. 12/080,751, filed on Apr. 4, 2008, now Pat. No. 8,018,593.

(60) Provisional application No. 61/028,073, filed on Feb. 12, 2008, provisional application No. 60/964,502, filed on Aug. 13, 2007, provisional application No. 60/921,802, filed on Apr. 4, 2007.

(51) Int. Cl.
G01N 21/64 (2006.01)
G01N 27/447 (2006.01)

(52) U.S. Cl.
CPC ..... *G01N 21/6452* (2013.01); *G01N 21/6486* (2013.01); *G01N 27/44726* (2013.01); *G01N 27/44782* (2013.01); *G01N 27/44791* (2013.01); *B01L 2200/0684* (2013.01); *B01L 2200/10* (2013.01); *B01L 2300/069* (2013.01); *B01L 2300/0816* (2013.01); *B01L 2300/0887* (2013.01); *B01L 2400/0421* (2013.01)

(58) Field of Classification Search
CPC .......... G01N 27/44791; G01N 21/6428; B01L 3/502753; B01L 2200/0684; B01L 2200/10; B01L 2300/069; B01L 2300/0816; B01L 2300/0887; B01L 2400/0421; Y10T 436/2575
See application file for complete search history.

(56) References Cited

U.S. PATENT DOCUMENTS

| | | |
|---|---|---|
| 4,865,707 A | 9/1989 | Karger |
| 4,881,812 A | 11/1989 | Ohkubo et al. |
| 4,945,135 A | 7/1990 | Grubbs |
| 5,112,460 A | 5/1992 | Karger |
| 5,198,511 A | 3/1993 | Brown-Wensley |
| 5,234,809 A | 8/1993 | Boom et al. |
| 5,273,638 A | 12/1993 | Konrad et al. |
| 5,307,148 A | 4/1994 | Kambara et al. |
| 5,312,940 A | 5/1994 | Grubbs |
| 5,332,666 A | 7/1994 | Prober et al. |
| 5,334,424 A | 8/1994 | Hani |
| 5,342,909 A | 8/1994 | Grubbs |
| 5,436,130 A * | 7/1995 | Mathies ............... C12Q 1/6869 435/6.12 |
| 5,462,995 A | 10/1995 | Hosaka |
| 5,561,208 A | 10/1996 | Takahashi |
| 5,663,129 A | 9/1997 | Emert |
| 5,800,996 A | 9/1998 | Lee et al. |
| 5,840,338 A | 11/1998 | Roos |
| 5,847,162 A | 12/1998 | Lee et al. |
| 5,876,675 A | 3/1999 | Kennedy |
| 5,976,336 A | 11/1999 | Dubrow |
| 5,981,956 A | 11/1999 | Stern |
| 6,017,434 A | 1/2000 | Simpson et al. |
| 6,017,765 A | 1/2000 | Yamada et al. |
| 6,100,541 A | 8/2000 | Nagle |
| 6,150,180 A | 11/2000 | Parce |
| 6,156,181 A | 12/2000 | Parce |
| 6,167,910 B1 | 1/2001 | Chow |
| 6,211,955 B1 | 4/2001 | Basiji et al. |
| 6,224,732 B1 | 5/2001 | Imasaka et al. |
| 6,225,636 B1 | 5/2001 | Ginestet |
| 6,316,781 B1 | 11/2001 | Nagle |
| 6,321,791 B1 | 11/2001 | Chow |
| 6,329,661 B1 | 12/2001 | Perov |
| 6,358,387 B1 | 3/2002 | Kopf-Sill |
| 6,361,672 B1 | 3/2002 | Zhu et al. |
| 6,391,541 B1 | 5/2002 | Petersen et al. |
| 6,407,395 B1 | 6/2002 | Perov |
| 6,409,900 B1 | 6/2002 | Parce |
| 6,413,782 B1 | 7/2002 | Parce |
| 6,431,476 B1 | 8/2002 | Taylor et al. |
| 6,444,461 B1 | 9/2002 | Knapp et al. |
| 6,471,916 B1 | 10/2002 | Noblett |
| 6,479,299 B1 | 11/2002 | Parce |
| 6,485,625 B1 | 11/2002 | Simpson et al. |
| 6,494,230 B2 | 12/2002 | Chow |
| 6,498,353 B2 | 12/2002 | Nagle |
| 6,531,044 B1 | 3/2003 | Anazawa et al. |
| 6,602,472 B1 | 8/2003 | Zimmermann |
| 6,630,063 B1 | 10/2003 | Li et al. |
| 6,630,680 B2 | 10/2003 | Hakamata et al. |
| 6,635,487 B1 | 10/2003 | Lee |
| 6,646,271 B2 | 11/2003 | Yokokawa |
| 6,648,015 B1 | 11/2003 | Chow |
| 6,664,057 B2 | 12/2003 | Albertson |
| 6,764,512 B2 | 7/2004 | Keller |
| 6,787,016 B2 | 9/2004 | Tan |
| 6,857,449 B1 | 2/2005 | Chow |
| 6,916,614 B1 | 7/2005 | Takenaka |
| 6,929,730 B2 | 8/2005 | Lee |
| 6,952,008 B2 | 10/2005 | Corson |
| 6,987,018 B2 | 1/2006 | Taylor et al. |
| 6,995,841 B2 | 2/2006 | Scott et al. |
| 7,029,562 B2 | 4/2006 | Anazawa et al. |
| 7,033,474 B1 | 4/2006 | Dubrow |
| 7,038,775 B2 | 5/2006 | Sakai |
| 7,069,952 B1 | 7/2006 | McReynolds |
| 7,261,859 B2 | 8/2007 | Andersson et al. |
| 7,280,204 B2 | 10/2007 | Robinson et al. |
| 7,300,199 B2 | 11/2007 | Andersson et al. |
| 7,332,126 B2 | 2/2008 | Tooke et al. |
| 2002/0046949 A1 | 4/2002 | Nakamura et al. |
| 2002/0146734 A1 | 10/2002 | Ortyn |
| 2002/0155485 A1 | 10/2002 | Kao Pin |
| 2003/0007898 A1 | 1/2003 | Bohm |
| 2003/0020022 A1 | 1/2003 | Kuwabata et al. |
| 2003/0058440 A1 | 3/2003 | Scott et al. |
| 2003/0082080 A1 | 5/2003 | Zimmermann |
| 2003/0098239 A1 | 5/2003 | Anazawa et al. |
| 2003/0134431 A1 | 7/2003 | Parce |
| 2003/0146145 A1 | 8/2003 | Krotz et al. |
| 2004/0150217 A1 | 8/2004 | Heffelfinger et al. |
| 2004/0197816 A1 | 10/2004 | Empedocles et al. |
| 2005/0179901 A1 | 8/2005 | Ostlin |
| 2006/0257958 A1 | 11/2006 | Bruno |
| 2006/0260941 A1 | 11/2006 | Tan et al. |
| 2006/0286552 A1 | 12/2006 | Goldsmith |
| 2007/0206187 A1 | 9/2007 | Lundquist et al. |
| 2012/0315635 A1* | 12/2012 | Vangbo ............ G01N 27/44791 435/6.11 |

FOREIGN PATENT DOCUMENTS

| | | |
|---|---|---|
| WO | 0141931 | 6/2001 |
| WO | 0224322 | 3/2002 |
| WO | 2005073691 | 8/2005 |
| WO | 2006124842 | 11/2006 |
| WO | 2007021814 | 2/2007 |
| WO | 02097398 | 12/2008 |

OTHER PUBLICATIONS

Koh, C.G., et al., "Integrating Polymerase Chain Reaction, Valving, and Electrophoresis in a Plastic Device for Bacterial Detection," Analytical Chemistry, vol. 75, No. 17, Sep. 1, 2003, pp. 4591-4598.

(56) References Cited

OTHER PUBLICATIONS

Maxam and Gilbert, A new method for sequencing DNA, 1977, Proc Natl Acad Sci USA 74,560-564.
Sanger et al., DNA sequencing with chain-terminating inhibitors, 1977, Proc Nat! Acad Sci USA 74,5463-5467.
Auroux et al., Micro Total Analysis Systems. 2. Analytical Standard Operations and Applications. 2002, Anal Chem., 74, 2637-2652.
Metzker, Emerging technologies in DNA sequencing, 2005, Genome Research 15: 1767-1776.
Edwards et al., DNA typing and genetic mapping with trimeric and tetrameric tandem repeats, 1991, Am J Hum Genet, 49(4): 746-756.
Ditirich et al., Micro Total Analysis Systems. Latest Advancements and Trends, 2006, Anal Chem. 78, 3887- 3907.
McCormick, et al., Microchannel Electrophoretic Separations of DNA in Injection-Molded Plastic Substrates, 1997, Anal Chem 69(14): 2626-2630.
Sassi, et al., Rapid, parallel separations of D1S80 all~les in a plastic microchannel chip, 2000, J Chromatogr A, 894 (1-2): 203-213.
Shi and Anderson, High-resolution single-stranded DNA analysis on 4.5 cm plastic electrophoretic microchannels, 2003, Electrophoresis 24( 19-20): 3371-3377.
Shi, DNA sequencing and multiplex STR analysis on plastic microfluidic devices, 2006, Electrophoresis 27(10):3703-3711.
Pursika et al., The autofluorescence of plastic materials and chips measured under laser irradiation, 2005, Lab Chip 5(12): 1348-1354.
Wabuyele et al., Single molecule detection of double-stranded DNA in poly(methylmethacrylate) and polycarbonate microfluidic devices, 2001, Electrophoresis 22(18): 3939-48.
Hawkins and Yager, Nonlinear decrease of background fluorescence in polymer thin-films—a survey of materials and how they can complicate fluorescence detection in IJTAS, 2003, Lab Chip, 3(4): 248-52.
Kan et ai, DNA sequencing and genotyping in miniaturized electrophoresis systems, 2004, Electrophoresis 25 (21-22): 3564-3588.
Strauss-Soukup et al., Effects of Neutralization Pattern and Stereochemistry on DNA Bending by Methylphosphonate Substitutions, 1997, Biochemistry 36:8692-8698.
Milligan et al., Current concepts in antisense drug design, 1993, J. Med. Chem. 36:1923-1937 17.
Becker et al., Polymer micrfabrication methods for microfluidic analytical applications, 2000, Electrophoresis 21: 12-26.
Becker and Gartner, Polymer microfabrication technologies for microfluidic systems, 2008, Analytical and Bioanalytical Chemistry, 390(1 ):89.
Geiss et al., Direct Multiplexed Measurement of Gene Expression with Color-Coded Probe Pairs, 2008, Nature Biotechnology, 26(3), 317-325.
Anasek et al., Scaling and the Design of Miniaturized Chemical-Analysis Systems, 2006, Nature, 442, 374-380.
Zhang and Xing, Miniaturized PCR Chips for Nuclic Acid Amplification and Analysis: Latest Advances and Future Trends, 2007, Nucleic Acids Research, 1-15.
Liu et al, Integrated Portable Polymerase Chain Reaction-Capillary Electrophoresis Microsystem for Rapid Forensic Short Tandem Repeat Typing, 2007, Anal. Chem., 79, 1881-9.
Fiorini and Chiu, Disposable Microfluidic Devices: Fabrication, Function, and Application, 2005, BioTechniques, 38, 429-446.
Pal et al., An Integrated Microfluidic Device for Influenza and Other Genetic Analyses, 2005, Lab Chip, 5, 1024-1032.
Burns et al., An Integrated Nanoliter DNA Analysis Device, 1998, Science, 282, 484-487.
Liu et al., Automated Parallel DNA Sequencing on Multiple Channel Microchips, 2000, Proc Natl Acad Sci, 97(10), 5369-5374.
Paegel et al., High Throughput DNA Sequencing with a Microfabricated 96-lane Capillary Array Electrophoresis Bioprocessor, 2002, Proc Nat! Acad Sci, 99(2), 574-579.
Gerstner Andreas O H et al; "Near-infrared dyes for six-color immunophenotyping by laser scanning [g] cytometry"; Cytometry; Jul. 1, 2002; pp. 115-123; vol. 48; No. 3; Wiley.
Mittag Anja et al.; "Polychromatic (eight-color) slide-based cytometry for the phenotyping of leukocyte, NK, and [g]NKT subsets"; Cytometry; Jun. 2005; pp. 103-115; vol. 65A; No. 2; Wiley.
Janasek et al., Scaling and the Design of Miniaturized Chemical-Analysis Systems, 2006, Nature, 442, 347-380.
Kamentsky L A et al, "Slide-Based Laser scanning cytometry"; ACTA Cytologica; Jan. 1, 1997; pp. 123-143; vol. 41; No. 1; International Academy of Cytology, Chicago, IL, US.

* cited by examiner

INTEGRATED SYSTEMS FOR THE MULTIPLEXED AMPLIFICATION AND DETECTION OF SIX AND GREATER DYE LABELED FRAGMENTS

CROSS-REFERENCE TO RELATED APPLICATIONS

This application is a continuation of U.S. Ser. No. 13/191,952 filed on 27 Jul. 2011 which is a continuation of U.S. Ser. No. 12/080,751, filed on 4 Apr. 2008, now issued as U.S. Pat. No. 8,018,593 and entitled "Integrated Nucleic Acid Analysis", which claims the benefit of the filing date, under 35 U.S.C. §119(e), of U.S. Provisional Application Ser. No. 60/921,802 filed 4 Apr. 2007; U.S. Provisional Application Ser. No. 60/964,502 filed 13 Aug. 2007; and U.S. Provisional Application Ser. No. 61/028,073 filed 12 Feb. 2008, each of that is hereby incorporated by reference in its entirety. This application also incorporates by reference, in their entireties, two U.S. Patent applications filed on Apr. 4, 2008; the first entitled "METHODS FOR RAPID MULTIPLEXED AMPLIFICATION OF TARGET NUCLEIC ACIDS", U.S. Ser. No. 12/080,746, now issued as U.S. Pat. No. 8,425,861; and the second entitled "PLASTIC MICROFLUIDIC SEPARATION AND DETECTION PLATFORMS", U.S. Ser. No. 12/080,745, now issued as U.S. Pat. No. 8,858,770.

FIELD OF THE INVENTION

This invention is in the field of microfluidics for the analysis of nucleic acids.

BACKGROUND OF THE INVENTION

There is an unmet need for the development of instruments and technologies that would permit fully integrated (i.e., sample-in to results-out) focused nucleic acid analysis, defined as the rapid identification (by nucleic acid sequencing or fragment sizing) of a subset of a given human, animal, plant, or pathogen genome. Focused nucleic acid sequencing will enable end-users to make real-time clinical, forensic, or other decisions. For example, many common human diseases can be diagnosed based on less than 1000 base pairs of DNA sequence, orders of magnitude less than required to generate a complete human genome. Similarly, precise determination of the sizes of sets of less than 20 specific DNA fragments generated by short tandem repeat analysis is sufficient to identify a given individual. Depending on the application, focused nucleic analysis can be performed in a variety of settings, including hospital laboratories, physician's offices, the bedside, or, in the case of forensic or environmental applications, in the field.

There are several unmet needs for improved DNA sequencing and fragment sizing systems. First, there is an unmet need for DNA sequencing and fragment sizing instruments that are easy to use and do not require highly trained operators. Second, there is an unmet need for systems that eliminate all manual processing. As a result, only minimal operator training would be required and the system could be readily operated by individuals constrained by challenging environments such as would be encountered, for example, by a first responder wearing a haz-mat suit.

Third, there is an unmet need for ultrafast analysis that does not sacrifice the need for complete, accurate, and reliable data. For human identification applications, an appropriate time to result is 45 minutes or less, well under the days to weeks required using conventional technology. For clinical applications such as sequencing infectious agents to determine an appropriate treatment regimen, 90 minutes or less is a reasonable time to answer, allowing treatment with antibacterial and antiviral medications to be initiated shortly after a patient's arrival in an emergency room. Regardless of application, there is an unmet need to generate actionable data in real time. A short time to answer also allows a concomitant increase in sample throughput.

Fourth, there is an unmet need for miniaturization. Many DNA analysis systems require an entire laboratory and related support. For example, the high throughput Genome Sequencer FLX (Roche Diagnostics Corp, Indianapolis, Ind.) DNA sequencing system requires only a benchtop for installation but a large laboratory to perform the required library construction. Miniaturization is important both for laboratory and point-of-care use as well as field operation. It is also important for cost reduction per sample.

Fifth, there is an unmet need for ruggedization. For many applications, particularly those in forensics, the military, and homeland defense, the DNA analysis instrument must be operable in the field. Accordingly, the instrument must be capable of transport whether carried on a soldier's back, driven in a police vehicle, or dropped from a helicopter into a battlefield. Similarly, the instrument must be able to withstand and function under environmental extremes, including temperature, humidity and airborne particulates (e.g., sand).

Sixth, there is an unmet need for systems that can accept multiple sample types and perform highly multiplexed analyses in parallel. For most applications, capability of analysis of DNA from a single sample type in a singleplex reaction is not acceptable to perform meaningful DNA analysis.

Developers of microfluidics (also referred to as micro total analysis systems (µTAS) or lab-on-a-chip technologies, see, Manz et al., *Sens. Actuators B* 1990, 1, 244-248) who are seeking to condense complex series of laboratory manipulations onto biochips have recognized certain of these unmet needs, but to date, have been unable to design integrated biochips and instruments that perform all of the biochemical and physical processes necessary or desirable to allow microfluidic nucleic acid analysis to address these needs. As a result, focused nucleic acid analysis has not entered into widespread use in society today.

The development of microfluidic systems involves the integration of microfabricated components, such as microscale separations, reactions, microvalves and pumps and various detection schemes into fully functional devices (see, e.g., Pal et al., *Lab Chip* 2005, 5, 1024-1032). Since Manz et al. (supra), demonstrated capillary electrophoresis on a chip in the early 1990's, others have sought to improve upon it. Several groups have demonstrated integration of DNA processing functionality with biochip separation and detection. Integrated devices in a glass-PDMS (polydimethylsiloxane) hybrid structure have been reported (Blazej et al., *Proc Natl Acad Sci USA* 2006, 103, 7240-5; Easley et al., *Proc. Natl. Acad. Sci. USA* 2006, 103, 19272-7; and Liu et al., *Anal. Chem.* 2007, 79, 1881-9). Liu coupled multiplex polymerase chain reaction (PCR), separation and four dye detection for human identification by short tandem repeat (STR) sizing. Blazej coupled Sanger sequencing reaction, Sanger reaction cleanup, electrophoretic separation and four dye detection for DNA sequencing of pUC18 amplicon. Easley coupled solid phase extraction of DNA, PCR, electrophoretic separation and single color detection to identify the presence of bacterial infection in blood. An integrated silicon-glass device coupling PCR, electrophoretic separation and single color detection was demonstrated by Burns (Pal, 2005, Id.). A hybrid device coupling a glass-PDMS portion for PCR to a poly(methyl methacrylate) (PMMA) portion for electrophoretic separation and single color detection for identifying the presence of bacteria DNA was reported by Huang (Huang et al., Electrophoresis 2006, 27, 3297-305).

Koh et al., report a plastic device that coupled PCR to biochip electrophoretic separation and single color detection for identifying the presence of bacterial DNA (Koh et al., Anal. Chem. 2003, 75, 4591-8). A silicone based device that couples DNA extraction, PCR amplification, biochip electrophoretic separation and single color detection was reported by Asogowa (Asogowa M, Development of portable and rapid human DNA Analysis System Aiming on-site Screening, 18th International Symposium on Human Identification, Poster, Oct. 1-4, 2007, Hollywood, Calif., USA). U.S. Pat. No. 7,332,126 (Tooke et al.) describes the use of centrifugal force to effect microfluidic operations required for nucleic acid isolation and cycle sequencing. However, this approach is based on small sample volumes, (those of the order of one to a few µL). As a result, the device is not useful for the processing of large samples for the isolation and analysis of nucleic acids, especially in highly parallel fashion, because the fluid samples must be applied to the device while stationary, which is, the disc must be able to contain all the fluids required for operation prior to centrifugation (potentially up to 100s of mL for a highly-parallel device). Secondly, the device is limited to sample preparation and cycle sequencing, of bacterial clones (e.g., plasmid DNA).

There are several deficiencies in those devices that attempt to integrate DNA processing with biochip electrophoretic separation. First, detection is limited by either information content per assay (most use single color detectors although some have up to four color detection systems) or throughput (single sample or two sample capability). Second, these devices do not represent complete sample-to-answer integration, e.g., Blazej's device requires off-board amplification of template DNA prior to cycle sequencing, while others use samples that require pre-processing of some sort (e.g., Easley and Tooke require lysis of the sample before addition). Third, some of the processing choices made for these devices negatively impact time-to-answer: for example, the hybridization-based method of Blazej requires more than 20 minutes for cleanup of the cycle sequencing product. Fourth, many of these devices are fabricated in part or in-whole glass or silicon. The use of these substrates and corresponding fabrication techniques make them inherently costly (Gardeniers et al., Lab-on-a-Chip (Oosterbroeck R E, van den Berg A, Eds.). Elsevier: London, pp 37-64 (2003)) and limit them to applications where reuse of the devices must be performed; for many applications (such as human ID) this leads to the risk of sample contamination. Finally, the demonstrated technology is inappropriate for two applications, human identification via STR analysis and sequencing. For example, the Easley and Pal devices both suffer from poor resolution-much worse than a single base. Fragment sizing applications (e.g., human identification by analysis of short tandem repeat profiles) and sequencing both require single base resolution.

In addition to the limitations of the prior art with respect to microfluidic integration, problems with respect to fluorescence detection also limit the widespread application of nucleic acid analysis beyond conventional laboratory work. The most widely used commercial sequencing kits (Big-Dye™ v3.1 [Applied Biosystems] and DYEnamic™ ET [GE Healthcare Biosciences Corp, Piscataway, N.J.]) are based on a twenty year old detection method for four color (see, e.g., U.S. Pat. Nos. 4,855,225; 5,332,666; 5,800,996; 5,847162; 5,847,162). This method is based on resolution of the emission signal of a dye-labeled nucleotide into four different colors, one representing each of the four bases. These four-color dye systems have several disadvantages, including inefficient excitation of the fluorescent dyes, significant spectral overlap, and inefficient collection of the emission signals. The four color dye systems are especially problematic because they limit the amount of information that can be gained from a given electrophoretic (or other) separation of sequenced products.

There is an unmet need for a system capable of achieving high information content assays in electrophoretic systems based on separation and detection of DNA fragments by both fragment size and by color (dye wavelengths). The maximum number of DNA fragments that can be distinguished by electrophoresis is determined by the readlength of the separation and the resolution of the device. The maximum number of colors that can be detected is determined in part by the availability of fluorescent dyes and the wavelength discrimination of the detection system. Current biochip detection systems are typically limited to single color, although up to 4 color detection has been reported.

STR analysis for human identification is an example of DNA fragment sizing based on color multiplexing and allows simultaneous analysis up to 16 loci (AmpFlSTR Identifiler kit; Applied Biosystems, Foster City, Calif.) and PowerPlex16 kit (Promega Corporation, Madison, Wis.). Using four or five fluorescent dyes, a single separation channel can discriminate among the sizes of the many allelic variants of each locus. Several fragment sizing applications would require more than 16 fragments to be separated and detected on a single lane. For example, the identification of pathogens by fingerprinting (i.e., the separation and detection of a large number of characteristic DNA fragments) and the diagnosis of aneuploidy by surveying the entire human genome can be accomplished by looking at several dozen or several hundred loci, respectively.

One approach to increasing the number of loci that can be detected in a single separation channel is to broaden the range of fragment sizes generated, in part by increasing the fragment sizes of additional loci. The use of longer fragments for additional loci is not ideal, however, as amplification of larger fragments is more susceptible to inhibitors and DNA degradation, leading to lower yields of longer fragments relative to shorter fragments. Furthermore, the generation of longer fragments also requires an increase in the extension time and hence, an increase in the total assay time. There is an unmet need to increasing the number of loci that can be detected in a given separation channel by increasing the number of dye colors that can be simultaneously detected.

There is an unmet need to increase the capacity of Sanger sequencing separations (and therefore decrease the cost, labor, and space of the process) by increasing the number of DNA sequences that can be analyzed in a single separation channel. In addition, in some applications, multiple DNA fragments are sequenced that generate difficult to read "mixed sequence" data; there is a need to develop an approach in that mixed sequences can be interpreted correctly.

One approach to increasing the capacity of Sanger separation channels and developing the ability to interpret mixed sequences is to increase the number of dye colors utilized in the sequencing reactions. In both DNA sequencing and fragment sizing, multiple fragments labeled with different dyes can be detected at the same time. In general, the separation between peak emission wavelengths of adjacent dyes must be large enough relative to peak width of the dyes. Accordingly, the throughput of each separation channel can, for example, be doubled by utilizing two sets of 4 dyes in two independent sequencing reactions, and combining the products, and separating them on a single channel. This methodology requires the use of a total of 8 dye colors, with the first sequence reaction using a set of 4 dye colors applied to label the dideoxynucleotide terminators, and the second reaction another set of 4 dye colors applied to the label the terminators; each set of dye colors is independent so that no overlap in interpretation of the two sequences is possible. Using this same approach, a set of 12 dyes can be utilized to allow simultaneous analysis of the sequence of three DNA fragments in a single channel, a set of 16 dyes allows the analysis of four sequences, and so on, dramatically increasing the information capacity of Sanger separations.

The novel instruments and biochips of this application satisfy many unmet needs, including those outlined above.

SUMMARY OF THE INVENTION

This invention provides fully integrated microfluidic systems to perform nucleic acid analysis. These processes include sample collection, DNA extraction and purification, amplification (that can be highly multiplexed), sequencing, and separation and detection of the DNA products.

The separation and detection modules of this invention are ruggedized and capable of better than single base resolution. They are capable of detecting six or more colors and as such are useful for generating high information content from sequencing and fragment sizing applications.

Highly multiplexed rapid PCR on biochips is the subject of an U.S. Patent Application, filed on Apr. 4, 2008, assigned U.S. Ser. No. 12/080,746, and entitled, "METHODS FOR RAPID MULTIPLEXED AMPLIFICATION OF TARGET NUCLEIC ACIDS;" it is expressly hereby incorporated by reference in its entirety. Further, the PCR products can be separated and detected within a biochip as described in the U.S. patent application entitled, "PLASTIC MICROFLUIDIC SEPARATION AND DETECTION PLATFORMS", and assigned U.S. Ser. No. 12/080,745, which is expressly hereby incorporated by reference in its entirety.

Accordingly, in a first aspect, the invention provides optical detectors comprising one or more light sources positioned for illuminating one or a plurality of detection positions on a substrate; one or a plurality of first optical elements positioned for collecting and directing light emanating from the detection positions on the substrate; and a light detector positioned to accept light from the first optical elements, wherein the light detector comprises a wavelength dispersive element to separate the light from the first optical elements according to light wavelength and positioned to provide a portion of the separated light to the detection elements, wherein each of the detection elements are in communication with a first control element for simultaneously collecting detection information from each of the detection elements and, wherein said light detector detects fluorescence from at least 6 dyes labeled to one or more biological molecules, each dye having a unique peak emission wavelength.

In a second aspect, the invention provides systems for separation and detection of biological molecules comprising, a component for simultaneously separating a plurality of biological molecules in one or a plurality of channels on a substrate, wherein each channel comprises a detection position; one or more light sources positioned to illuminate the detection positions on the substrate; one or a plurality of first optical elements positioned for collecting and directing light emanating from the detection positions; and a light detector positioned to accept light directed from the first optical elements, wherein the light detector comprises a wavelength dispersive element to separate the light from the first optical elements according to light wavelength and positioned to provide a portion of the separated light to the detection elements, wherein each of the detection elements are in communication with a first control element for simultaneously collecting detection information from each of the detection elements and, wherein said light detector detects fluorescence from at least 6 dyes labeled to one or more biological molecules, each dye having a unique peak wavelength.

In a third aspect, the invention provides methods for separating and detecting a plurality of biological molecules comprising, providing one or a plurality of analysis samples into one or a plurality of microfluidic channels on a substrate, wherein each microfluidic channel comprises a detection position, and each analysis sample independently comprises a plurality of biological molecules, each independently labeled with one of at least 6 dyes, each dye having a unique peak wavelength; simultaneously separating the plurality of labeled biological molecules in each microfluidic channel; and detecting the plurality of separated target analytes in each microfluidic channel by, illuminating each detection position with a light source; collecting the light emanating from each detection position; directing the collected light to a light detector; and (i) separating the collected light by light wavelength; and (ii) simultaneously detecting the fluorescence from at least 6 dyes labeled to one or more biological molecules, each dye having a unique peak wavelength.

In a fourth aspect, the invention provides integrated biochip systems comprising (a) a biochip comprising one or a plurality microfluidic systems, wherein each microfluidic system comprises a first reaction chamber in microfluidic communication with a separation chamber, wherein the first reaction chamber is adapted for nucleic acid extraction; nucleic acid purification; pre-nucleic acid amplification cleanup; nucleic acid amplification; post-nucleic acid amplification cleanup; pre-nucleic acid sequencing cleanup; nucleic acid sequencing; post-nucleic acid sequencing cleanup; reverse transcription; pre-reverse transcription cleanup; post-reverse transcription cleanup; nucleic acid ligation; nucleic acid hybridization; or quantification; and the separation chamber comprises a detection position; and (b) a separation and detection system comprising, (i) a separation element for simultaneously separating a plurality of target analytes in the separation chambers; (ii) one or more light sources positioned to illuminate the detection positions on the biochip; (iii) one or a plurality of first optical elements positioned for collecting and directing light emanating from the detection positions; and (iv) a light detector positioned to accept light directed from the first optical elements, wherein the light detector comprises a wavelength dispersive element to separate the light from the first optical elements according to light wavelength and positioned to provide a portion of the separated light to at least six detection elements, wherein each of the detection elements are in communication with a first control element for simultaneously collecting detection information from each of the detection elements; and wherein said light detector detects fluorescence from at least 6 dyes labeled to one or more biological molecules, each dye having a unique peak wavelength.

In a fifth aspect, the invention provides integrated biochip systems biochip system comprising (a) a biochip comprising one or a plurality microfluidic systems, wherein each microfluidic system comprises a first reaction chamber in microfluidic communication with a separation chamber, wherein the first reaction chamber is adapted for nucleic acid extraction; nucleic acid purification; pre-nucleic acid amplification cleanup; nucleic acid amplification; post-nucleic acid amplification cleanup; pre-nucleic acid sequencing cleanup; nucleic acid sequencing; post-nucleic acid sequencing cleanup; reverse transcription; pre-reverse transcription cleanup; post-reverse transcription cleanup; nucleic acid ligation; nucleic acid hybridization; or quantification; and the separation chamber comprises a detection position; and (b) a separation and detection system comprising, (i) a separation element for simultaneously separating a plurality of biological molecules comprising DNA sequences, in the separation chambers; (ii) one or more light sources positioned to illuminate the detection positions on the biochip; (iii) one or a plurality of first optical elements positioned for collecting and directing light emanating from the detection positions; and (iv) a light detector positioned to accept light directed from the first optical elements, wherein the light detector comprises a wavelength dispersive element to separate the light from the first optical elements according to light wavelength and positioned to provide a portion of the separated light to at least six detection elements, wherein each of the detection elements are in communication with a first control element for simultaneously collecting detection information from each of the detection elements; and wherein said light detector detects fluorescence from at least 8 dyes labeled to one or more DNA sequences, each dye having a unique peak wavelength, said dyes being members of at least two 4-dye containing subsets, such that said dye sets are capable of detecting at least two DNA sequences in a single channel, wherein the number of dyes is a multiple of four, and the number of DNA sequences to be detected is equal to that multiple, such that each of the different dyes is present in only one subset.

DESCRIPTION OF THE DRAWINGS

FIGS. 8*h* through 8*j* are illustrations showing the mixed liquids delivered to the PCR chamber, at that point thermal cycling is initiated.

DETAILED DESCRIPTION OF PREFERRED EMBODIMENTS

I. Integration and Integrated Systems

A. General Description of Integration

Figure 1:
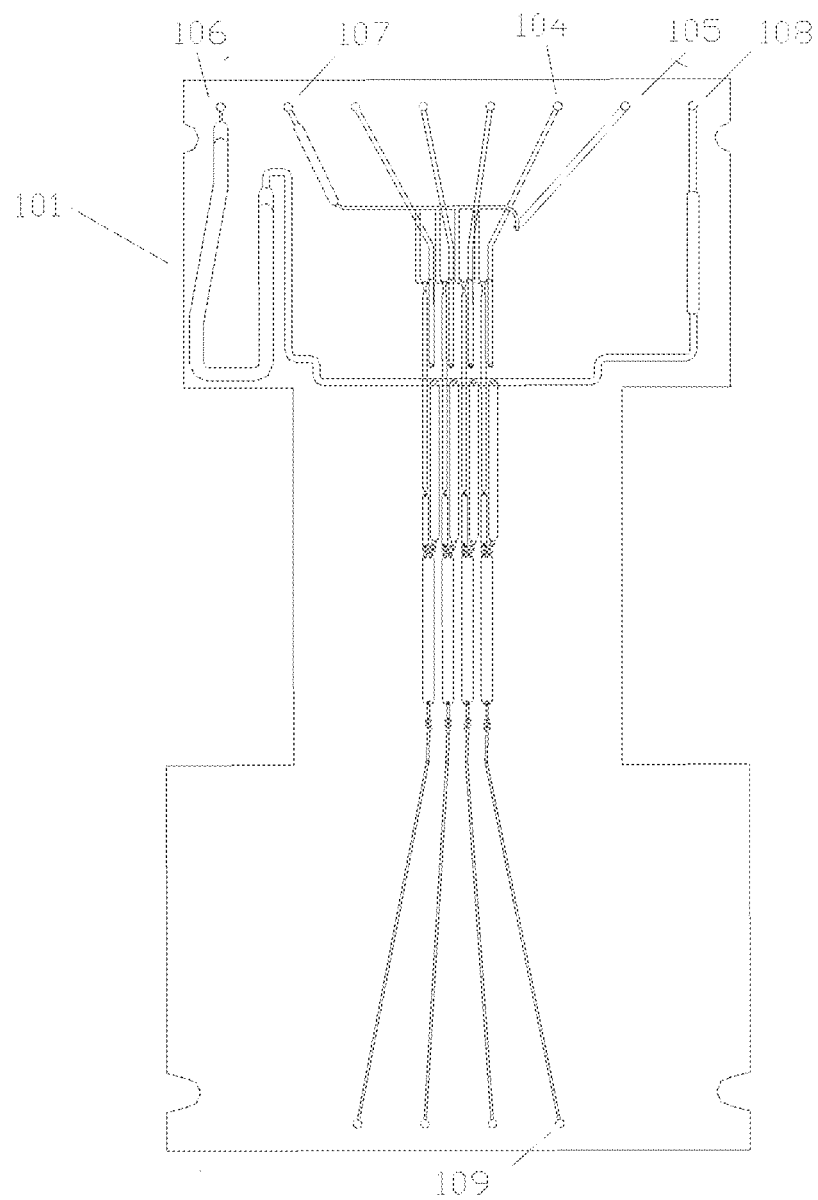
FIG. 1 is an illustration of an embodiment of an integrated biochip for lysis and template amplification for 4 individual samples.
Figure 2:
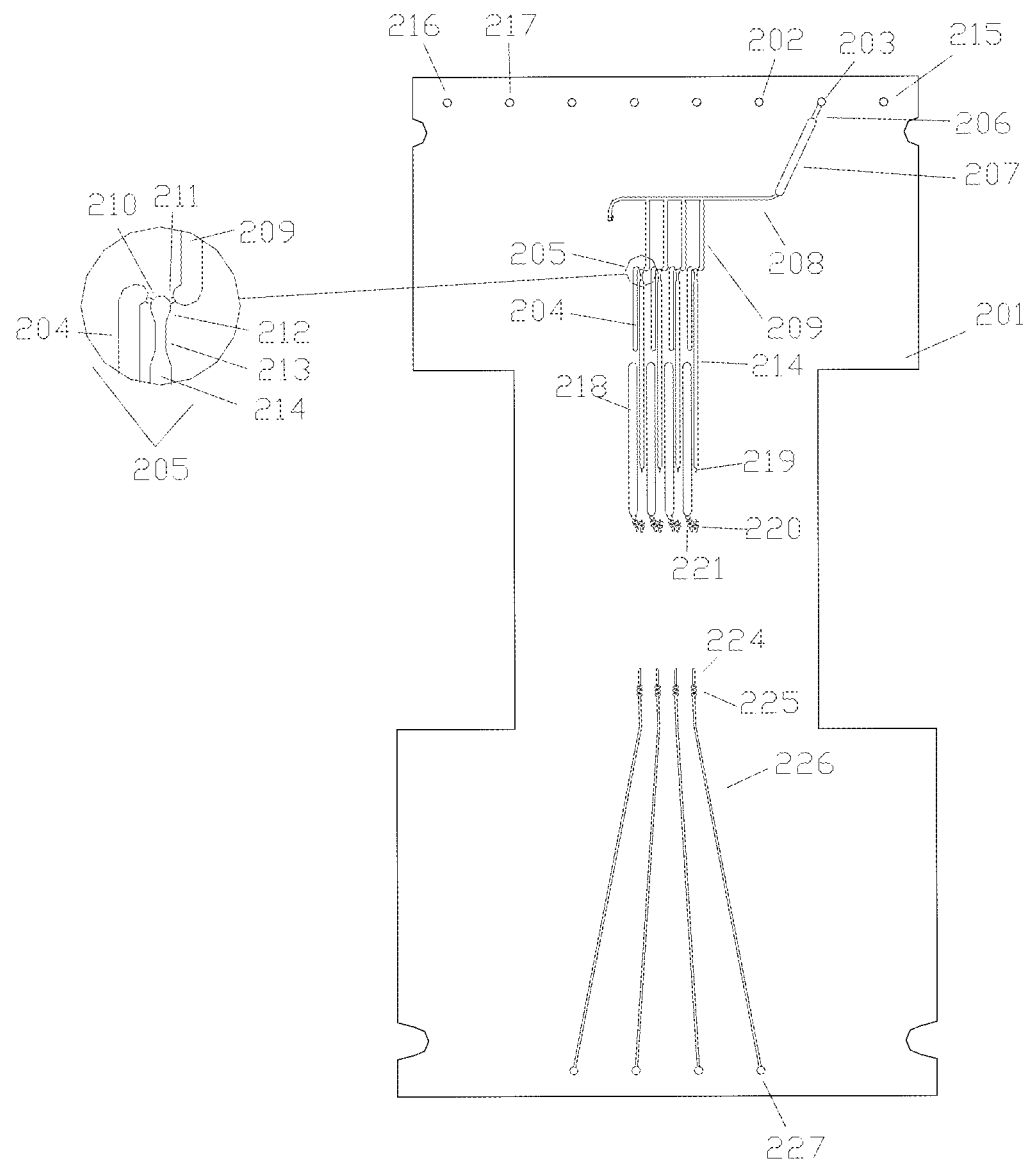
FIG. 2 is an illustration of an embodiment of the first layer of the biochip of FIG. 1.
Figure 3:
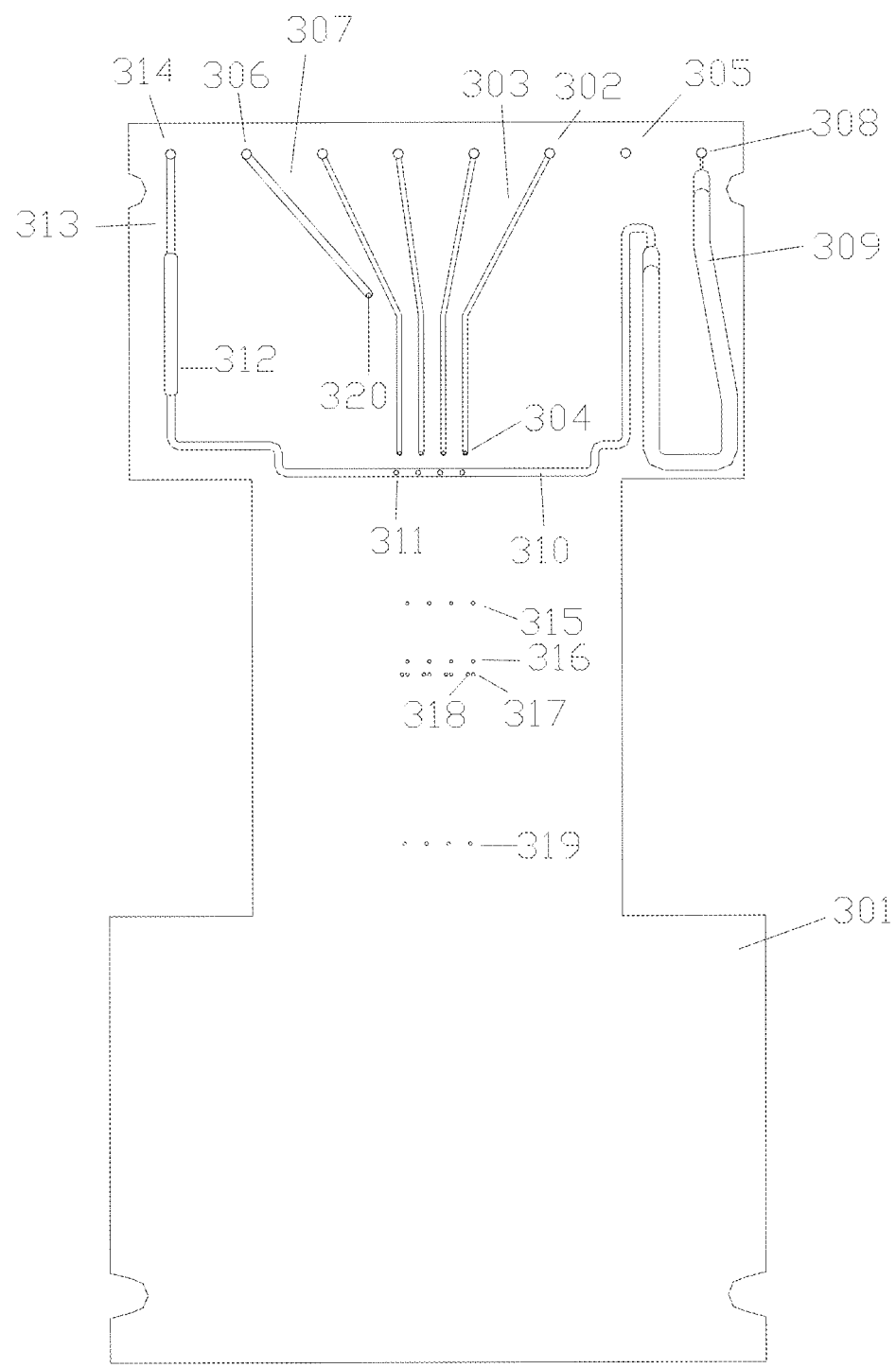
FIG. 3 is an illustration of an embodiment of the second layer of the biochip of FIG. 1.
Figure 4:
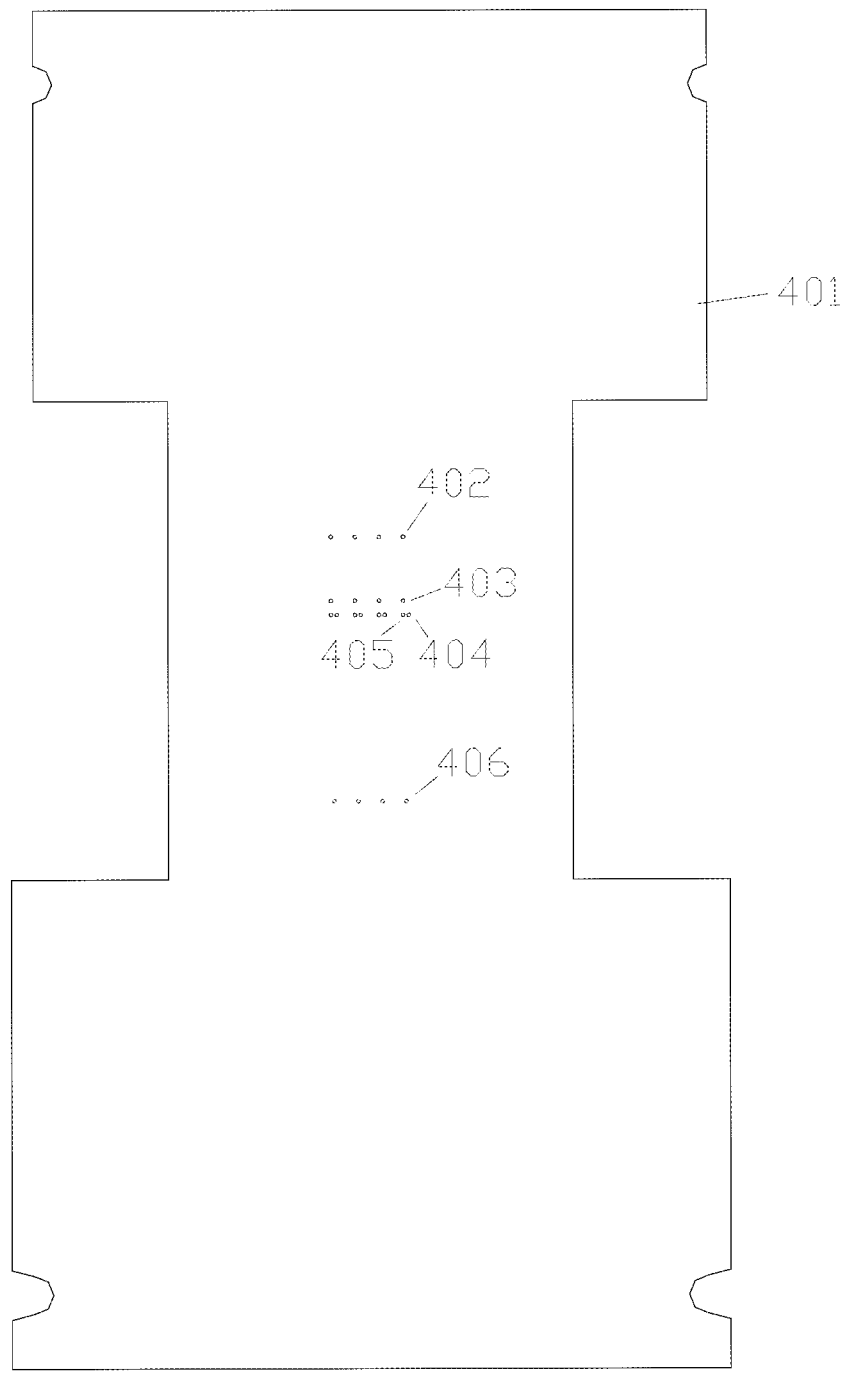
FIG. 4 is an illustration of an embodiment of the third layer of the biochip of FIG. 1.
Figure 5:
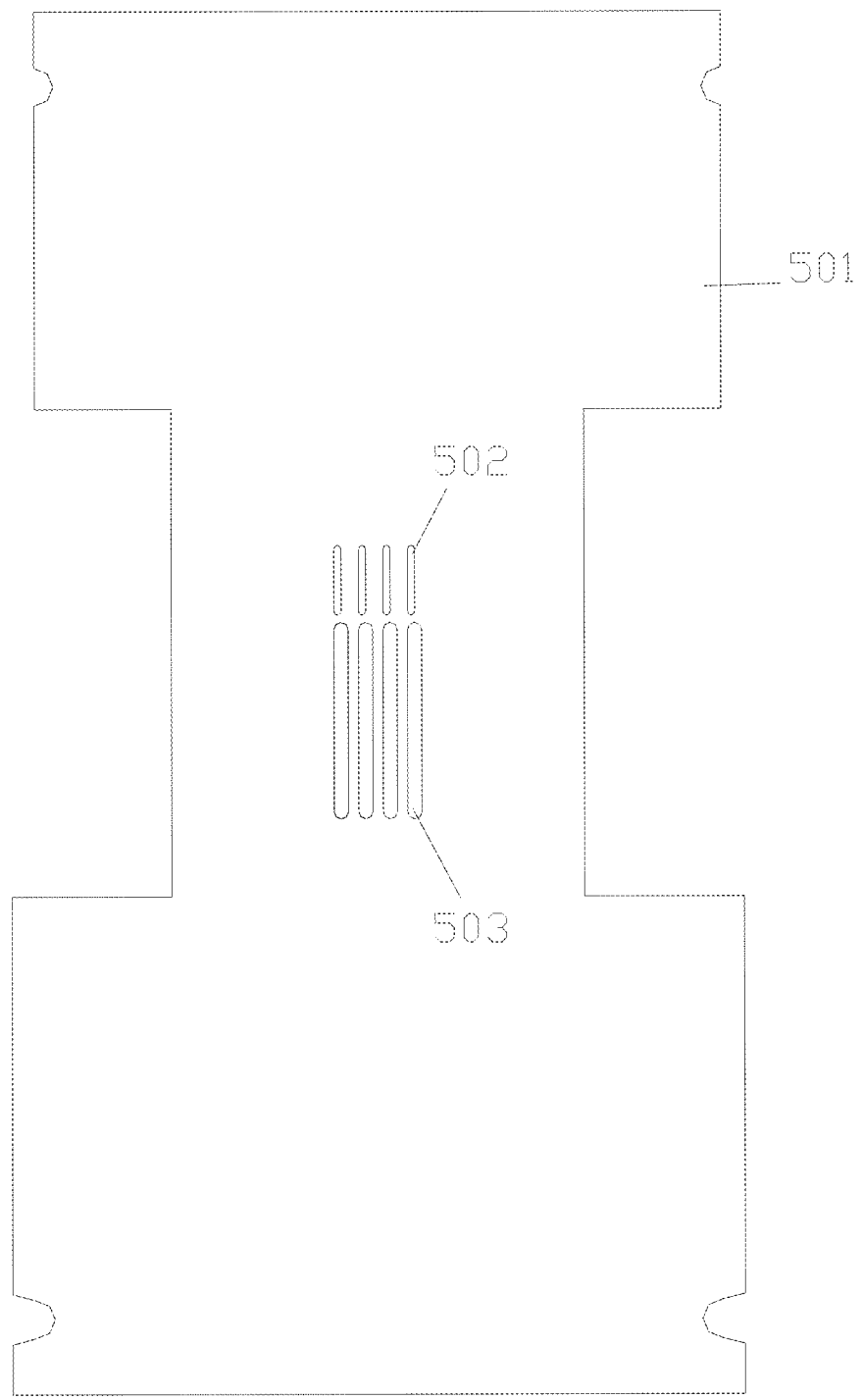
FIG. 5 is an illustration of an embodiment of the fourth layer of the biochip of FIG. 1.

Using microfluidics allows fabrication of features to perform more than one function on a single biochip. Two or more of these functions can be connected microfluidically to enable sequential processing of a sample; this coupling is termed integration.

There is a range of possible functions or component processes that must be integrated to achieve any given application, though not all processes must be implemented for any given application. As a result, the chosen integration methods must be appropriate for effectively connecting a number of different component processes in different sequences. Processes that can be integrated include, but are not limited to, the following:

1. Sample insertion;
2. Removal of foreign matter (e.g., large particulates such as dust, fibers)
3. Cell separation (i.e., the removal of cells other than those containing the nucleic acid to be analyzed, such as the removal of human cells (and accordingly, human genomic DNA) from clinical samples containing microbial nucleic acids to be analyzed);
4. Concentration of cells containing the nucleic acids of interest;
5. Lysis of cells and extraction of nucleic acids;
6. Purification of nucleic acids from the lysate; with possible concentration of the nucleic acids to smaller volumes;
7. Pre-amplification nucleic acid clean-up;
8. Post-amplification clean-up;
9. Pre-sequencing clean-up;
10. Sequencing;
11. Post-sequencing clean-up (e.g., to remove unincorporated dye-labeled terminators and ions that interfere with electrophoresis;
12. Nucleic acid separation;
13. Nucleic acid detection;
14. Reverse transcription of RNA;
15. Pre-reverse transcription clean-up;
16. Post-reverse transcription clean-up;
17. Nucleic acid ligation;
18. Nucleic acid quantification.
19. Nucleic acid hybridization; and
20. Nucleic acid amplification (e.g., PCR, rolling circle amplification, strand displacement amplification, and multiple displacement amplification).

One of many ways in which some of these processes may be combined is in an integrated system for human identification by STR analysis. Such an system may require the coupling of DNA extraction, human specific DNA quantification, addition of a defined amount of DNA to the PCR reaction, multiplexed PCR amplification, and separation and detection (optionally, clean-up steps to remove reaction components or primers can be incorporated as well). One or more samples can be collected by techniques such as swabbing (see, Sweet et al., *J. Forensic Sci.* 1997, 42, 320-2) of whole blood, dried blood, the inner surface of the cheeks, fingerprints, sexual assault, touch, or other forensically relevant samples. Exposure to lysate (optionally in the presence of agitation) releases the DNA from the swab into a tube.

B. General Description of Integration Components and their Uses

1. Sample Collection and Initial Processing

For many applications, the following discrete components are advantageously integrated into the biochip: sample insertion; removal of foreign matter; removal of interfering nucleic acids; and concentration of cells of interest. Generally, a pre-processing component of the biochip accepts samples, performs initial removal of particulates and foreign nucleic acid containing cells, and concentrates the cells of interest into small volumes. One approach is to use a sample tube that can accept a swab (e.g., resembling a "Q-tip") and that is filled with lysis solution to perform the lysis and extraction step. The swab can be placed in contact with a number of cell-containing sites, including a bloodstain, a fingerprint, water, an air filter, or a clinical site (e.g., buccal swab, wound swab, nasal swab). The interface of these tubes with other components of the biochip may include a filter for removal of foreign matter. Another approach is to use a large-volume blood or environmental sample acquisition cartridge, which processes a 1-100 mL of sample. In the case of blood, a leukocyte reduction medium can remove human white blood cells and interfering DNA while passing microbes containing nucleic acids of interest. For environmental samples, large-mesh filters can be used to remove dust and dirt, while small-mesh filters (e.g., filters of <20 µm, <10 µm, <5 µm, <2.5 µm, <1 µm, <0.5 µm, <0.2 µm, <0.1 µm) can be used to trap microbes, concentrating them in a small volume. These pre-processing components can be separate consumables or can be attached to the integrated biochip at time of manufacture. Alternatively, the biochip can be designed to perform differential lysis to separate cells by type (e.g., sperm from vaginal epithelial cells or red blood cells from bacteria).

2. Lysis and Extraction

A variety of lysis and extraction methods can be employed. For example, a typical procedure involves the application of heat after mixing of the sample with a small quantity of a degradative enzyme such as proteinase-K, which breaks down cell walls and releases nucleic acids. Other useful methods are sonication and ultrasonication, either or both performed sometimes in the presence of beads.

For example, lysis and extraction can be performed on a sample containing $10^6$ cells or less. Depending on the application, a smaller number of starting cells can be utilized in the biochips and methods of the invention, less than $10^5$, less, than $10^4$, less than $10^3$, less than, $10^2$, less than 10, and, in cases when multi-copy sequences are to be analyzed, less than 1.

3. Purification of Nucleic Acids

One form of nucleic acid purification can be achieved by inserting a purification medium between an input and output channel. This purification medium can be silica fiber based and use chaotropic-salt reagents to lyse the biological sample, expose the DNA (and RNA) and bind the DNA (and RNA) to the purification media. The lysate is then transported via the input channel through the purification medium to bind the nucleic acids. Bound nucleic acid is washed by an ethanol based buffer to remove contaminants. This can be accomplished by flowing wash reagents via the input channel through the purification membrane. Bound nucleic acid is then eluted from the membrane by flowing an appropriate low salt buffer (e.g., Boom U.S. Pat. No. 5,234,809). A variation of this method involves the use of a differently-configured solid phase. For example, silica gel can be employed to bind nucleic acid. Paramagnetic silica beads can be used, and their magnetic properties employed to immobilize them against a channel or chamber wall during binding, wash, and elution steps. Non-magnetized silica beads may also be employed, either packed within a tight 'column' where they are retained by frits (typically manufactured into the plastic of the device, but these may also be inserted during assembly) or "free" during certain phases of their operation: Free beads can be mixed with nucleic acids and then flowed against a frit or a weir in the device to trap them so that they do not interfere with downstream processes. Other formats include sol-gels with silica particles distributed in the gel medium and polymer monoliths with silica particle inclusions, in which the carrier is cross-linked for greater mechanical stability. Essentially, any nucleic acid purification method that is functional in a conventional setting can be adapted to the integrated biochips of this invention.

4. Nucleic Acid Amplification

A variety of nucleic acid amplification methods can be employed, such as PCR and reverse-transcription PCR, which required thermal cycling between at least two, and more typically, three temperatures. Isothermal methods such as strand displacement amplification can be used, and multiple displacement amplification can be used for whole genome amplification. The teachings of the U.S. patent application entitled "METHODS FOR RAPID MULTIPLEXED AMPLIFICATION OF TARGET NUCLEIC ACIDS" (U.S. Ser. No. 12/080,746) filed on Apr. 4, 2008 is hereby incorporated by reference in its entirety (supra).

5. Nucleic Acid Quantification

One approach to quantification in a microfluidic format is based upon real-time PCR. In this method of quantification, a reaction chamber is fabricated between an input and output channel. The reaction chamber is coupled to a thermal cycler and an optical excitation and detection system is coupled to the reaction chamber to allow fluorescence from the reaction solution to be measured. The amount of DNA in the sample is correlated to the intensity of the fluorescence from the reaction chamber per cycle. See, e.g., Heid et al., *Genome Research* 1996, 6, 986-994. Other quantitation methods include the use of intercalating dyes such as picoGreen, SYBR, or ethidium bromide, either prior to or after amplification, which may then be detected using either fluorescence or absorbance.

6. Secondary Purifications

For STR analysis, multiplex-amplified and labeled PCR product can be used directly for analysis. However, electrophoretic separation performance can be greatly improved by purification of the product to remove ions necessary for PCR that interfere with the separation or other subsequent steps. Similarly, purification following cycle sequencing or other nucleic acid manipulations can be useful. Collectively, any purification step following the initial extraction or purification of nucleic acid can be considered a secondary purification. A variety of methods can be employed, including ultrafiltration, in that small ions/primers/unincorporated dye labels are driven through a filter, leaving the desired product on the filter that then can be eluted and applied directly to the separation or subsequent module. Ultrafiltration media include polyethersulfone and regenerated cellulose "woven" filters, as well as track-etch membranes, in which pores of highly-uniform size are formed in an extremely thin (1-10 µm) membrane. The latter have the advantage of collecting product of size larger than the pore size on the surface of the filter, rather than capturing the product at some depth below the surface. The amplified nucleic acids may also be purified using the same methods outlined above (i.e., classic solid phase purification on silica). Still further methods include hydrogels, cross-linked polymers that have the property of pore size variability, that is, the pore size changes in response to environmental variables such as heat and pH. In one state, the pores are tight and PCR product cannot pass through. As the pores dilate, hydrodynamic or electrophoretic flow of product through the pores is possible. Another method is the use of hybridization, either non-specific hybridization of product to random DNA immobilized on a surface (such as the surface of beads) or specific hybridization, in that a complement to a sequence tag on the product is on the solid surface. In this approach, the product of interest is immobilized through hybridization and unwanted material removed by washing; subsequent heating melts the duplex and releases the purified product.

7. Cycle Sequencing Reaction

Classic cycle sequencing requires thermal cycling, much as PCR. The preferred methods are those employing dye-labeled terminators, such that each extension product bears a single fluorescent label corresponding to the final base of the extension reaction.

8. Injection, Separation, and Detection

Figure 14:
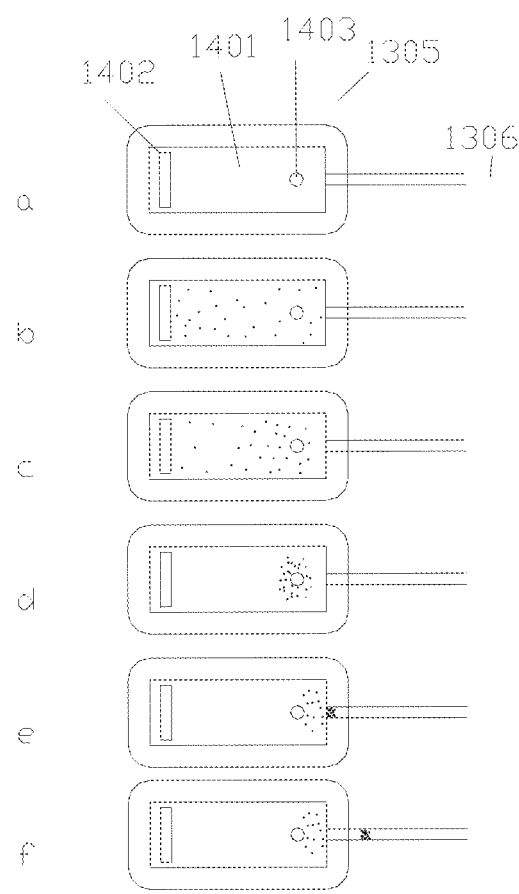
FIG. 14 is an illustration showing concentration of labeled nucleic acid fragments by counter electrode and injection into a separation channel.

Injection, separation and detection of labeled nucleic acid fragments into the electrophoresis channel can be performed in a variety of ways, which have been described in the U.S. patent application entitled "PLASTIC MICROFLUIDIC SEPARATION AND DETECTION PLATFORMS", filed on Apr. 4, 2008 and assigned U.S. Ser. No. 12/080,745, which is hereby incorporated by reference in its entirety. First, cross-injectors as discussed therein can be used to inject a portion of the sample. In an alternative embodiment, electrokinetic injection ("EKI") can be used. In either case, further concentration of sequencing product in the vicinity of the open end of the loading channel (in the case of cross injection) or separation channel (in the case of EKI) can be performed by electrostatically concentrating product near an electrode. A two-electrode sample well on the electrophoresis portion of the chip is shown in FIG. 14. Both electrodes are coated with a permeation layer that prevents DNA from contact the metal of the electrode but allows ions and water access between the sample well and the electrode. Such permeation layers can be formed of cross-linked polyacrylamide (see US Patent Application Publication US 2003-146145-A1). The electrode farthest from the channel opening is the separation electrode, while that nearest the channel opening is the counterelectrode. By charging the counterelectrode positively relative to the separation electrode, DNA will be drawn to the counterelectrode and concentrated near the opening of the separation channel. By floating the counterelectrode and injecting using the separation electrode and the anode at the far end of the separation channels, concentrated product is electrokinetically injected.

C. Integration Methods

The biochip also contains several different means for integrating the functional modules. These means involve the transport of liquids from point to point on the biochip, the control of flow rates for processes that are flow-rate dependent, (e.g., some washing steps, particle separation, and elution), the gating of fluid motion in time and space on the biochip (e.g., through the use of some form of valve), and the mixing of fluids.

A variety of methods can be used for fluid transport and controlled fluid flow. One method is positive-displacement pumping, in that a plunger in contact with either the fluid or an interposing gas or fluid drives the fluid a precise distance based on the volume displaced by the plunger during the motion. An example of such a method is a syringe pump. Another method is the use of integrated elastomeric membranes that are pneumatically, magnetically, or otherwise actuated. Singly, these membranes can be used as valves to contain fluids in a defined space and/or prevent premature mixing or delivery of fluids. When used in series, however, these membranes can form a pump analogous to a peristaltic pump. By synchronized, sequential actuation of membranes fluid can be "pushed" from its trailing side as membranes on the leading side are opened to receive the moving fluid (and to evacuate any displaced air in the channels of the device). A preferred method for actuation of these membranes is pneumatic actuation. In such devices, the biochip is comprised of fluidic layers, at least one of that has membranes, one side of that is exposed within the fluid channels and chambers of the device. The other side of the membrane is exposed to a pneumatic manifold layer that is plumbed to a pressure source. The membranes are opened or closed by the application of pressure or vacuum. Valves that are normally open or normally closed can be used, changing state under the application of pressure or vacuum. Note that any gas can be used for actuation, as the gas does not contact the fluids under analysis.

Yet another method for driving fluids and controlling flow rates is to apply vacuum or pressure directly on the fluids themselves, by altering the pressure at the leading, trailing, or both menisci of the fluid. Appropriate pressures (typically in the range of 0.05-3 psig) are applied. Flow rates also can be controlled by properly sizing the fluidic channels, as the flow rate is proportional to the pressure differential across the fluid and the hydraulic diameter to the fourth power and inversely proportional to the length of the channel or the liquid plug and the viscosity.

Fluid gating can be achieved using a variety of active valves. The former can include piezoelectric valves or solenoid valves that can be directly incorporated into the chip, or applied to the biochip such that ports on the main chip body communicate with the valves, directing fluid into the valves and then back into the chip. One drawback to these types of valves is that for many applications, they are likely to be difficult to manufacture and too expensive to incorporate into disposable integrated devices. A preferable approach is to use of membranes as valves, as discussed above. For example, membranes actuated by 10 psig can be used to successfully contain fluids undergoing PCR.

In some applications, capillary microvalves, which are passive valves, can be preferable. Essentially, microvalves are constrictions in the flow path. In microvalves, surface energy and/or geometric features such as sharp edges can be used to impede flow when the pressure applied to the fluid is below a critical valve, termed the burst pressure, which is generally given by the relation:

$$P_{valve} \alpha (\gamma/d_H)*\sin(\theta_c)$$

where $\gamma$ is the surface tension of the liquid, $d_H$ is the hydraulic diameter of the valve (defined as 4*(cross-sectional area)/cross-sectional perimeter), and $\theta_c$ is the contact angle of the liquid with the valve surface.

Properties that make passive valves preferable for certain applications include: extremely low dead-volume (typically in the picoliter range), and small physical extent (each being only slightly larger than the channels leading to and from the valve). Small physical extent allows for a high density of valves on a given surface of the biochip. Additionally, certain capillary valves are very simple to manufacture, consisting essentially of a small hole in a sheet of plastic, with or without a surface treatment. Judicious use of capillary valves can reduce the total number of membrane valves required, simplify the overall manufacture and create a robust system.

Capillary valves implemented in devices of the invention are of two types: In-plane valves, in that the small channels and sharp corners of the valves are formed by creating "troughs" in one layer and bonding this layer to a featureless lid (typically another layer of the device); and through-hole valves, in that small (typically 250 μm or less) holes are made in an intermediate layer between two fluidics-carrying layers of the device. In both cases, treatment with fluoropolymer can be used to increase the contact angle of fluids in contact with the valves.

Figure 7:
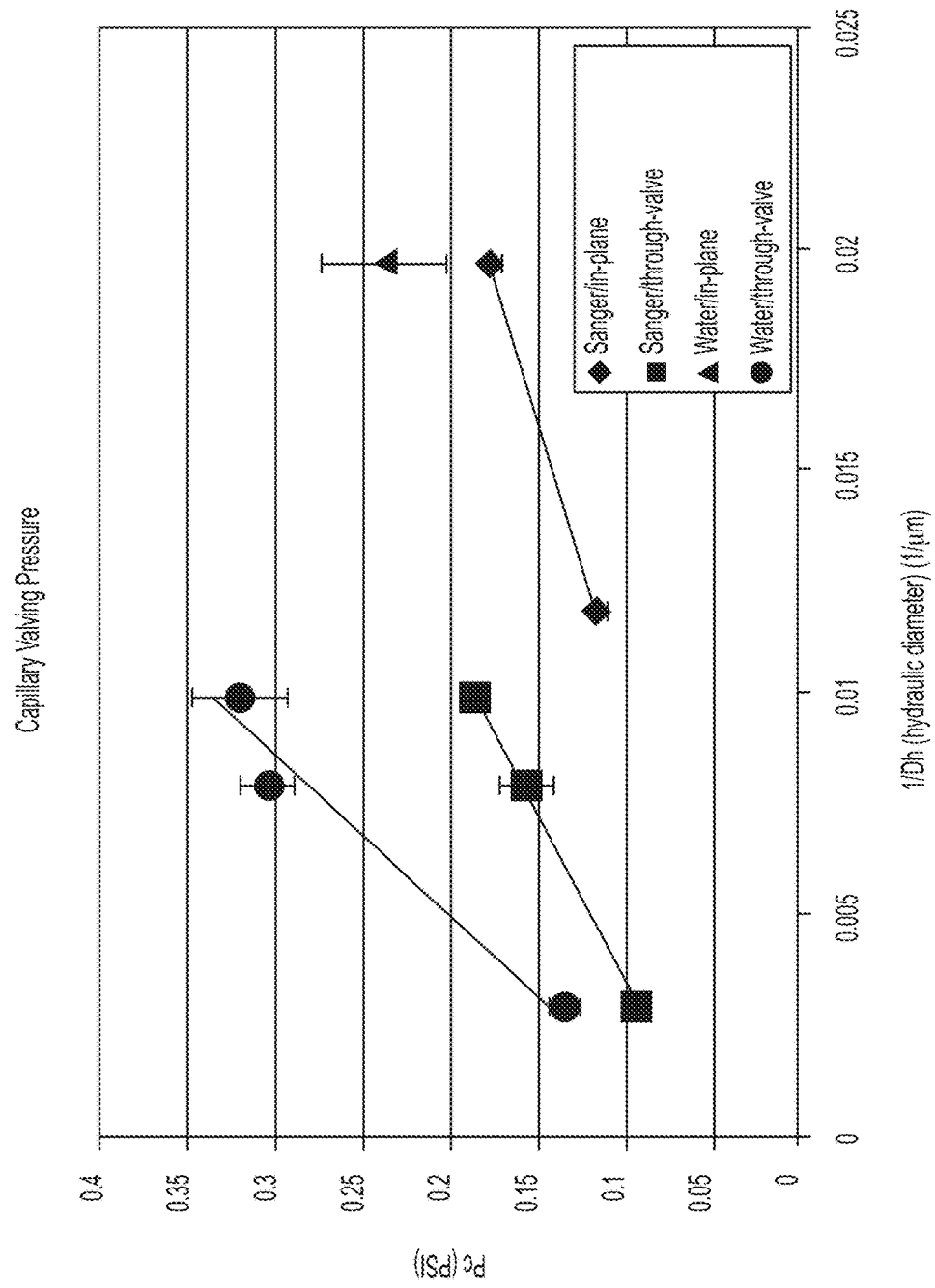
FIG. 7 is a graph illustrating capillary valving pressure as a function of inverse hydraulic diameter of the valve for deionized water and cycle sequencing reagents for two valve types, in-plane and through-hole valves.

FIG. 7 shows the valving performance of these valves for liquids of interest, namely, deionized water and cycle sequencing reagent, as a function of valve size for the case of fluoropolymer treatment. In both cases, the expected dependence of valving pressure on valve dimension is observed (Pressure~1/diameter). Through-hole valves have significant advantages over in-plane valves. First, they are easier to manufacture, in that small through-holes can be readily made in a sheet of plastic, either by molding around posts, punching, die-cutting, drilling, or laser-drilling after the valve layer has been created. In-plane valves require fairly precise fabrication, and very fine valves (with high valving pressures) necessitate the use of lithographic techniques to create the required molding or embossing tools. Second, through-hole valves can be more completely coated with fluoropolymer on "all sides." The application of low-surface-tension fluoropolymer solution to a hole results in complete coating of the internal walls of the hole by capillary action. Coating of all sides of an in-plane valve requires application of fluoropolymer to both the valve as well as the region of the mating layer that seals over the valve. As a result, typical in-plane valves are formed without coating on the "roof" of the valve.

In machined prototypes, through-hole valves are both easier to implement and exhibit greater valving pressures, as illustrated in FIG. 7.

Mixing can be accomplished in a variety of ways. First, diffusion can be used to mix fluids by co-injecting the two fluids into a single channel, usually of small lateral dimension and of sufficient length such that the diffusion time $$t_D = (\text{width})^2/(2*\text{Diffusion constant})$$

is satisfied at the given flow rates. Unfortunately, this type of mixing is typically inadequate for mixing large volumes quickly, because the diffusion or mixing time scales with the channel width squared Mixing can be enhanced in a variety of ways, such as lamination, in that the fluid stream is divided and recombined. (Campbell and Grzybowski *Phil. Trans. R. Soc. Lond. A* 2004, 362, 1069-1086); or through the use of fine microstructure to create chaotic advection within the flow channel (Stroock et al., *Anal. Chem.* 2002. 74, 5306-4312). In systems using active pumps and valves, mixing can be accomplished by cycling fluid between two points on the device multiple times. Finally, the latter also can be accomplished in systems using capillary valves. A capillary valve disposed between two channels or chambers acts as a pivot for fluid flow; as fluid flows from one channel into the other through the capillary, the trailing meniscus is trapped if sufficiently low pressure is used to pump the fluid. Reversal of the pressure drives the fluid back into the first channel, and it is again pinned at the capillary. Multiple cycles can be used to efficiently mix components.

Approaches to separation and detection in microfluidic formats are described in the U.S. patent application entitled "PLASTIC MICROFLUIDIC SEPARATION AND DETECTION PLATFORMS", and assigned U.S. Ser. No. 12/080,745, filed on Apr. 4, 2008, which is incorporated by reference in its entirety (see, e.g., paragraphs 68-79, 94-98, therein).

Figure 13:
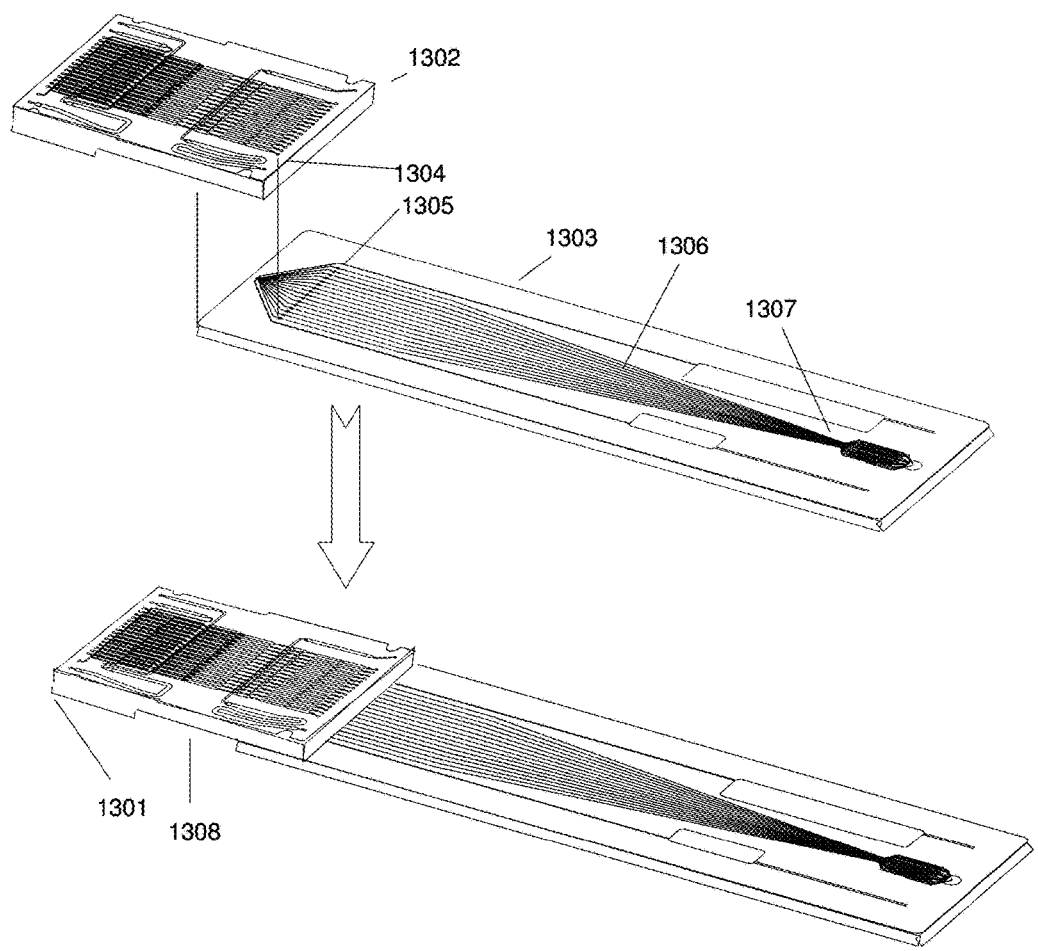
FIG. 13 is an illustration showing an embodiment of an integrated biochip for the performance of template amplification, cycle sequencing, sequencing product cleanup, separation by electrophoresis and detection by laser-induced fluorescence.

The upper portion of FIG. 13 shows the construction of the integrated biochip (1301) from two components which are bonded in or during manufacture. First, a 16-sample biochip (1302) combining the lysis, amplification, and sequencing features of the biochip of FIG. 1 with the sequencing product purification features of the biochip of FIG. 11 and second, a 16-lane plastic separation biochip (1303). Purified sequencing product can also be electrokinetically injected prior to separation.

D. Fabrication Methods

The devices of the invention can be primarily composed of plastics. Useful types of plastics include, but are not limited to: cyclic olefin polymer (COP); cyclic olefin copolymer (COC); (both of that have excellent optical quality, low hygroscopicity, and high operating temperatures when of sufficient molecular weight); poly(methyl methacrylate) (PMMA) (readily machinable and can be obtained with excellent optical properties); and polycarbonate (PC) (highly-moldable with good impact resistance and a high operating temperature). More information about materials and fabrication methods are contained in the U.S. patent application entitled "METHODS FOR RAPID MULTIPLEXED AMPLIFICATION OF TARGET NUCLEIC ACIDS" (U.S. Ser. No. 12/080,746) that has been incorporated by reference (supra).

A variety of methods can be used to fabricate the individual parts of the biochip and to assemble them into a final device. Because the biochip can be composed of one or more types of plastic, with the possible inclusion of inserted components, the methods of interest pertain to creation of individual parts followed by post-processing of parts and assembly.

Plastic components can be fabricated in several ways, including injection molding, hot embossing and machining. Injection molded parts can be comprised of both gross features (such as fluid reservoirs) as well as fine features (such as capillary valves). In some cases, it can be preferable to create fine features on one set of parts and larger features on another set, because the approaches to injection molding of these differently-sized features can vary. For large reservoirs (measuring several (about 1-50 mm) mm on a side and with depths of several mm (about 1-10 mm) and capable of accommodating 100s of µL), conventional molding can be employed using machined injection molding tools, or tools created by burning into a steel or other metal using a graphite electrode that has been machined to be a negative of the tool.

For fine features, both tool creation and molding process can be varied. Tools are typically created using a lithographic process on a substrate of interest (for example, isotropic etch of glass, or deep reactive ion etching or other processes on silicon). The substrate can then be electroplated with nickel (usually after deposition of a chromium layer to promote adhesion) and the substrate removed, for example, by etching in an acid. This nickel "daughter" plate is the injection molding tool. The molding process can be somewhat different than above, as well: For fine, shallow features, compression-injection molding, in which the mold is physically compressed slightly after plastic has been injected into the cavity, has been found to be superior to standard injection molding in terms of fidelity, precision, and reproducibility.

For hot embossing, similar issues regarding gross and fine features as discussed above hold, and tools can be created as above. In hot embossing, plastic resin in the form of pellets, or as a pre-formed blank of material created through molding or embossing, can be applied to the tool surface or a flat substrate. A second tool may then brought into contact at precisely controlled temperature and pressure in order to raise the plastic above its glass transition temperature and to cause material flow to fill the cavities of the tool(s). Embossing in a vacuum can avoid the problem of air becoming trapped between tool and plastic.

Machining also can be employed to create parts. High-speed computer numerical controlled (CNC) machines can be used to create many individual parts per day from either molded, extruded, or solvent-cast plastic. Proper choice of milling machine, operating parameters, and cutting tools can achieve high surface quality (surface roughnesses of 50 nm are achievable in high-speed milling of COC (Bundgaard et al., *Proceedings of IMechE Part C: J. Mech. Eng. Sci.* 2006, 220, 1625-1632). Milling can also be used to create geometries that can be difficult to achieve in molding or embossing and to readily mix feature sizes on a single part (for example, large reservoirs and fine capillary valves can be machined into the same substrate). Another advantage of milling over molding or embossing is that no mold-release agents are needed to release the fabricated part from a molding tool.

Post-processing of individual parts includes optical inspection (that can be automated), cleaning operations to remove defects such as burrs or hanging plastic, and surface treatment. If optical-quality surfaces are required in machined plastic, polishing with a vapor of a solvent for the plastic can be used. For example, for PMMA, dichloromethane can be used, while for COC and COP, cyclohexane or toluene can be used.

Prior to assembly, surface treatments can be applied. Surface treatment can be performed to promote or reduce wetting (i.e., to change the hydrophilicity/hydrophobicity of the part); to inhibit the formation of bubbles within microfluidic structures; to increase the valving pressure of capillary valves; and/or to inhibit protein adsorption to surfaces. Coatings that reduce wettability include fluoropolymers and/or molecules with fluorine moieties that are exposed to the fluid when the molecules are adsorbed or bonded to the surfaces of the device. Coatings can be adsorbed or otherwise deposited, or they can be covalently linked to the surface. The methods that can be used to make such coatings include dip coating, passing coating reagent through the channels of the assembled device, inking, chemical vapor deposition, and inkjet deposition. Covalent bonds between coating molecules and the surface can be formed by treatment with oxygen or other plasma or UV-ozone to create an activated surface, with either subsequent deposition or co-deposition of the surface treatment molecule on the surface (see, Lee et al. *Electrophoresis* 2005, 26, 1800-1806; and Cheng et al., *Sensors and Actuators B* 2004, 99, 186-196.)

Assembly of component parts into the final device can be performed in a variety of ways. Inserted devices, such as filters, can be die-cut and then placed with a pick-and-place machine.

Thermal diffusion bonding can be used, for example for the bonding of two or more layers of the same material, each of that is of uniform thickness. Generally, the parts can be stacked and the stack placed into a hot press, where the temperature can be raised to the vicinity of the glass transition temperature of the material comprising the parts, to cause fusion at the interfaces between the parts. An advantage of this method is that the bonding is "general", i.e., any two stacks of layers of roughly the same dimensions can be bonded, regardless of the internal structure of the layers, because heat and pressure are applied uniformly across the layers.

Thermal diffusion bonding may also be used to bond more complex parts, such as those that are not planar on their bonding or opposing surfaces, by using specially-created bonding cradles. Such cradles conform to the outer surface of the layers to be bonded.

Other bonding variations include solvent-assisted thermal bonding, in that a solvent such as methanol partially solubilizes the plastic surface, enhancing bond strength at a lower bonding temperature. A further variation is the use of spin-coated layers of lower-molecular weight material. For example, a polymer of the same chemical structure but of a lower molecular weight than the substrate components can be spun onto at least one layer to be bonded, the components assembled, and the resulting stack bonded, by diffusion bonding. During thermal diffusion bonding, the low-molecular weight components can pass through their glass transition temperature at a lower temperature than the components and diffuse into the substrate plastic.

Adhesives and epoxies can be used to bond dissimilar materials and are likely to be used when bonding components fabricated in different ways. Adhesive films can be die cut and placed on components. Liquid adhesive may also be applied through spin-coating. Inking of adhesive onto structured parts (such as in nanocontact printing) can be successfully used to apply adhesive to structured surfaces without a need to "direct" the adhesive onto particular areas.

Figure 6:
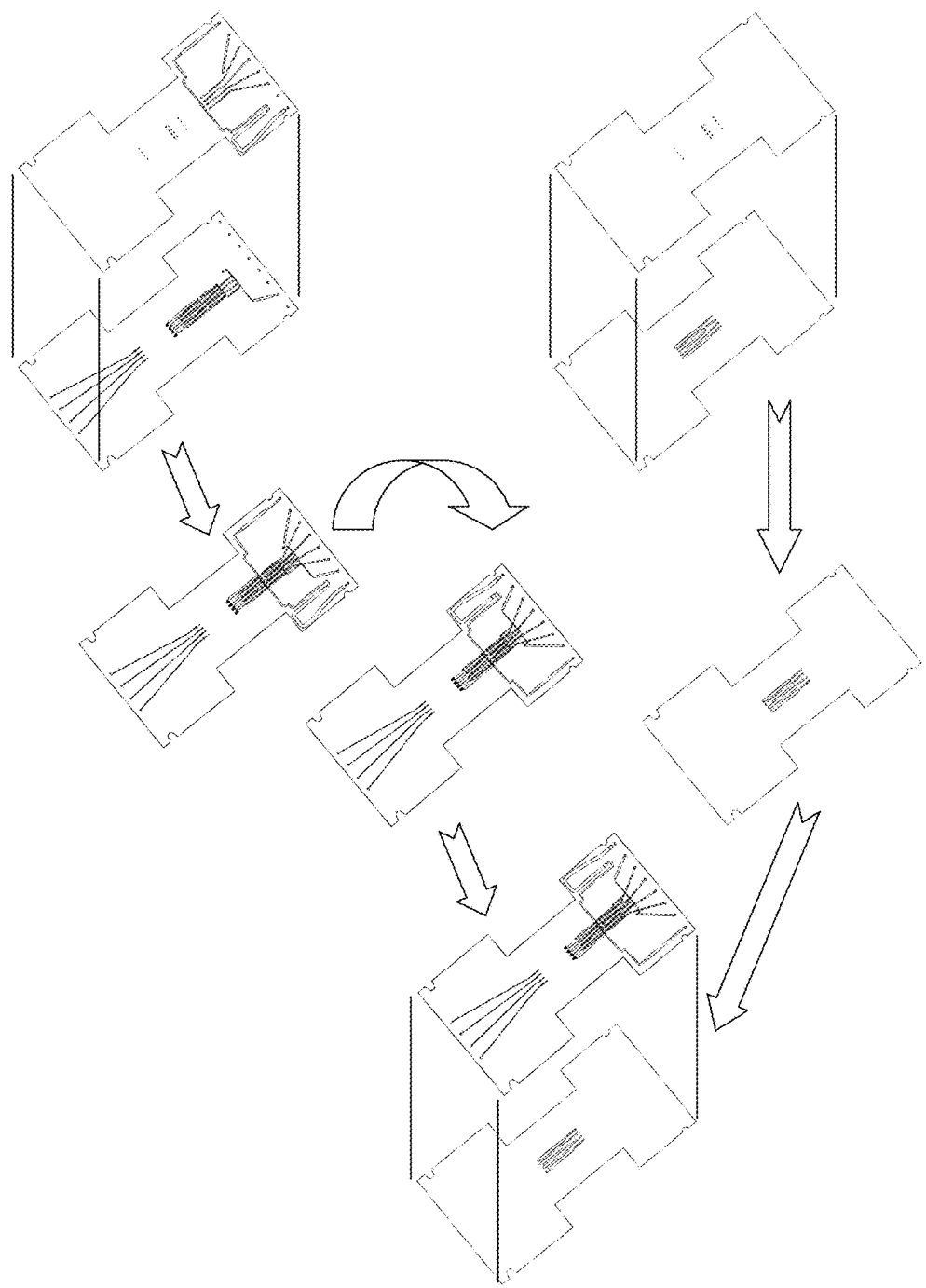
FIG. 6 is an illustration of an embodiment of assembly and bonding of the biochip of FIG. 1.

In one example, a biochip of the invention can be assembled as shown in FIG. 6. Layers 1 and 2 can be aligned by included features (e.g., pins and sockets); separately, layers 3 and 4 can be similarly aligned by included features. The layer 1 plus layer 2 stack can be inverted and applied to the layer 3 plus layer 4 stack and then entire stack can be bonded.

E. Examples

Example 1

Integrated Biochip for Nucleic Acid Extraction and Amplification

An integrated biochip for DNA extraction and amplification by PCR is shown in FIG. 1. This 4-sample device integrates the functions of reagent distribution and metering; mixing of reagents with samples; delivery of samples to a thermal cycling portion of the chip; and thermal cycling. The same biochip is used in Example 2 below and has additional structures for performance of cycle sequencing.

The biochip was constructed of 4 layers of thermoplastic as shown in FIGS. 2-5. The 4 layers are machined PMMA and have thicknesses of the layers are 0.76 mm, 1.9 mm, 0.38 mm, and 0.76 mm, respectively, and the lateral size of the biochip was 124 mm×60 mm. In general, biochips of at three or more layers allow the use of an indefinite number of common reagents to be divided among multiple assays: two fluidic layers and one layer that at least contains through-holes, enabling fluidic channels in the outer layers to 'crossover' one another. (It will be recognized that special cases exist—such as the use of only one common reagent among multiple samples—that do not necessitate a three-layer construction.) The choice of 4 layers was made for compatibility with construction of chips for other functions (such as ultrafiltration, Example 3) and full integration (Example 4).

The channels of the biochip were of cross-sectional dimensions ranging from 127 µm×127 µm to 400 µm×400 µm, while reservoirs ranged from 400 µm×400 µm in cross-section to 1.9×1.6 mm; both channels and reservoirs extend for distances as short as 0.5 mm to several 10s of mm. The capillary valves used in the biochip were of 127 µm×127 µm size for "in-plane" valves and 100 µm in diameter for through-hole capillary valves.

Certain channels, reservoirs, and capillary valves of the four machined layers were treated with a hydrophobic/oleophobic material, PFC 502A (Cytonix, Beltsville, Md.). Surface treatment was performed by coating with a wetted Q-tip followed by air-drying at room temperature. The dried fluoropolymer layer was less than 10 µm thick as determined by optical microscopy. Surface treatment serves two purposes: to prevent the formation of bubbles within liquids, especially within low-surface-tension liquids, such as cycle sequencing reagent, which can occur as the liquid rapidly wets the walls of channels or chambers (and "closes off" a bubble before the air can be displaced), and to enhance the capillary burst pressure at that capillary valves resist liquid flow. The regions left untreated were the thermal cycling chambers for PCR and cycle sequencing.

After surface treatment, the layers were bonded as shown in FIG. 6. Bonding was performed using thermal diffusive bonding, in that the stack of components was heated under pressure to a temperature near the glass transition temperature ($T_g$) of the plastic. A force of 45 lbs was applied over the entire 11.5 square inch biochip for 15 minutes during a thermal bonding profile consisting of a ramp from ambient temp to 130° C. in 7.5 minutes, a hold at 130° C. for 7.5 minutes, and rapid cooling to room temperature.

Pneumatic instrumentation was developed for driving fluids within the biochips of the invention. Two small peristaltic pumps provided pressure and vacuum. Positive pressure output was divided among three regulators that have the range of approximately 0.05-3 psig. The vacuum was ported to a regulator with an output vacuum of approximately (−0.1)-(−3) psig. A fourth, higher pressure was taken from a cylinder of $N_2$ to a further regulator or alternatively from a higher-capacity pump. The positive and negative pressures were applied to a series of 8 pressure-selector modules. Each module was equipped with solenoid valves that could choose an output pressure to be transmitted to the biochip from among the 5 inputs. The output pressure lines terminated on at least one pneumatic interface. This interface clamped to the chip with O-rings positioned over the chip ports on the input side of the chip (the ports along the top of the figures).

Immediately above the biochip ports were additional solenoid valves (i.e., gate valves; 8 per interface) that accept the output pressure lines from the pressure-selector modules. These valves, in close proximity, to the chip provide a low dead-volume interface (approximately 13 μL) between the pressure line and the chip. A low dead-volume interface can prevent unintentional motion of certain liquids on the biochip when pressure is applied to move other liquids (the small gas volume between the liquid plug and the closed valve determines the maximum amount the plug can move, for example, due to compression of the gas as pressure is applied). All pressure-selector valves and gate valves were operated under computer control using a script-based LabView™ program. An important feature of this system is that short pressure cycles times are possible. Some fluidic control events could be performed that required pulses of pressure as short as 30 msec and/or complex pressure profiles could be utilized where pressure could be switched from one value to another (i.e., one regulator to another) rapidly (that is, with time lags of no more than 10-20 msec).

The samples consisted of a bacterial suspension of approximately $10^6$ cells/mL of *E. coli* DH5 transformed with pGEM sequencing plasmid insert (pUC18 sequencing target). PCR reagent consisted of dNTPs KOD Taq Polymerase (Novagen, Madison, Wis.) at concentration 0.1 μM A 1.23 μL sample of the bacterial suspension was added to each of the four ports 104, each comprising through holes 202 and 336 in layers 1 and 2, respectively. The sample then resided in sample channels 303 in layer 2. Next, 10 μL of PCR reagent was added to port 105, comprising of through holes 217 and 306 in layers 1 and 2. The PCR reagent then resided in chamber 307 in layer 2 (see, FIG. 8*a*). A port for the evacuation of displaced air for the PCR reagent was port 107, comprising 109 and through-holes 203+305.

In operation, air displaced by samples and downstream processes (such as metering of reagents, mixing of fluids) was evacuated through ports on the output end of the chip, 108, comprised of through-holes 227. The final volume of the PCR reaction can be increased or decreased as desired.

The biochip was placed in the pneumatic manifold described above. The following automated pressure profile was performed with no delays between steps. Unless otherwise noted, the pneumatic interface valves, corresponding to ports along the input side of the chip, were closed during all steps.

A pressure of 0.12 psig was applied to ports 104 for 15 sec to drive the samples down channels 303 to through-hole 304. The samples passed through through-hole 304 and emerged on the other side of layer 2 in sample chamber 204 of layer 1 and were driven to the first mixing junction 205. At the first mixing junction the samples were retained by capillary valves 210 (see, FIGS. 8*b-c*).

A pressure of 0.12 psig was applied to port 105 for 10 sec to drive the PCR reagent through through-hole 320. The PCR reagent emerged on the other side of layer 2 in distribution channel 208, and moved into the metering chambers 209, which define a volume of reagent equal to the sample volume, where they were retained by capillary valves 211 at mixing junction 205. (see, FIG. 8*d*).

Figure 8:
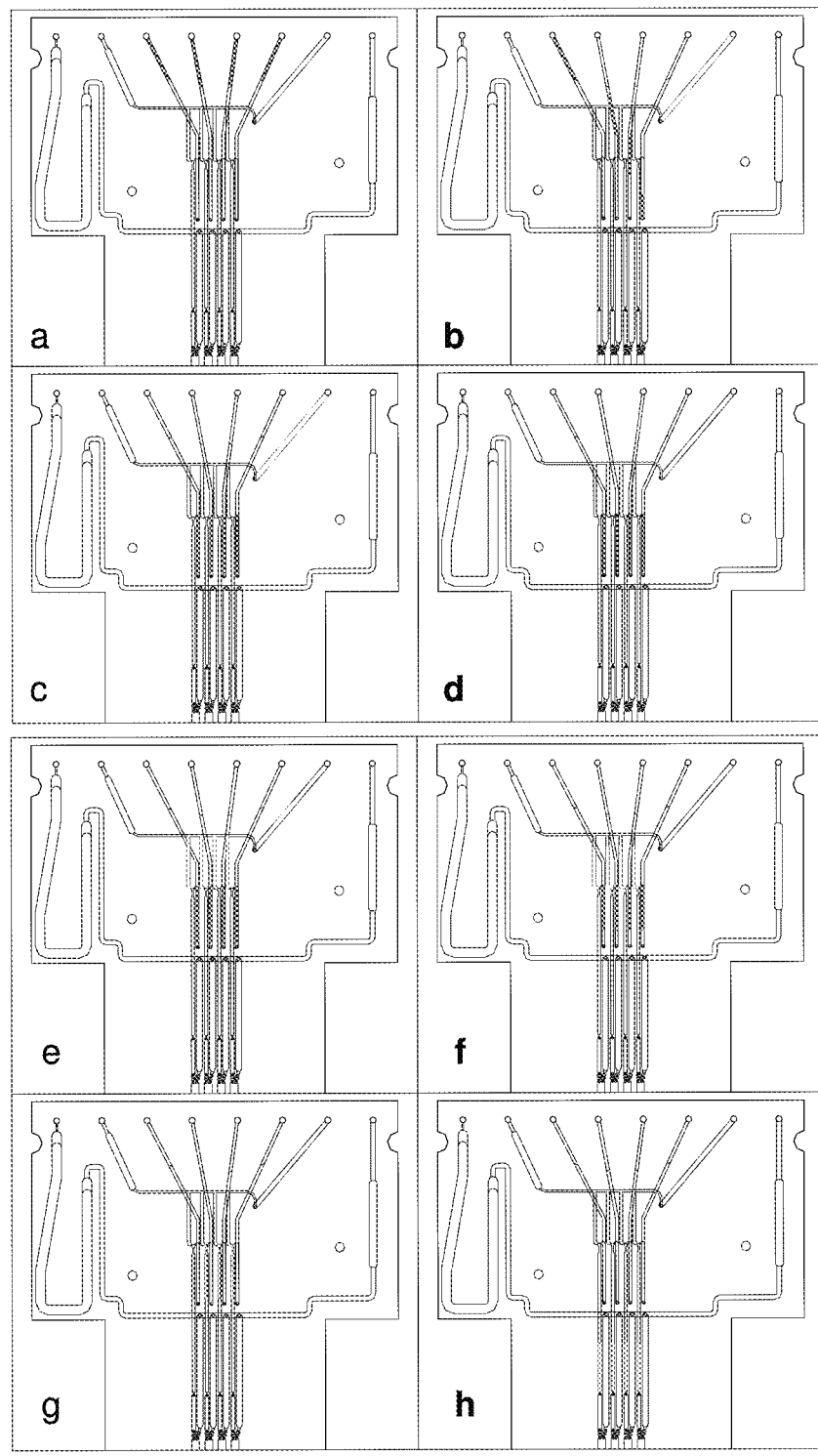
FIG. 8 is an illustration showing an embodiment of fluidic steps of the biochip of FIG. 1 for template amplification by PCR.
Figure 8:
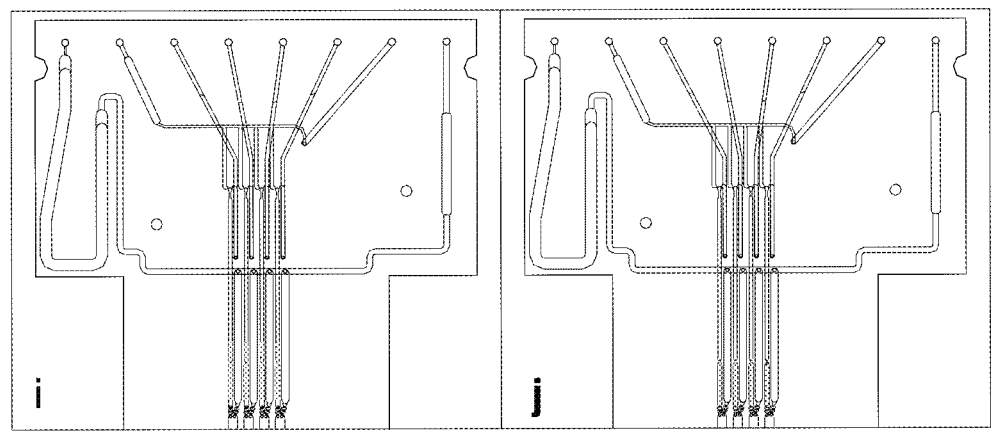
Figure 8A:
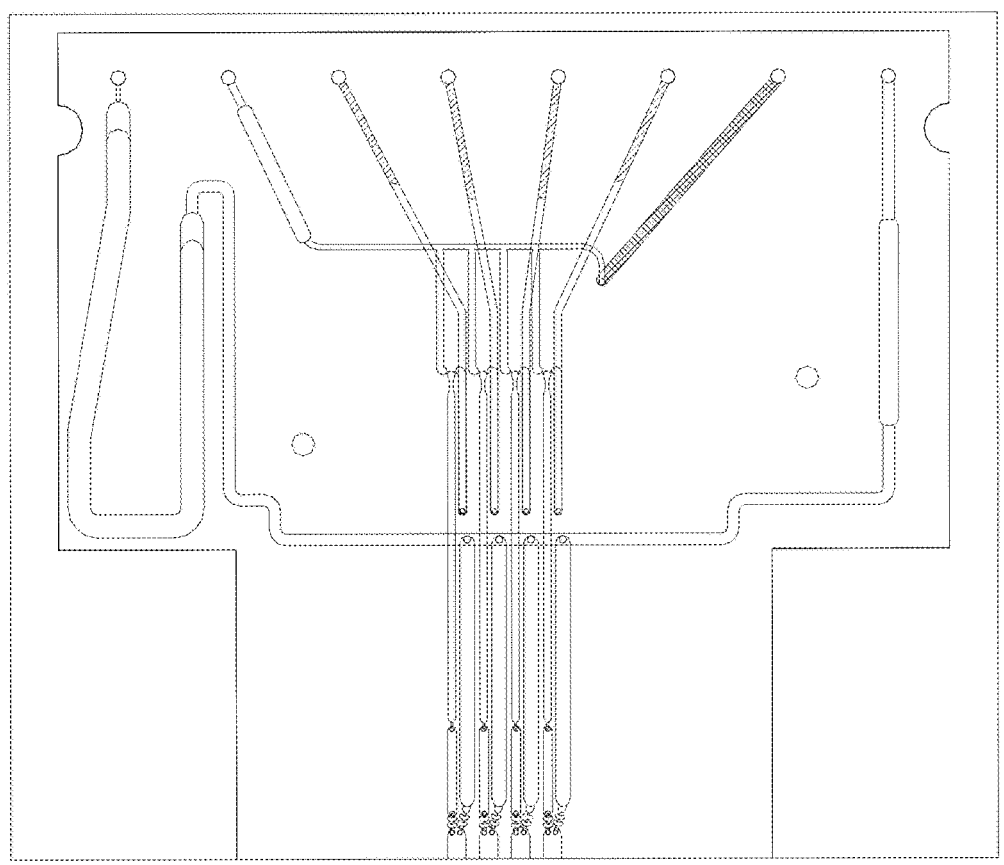
FIG. 8*a* is an illustration showing samples and PCR reagents have been loaded into a biochip of the invention.
Figure 8B:
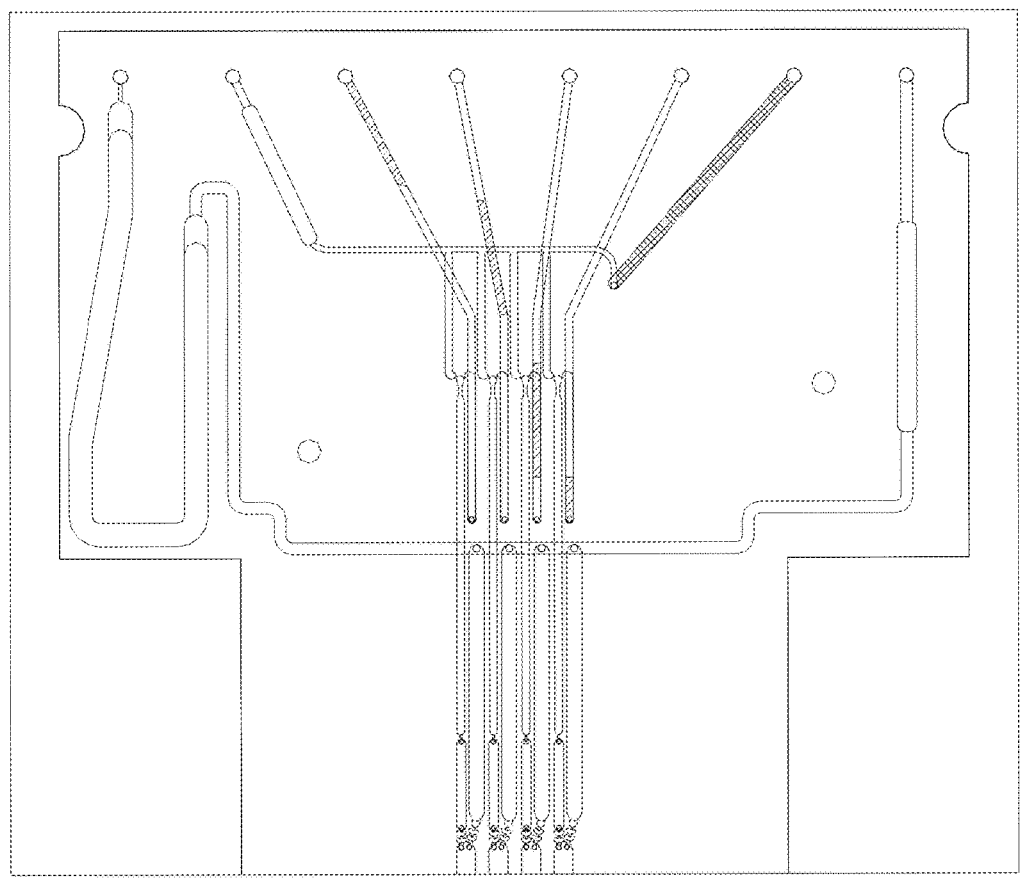
FIG. 8*b* is an illustration showing sample delivery through channels to sample chambers (they are shown at different positions along the sample channels in order to illustrate the flow path.)
Figure 8C:
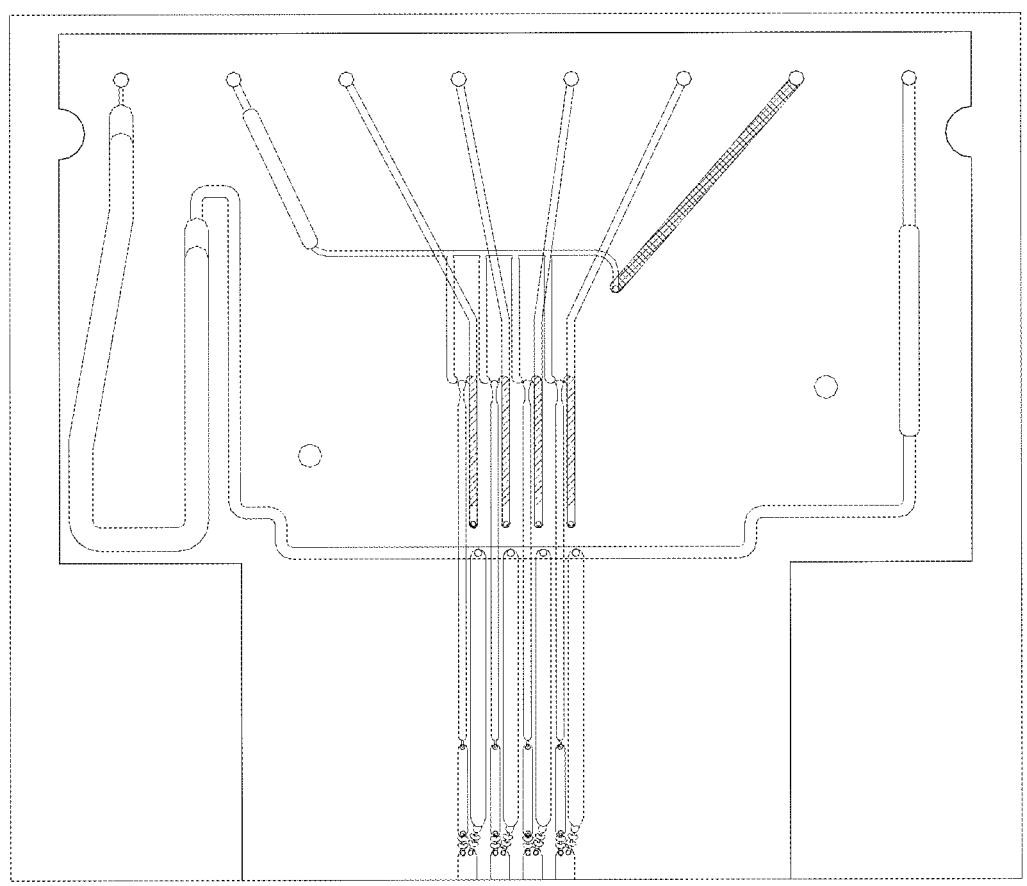
FIG. 8*c* is an illustration showing the samples in the sample chambers.
Figure 8D:
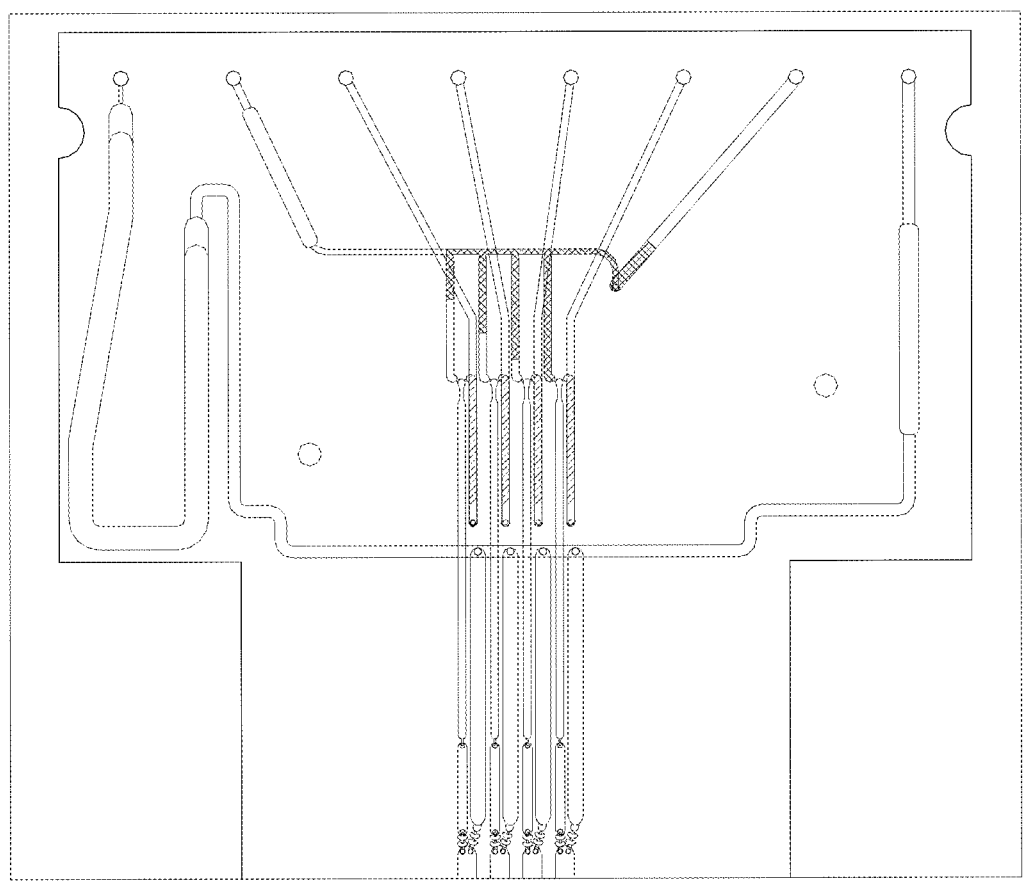
FIG. 8*d* is an illustration showing delivery of PCR reagents to reagent chambers.
Figure 8E:
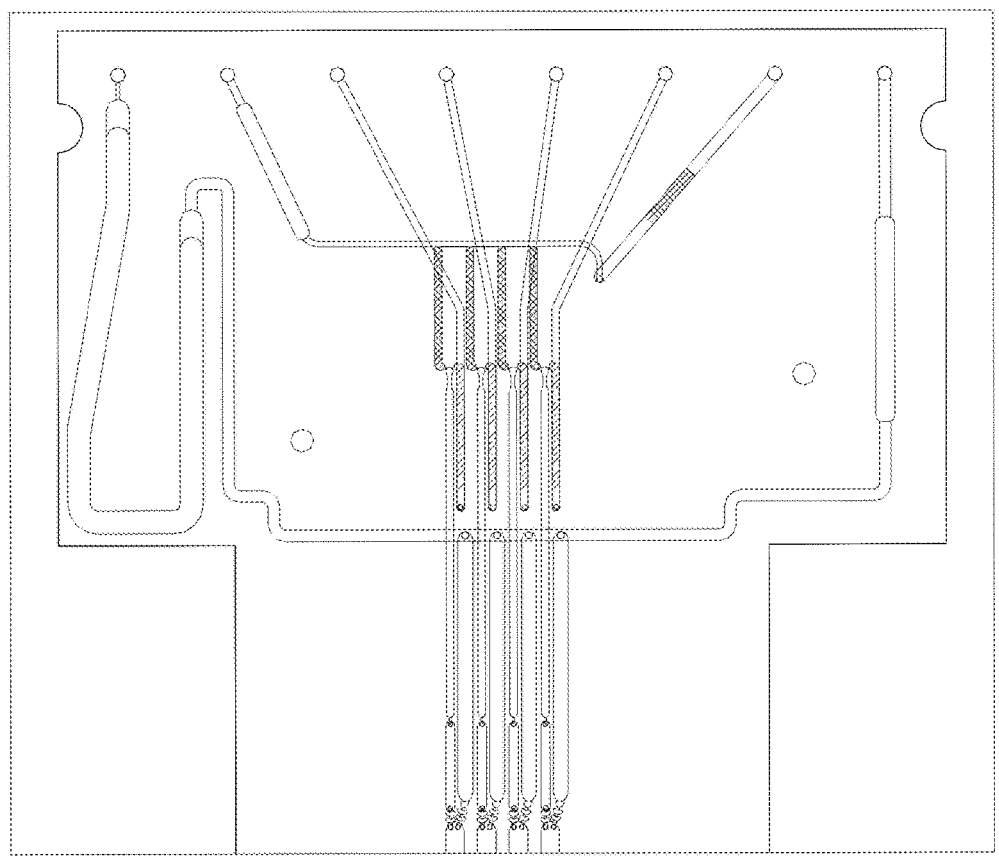
FIG. 8*e* is an illustration showing withdrawal of excess PCR reagent.

A pressure of 0.12 psig was applied to port 107 (comprised of through-holes 203 and 305) with port 105 open to atmosphere for 3 sec to empty channel 208 (see, FIG. 8*e*).

Figure 8F:
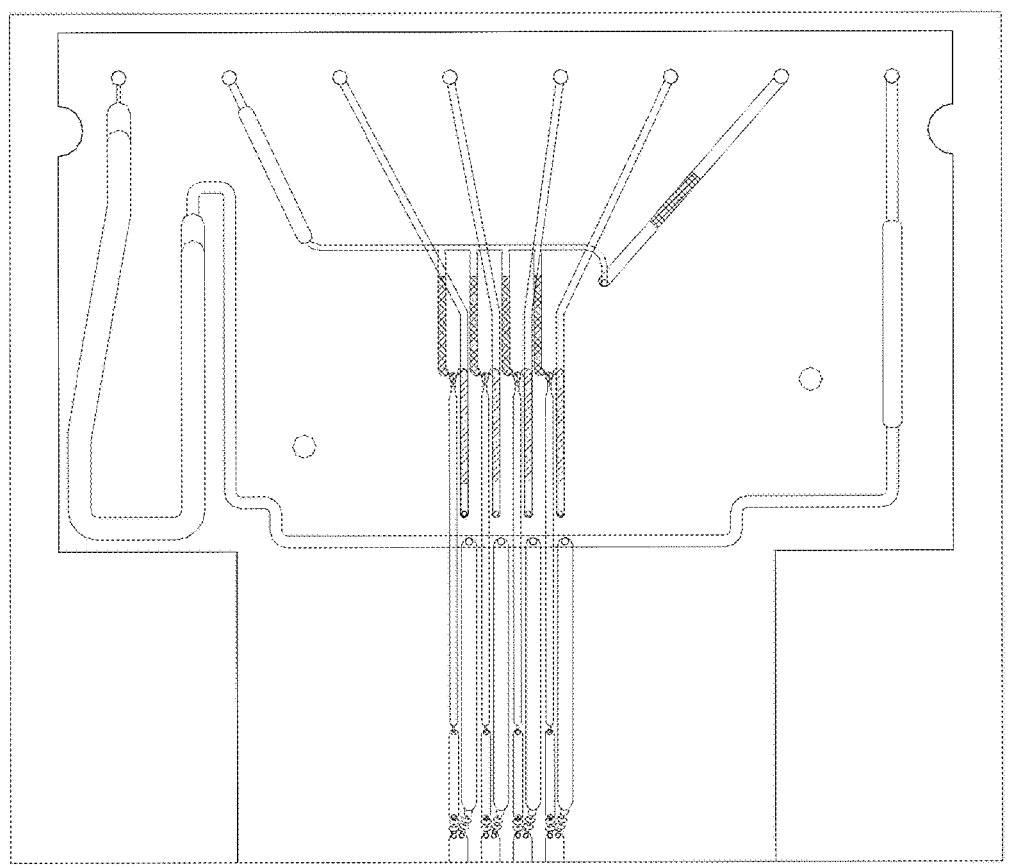
FIGS. 8*f* and 8*g* are illustrations showing the initial mixing step and retention of the liquids by the first set of capillary valves.

A pressure of 0.8 psig was applied to ports 107 and 105 for 0.03 sec and a pressure of 0.7 psig was simultaneously applied to ports 104 for 0.03 sec to initiate mixing of the samples and PCR reagents by bursting liquids past the capillary valves 210 and 211 (see, FIG. 8*f*).

A pressure of 0.12 psig was applied to ports 104 and 107 for 10 sec to pump the samples and PCR reagents into mixing channels 214, with retention at capillary valves 210 and 211. Passage through the mixing bulbs 212 into the constrictions 213 created added hydraulic resistance to flow, decreasing the high velocity imparted by the previous high pressure pulse.

Figure 8G:
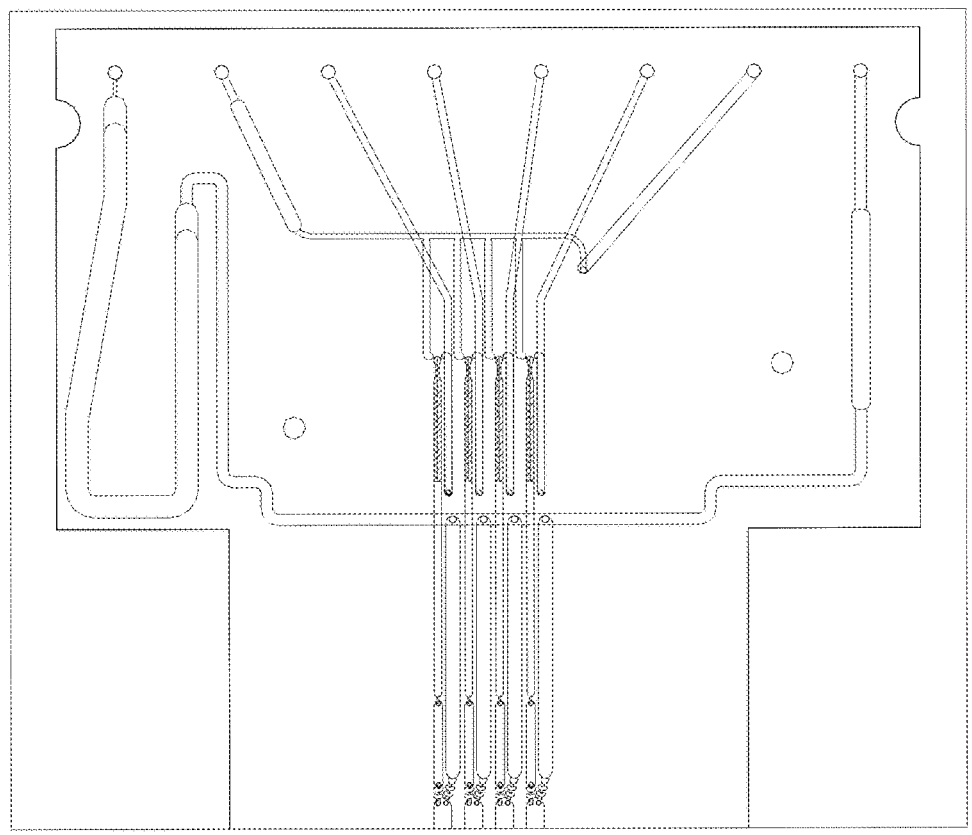

A pressure of 0.7 psig was applied to ports 104 and 107 for 0.03 sec to detach the liquid from capillary valves 210 and 211 (see FIG. 8*g*).

Figure 8H:
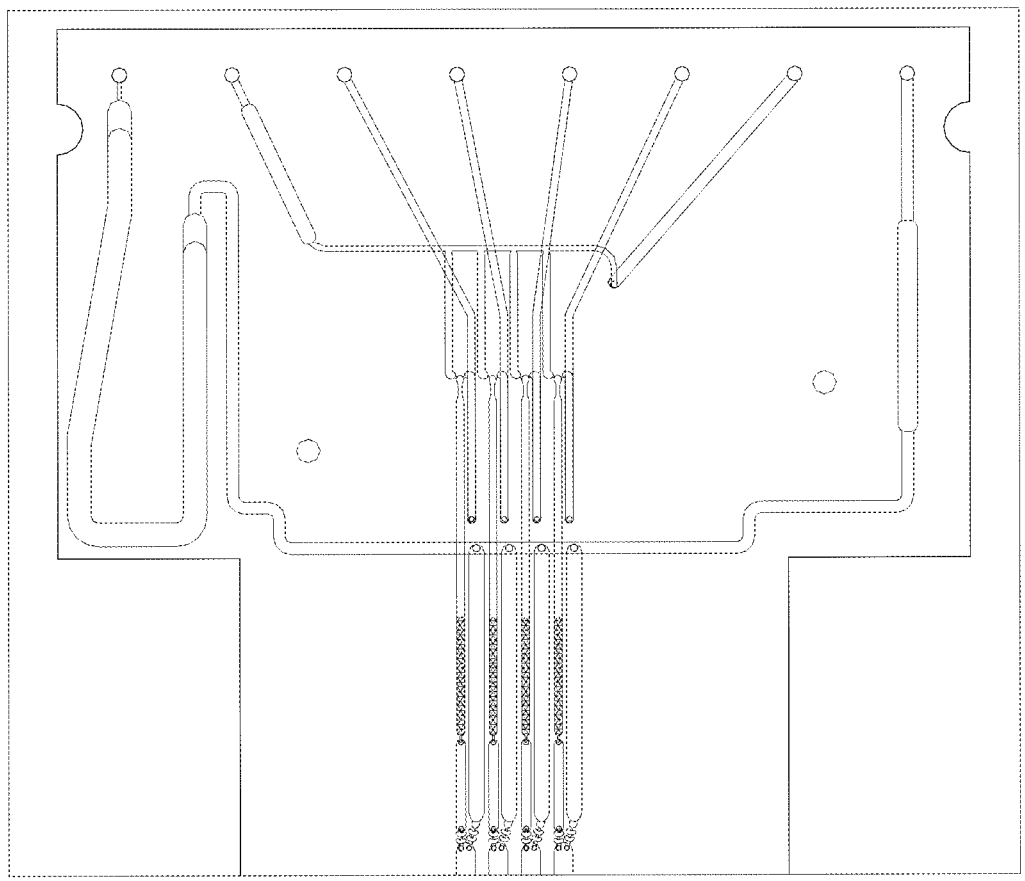
Figure 81:
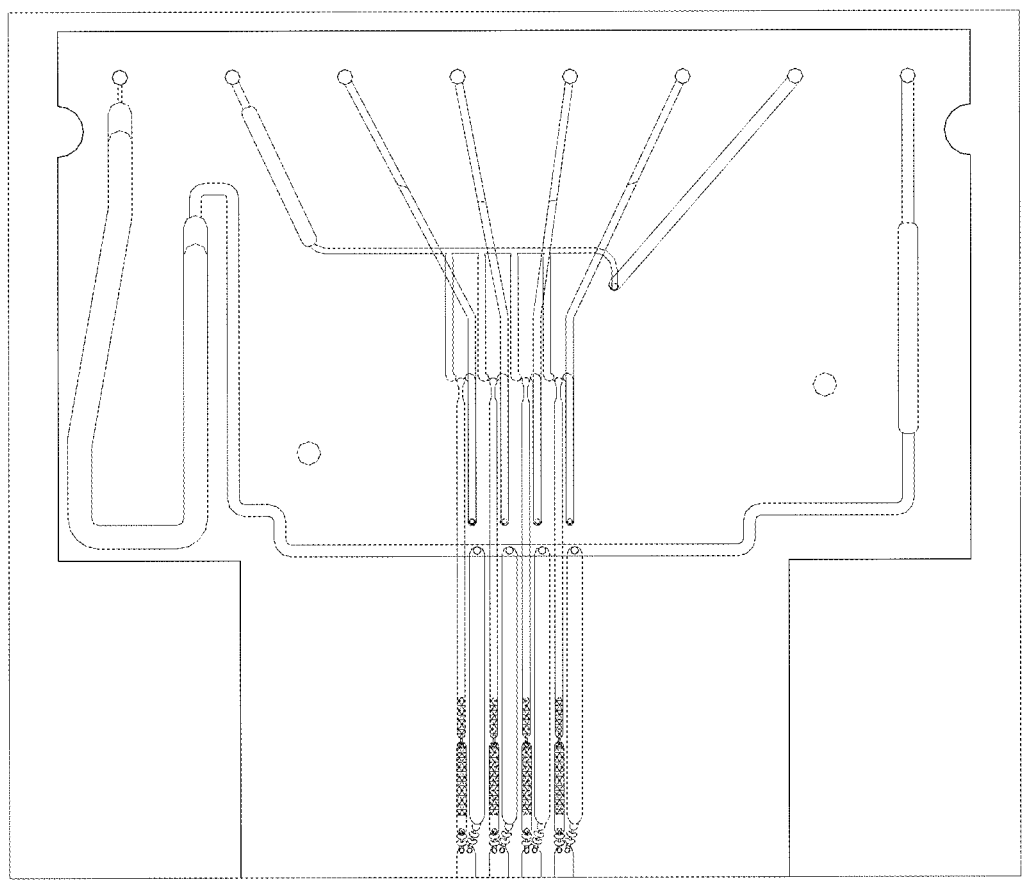

A pressure of 0.12 psig was applied for 3 sec to ports 104 and 107 to pump liquid through mixing channel 214 to capillary valves 219, where they were retained, (see, FIG. 8*h*).

A pressure of 0.7 was psig applied for 0.1 sec to ports 104 and 107 to drive the mixture of the samples and PCR reagents through through-holes 315 and 402 and through the body of layers 2 and 3, and into PCR chamber 502 (see, FIG. 8*i*).

Figure 8J:
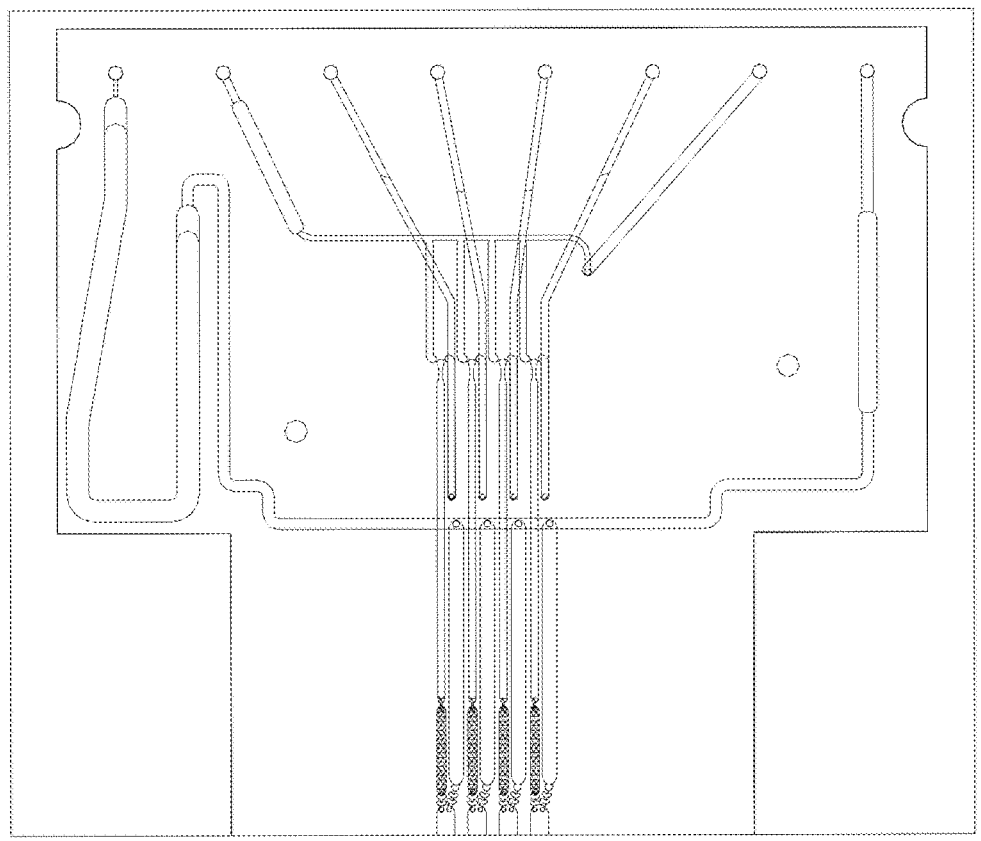

A pressure of 0.12 psig was applied for 3 sec to ports 104 and 107 to complete pumping of the mixture of the samples and PCR reagents into chamber 502. The leading edge of the mixture of the samples and PCR reagents then passed through through-holes 403 and 316, emerged into layer 1, and was pinned at capillary valve 220 (see, FIG. 8*j*).

The biochip was then pressurized to 30 psig $N_2$ and thermally cycled for PCR amplification via a Peltier using a gas bladder compression mechanism as described the U.S. patent application entitled, "METHODS FOR RAPID MULTIPLEXED AMPLIFICATION OF TARGET NUCLEIC ACIDS", U.S. Ser. No. 12/080,746, filed on Apr. 4, 2008; and in International Patent Application Serial No. PCT/US08/53234, filed 6 Feb. 2008 and entitled, "DEVICES AND METHODS FOR THE PERFORMANCE OF MINIATURIZED IN VITRO ASSAYS," each of which are hereby incorporated by reference in their entirety.

Sample, reagent volumes, and PCR chamber sizes were chosen such that the liquid filled the region between valves 219 and valves 220. As a result there liquid/vapor interfaces of small cross sectional area (typically 127 μm×127 μm) were located approximately 3 mm from the thermally cycled bottom surface of layer 4. The application of pressure during thermal cycling inhibited outgassing by dissolved oxygen in the sample. The small cross-sectional area of the liquid/vapor interface and distance from the Peltier surface both inhibited evaporation.

The observed temperature at the top of the biochip during cycling never exceeded 60° C., and, as a result, the vapor pressure at the liquid/vapor interfaces was significantly lower than it would have been for such interfaces if they were within the PCR chamber. For a 2 μL sample, 1.4 μL of which is within chamber 502 and the remainder is within the through-holes and capillary valves, the observed evaporation was less than 0.2 μL over 40 cycles of PCR. The volume of non-cycled fluid—0.6 μL in this case—can be reduced by the choice of smaller diameters for the through-holes.

PCR was performed using the following temperature profile:
Heat lysis of bacteria for 3 min at 98° C.
40 cycles of the following
Denaturation at 98° C. for 5 sec
Annealing at 65° C. for 15 sec
Extension at 72° C. for 4 sec
Final extension at 72° C./2 min The PCR product was retrieved by flushing the chamber 502 with ~50 μL deionized water and analyzed by slab gel electrophoresis. PCR yield was up to 40 ng per reaction, much more than required for subsequent sequencing reactions. In this application, bacterial nucleic acids were generated merely by lysing bacteria. Nucleic acids can be subjected to purification as required, a process that can improve the efficiency of amplification, sequencing, and other reactions.

Example 2

Figure 9:
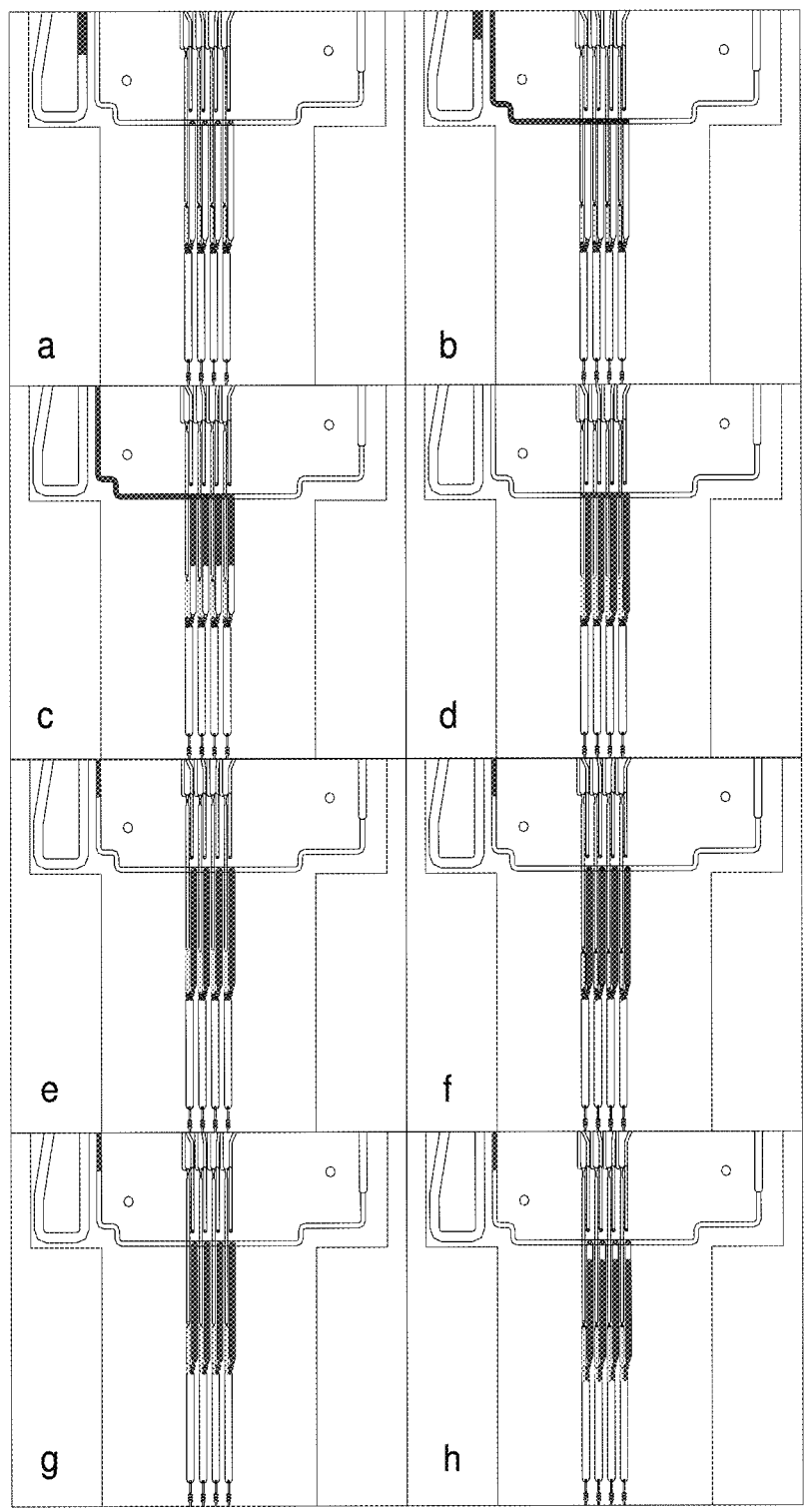
FIG. 9 is an illustration showing an embodiment of the fluidic steps of an integrated biochip.
Figure 9:
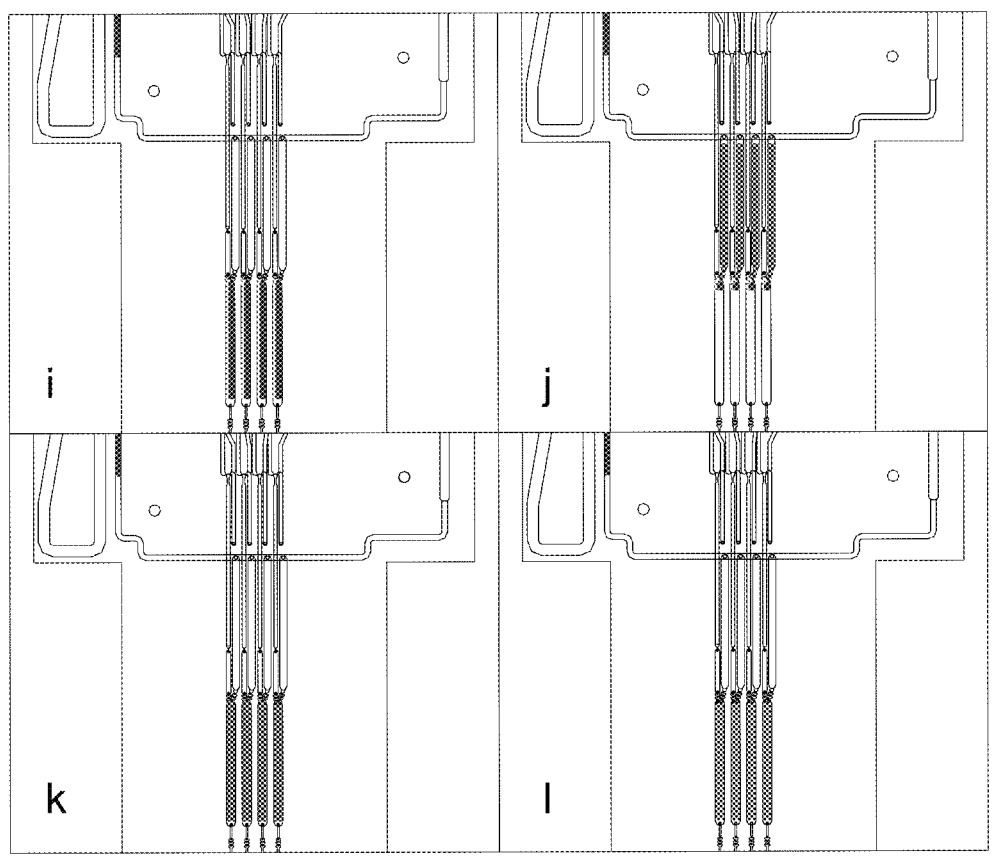
Figure 9A:
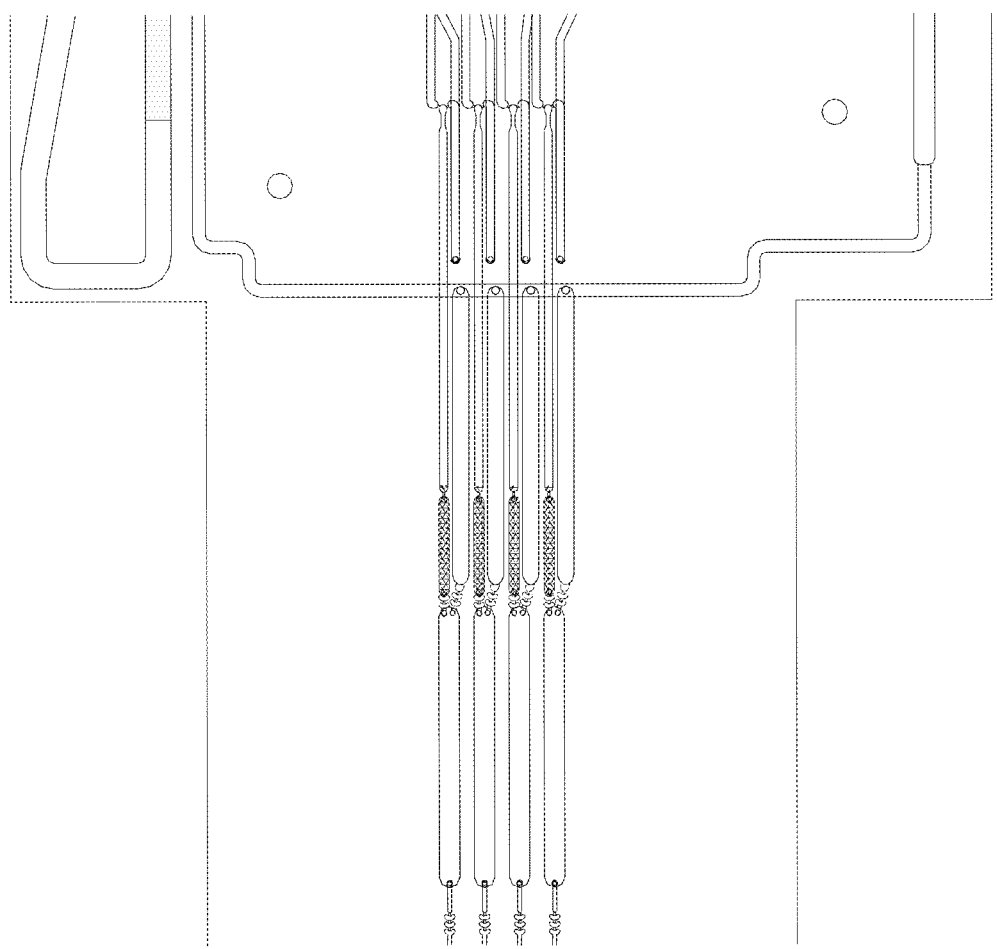
FIGS. 9*a* through 9*e* are illustrations showing the delivery of cycle sequencing reagent to metering chambers in layer 1 and removal of excess reagent from the vicinity of the chambers.

Integrated Biochip for Distribution of Cycle Sequencing Reagent, Mixing with PCR Product, and Cycle Sequencing The biochips described in Example 1 were used. PCR product generated in tubes using the protocol outlined in Example 1 was added to both sample and PCR reagent ports of the biochip as described above. 50 μL of a cycle sequencing reagent (BigDye™ 3.1/BDX64, MCLab, San Francisco) was added to port 106 (comprised of through-holes 215 and 308) and chamber 309. After installation of two pneumatic interfaces (one for the input and one for the output end of the chip), the PCR product was processed as described in Example 1 through to the PCR chamber, but without the PCR thermal cycling step. The disposition of the fluids in the chip was as shown in FIG. 9a.

Figure 9B:
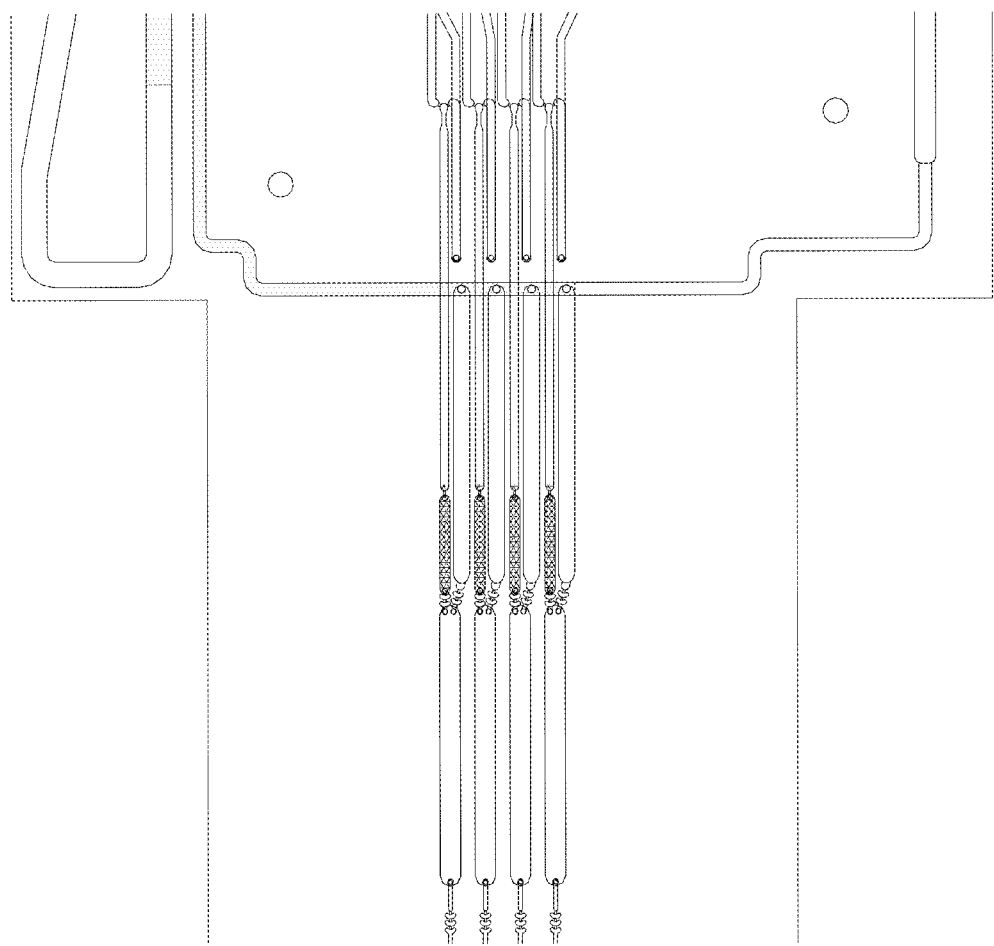

The following pressure profile was carried out using the pneumatic system software; all solenoid valves corresponding to chip ports were closed unless otherwise noted:

1. A pressure of 0.1 psig was applied to port 106 with ports 109 open to atmosphere for 10 sec to pump cycle sequencing reagent into channel 310 (see, FIG. 9b).

Figure 9C:
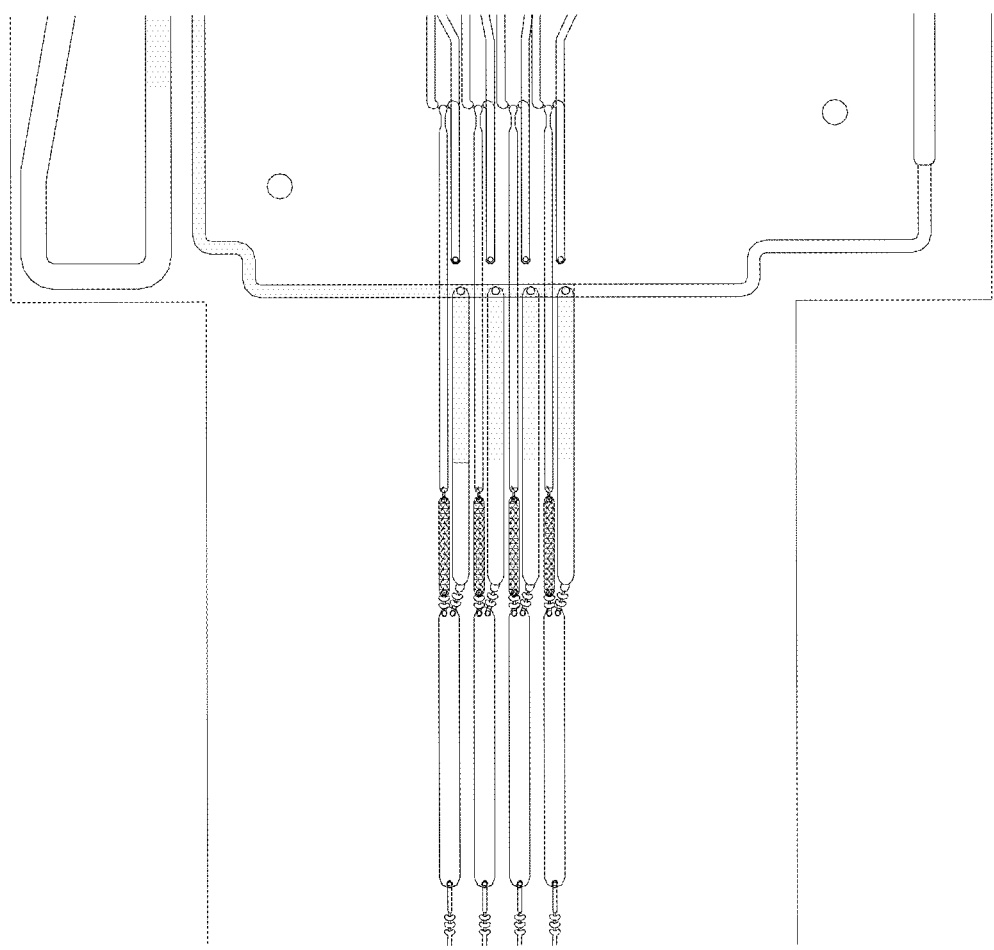

2. A pressure of 0.7 psig was applied for 0.2 sec on ports 106 and 108 (comprised of through-holes 216 and 314) to drive cycle the sequencing reagent from channel 304 through through-holes 311, through the body of layer 2, and into in the cycle sequencing reagent metering chambers 218 on layer 1 (see, FIG. 9c).

Figure 9D:
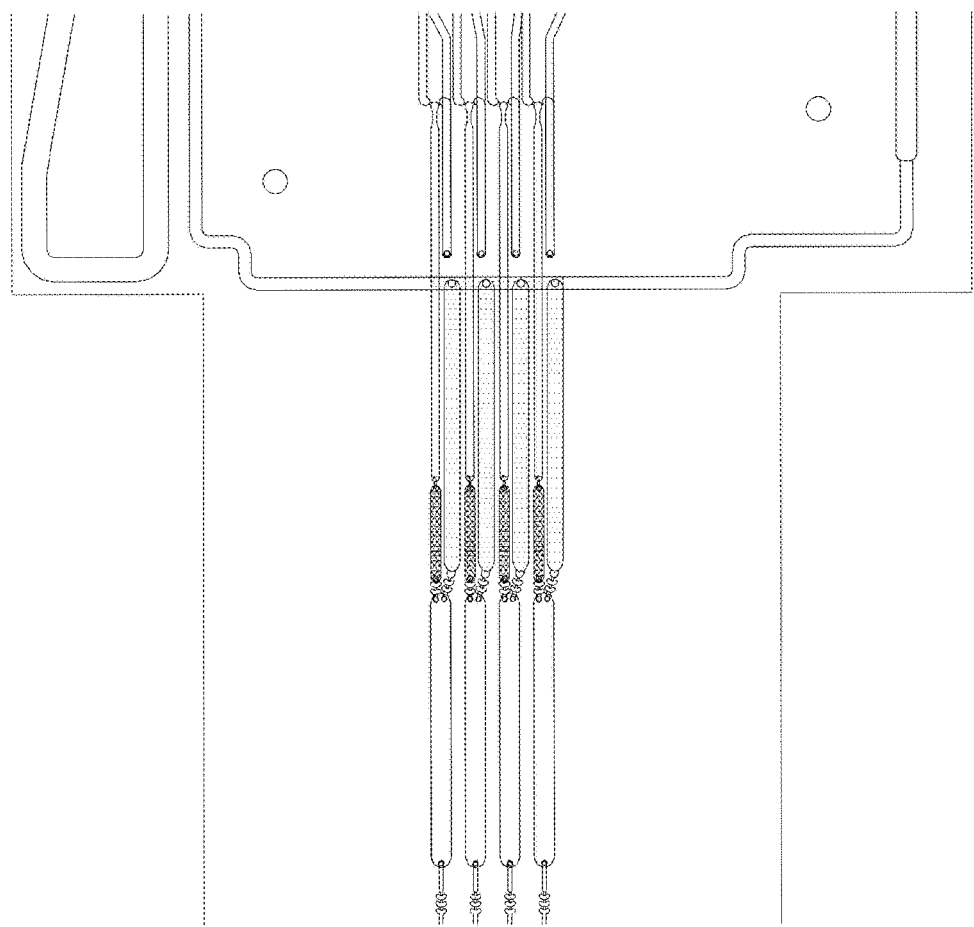

3. A pressure of 0.1 psig was applied to port 106 with ports 109 open to atmosphere, driving the cycle sequencing reagent to the capillary valves 221, where it was retained (see, FIG. 9d).

Figure 9E:
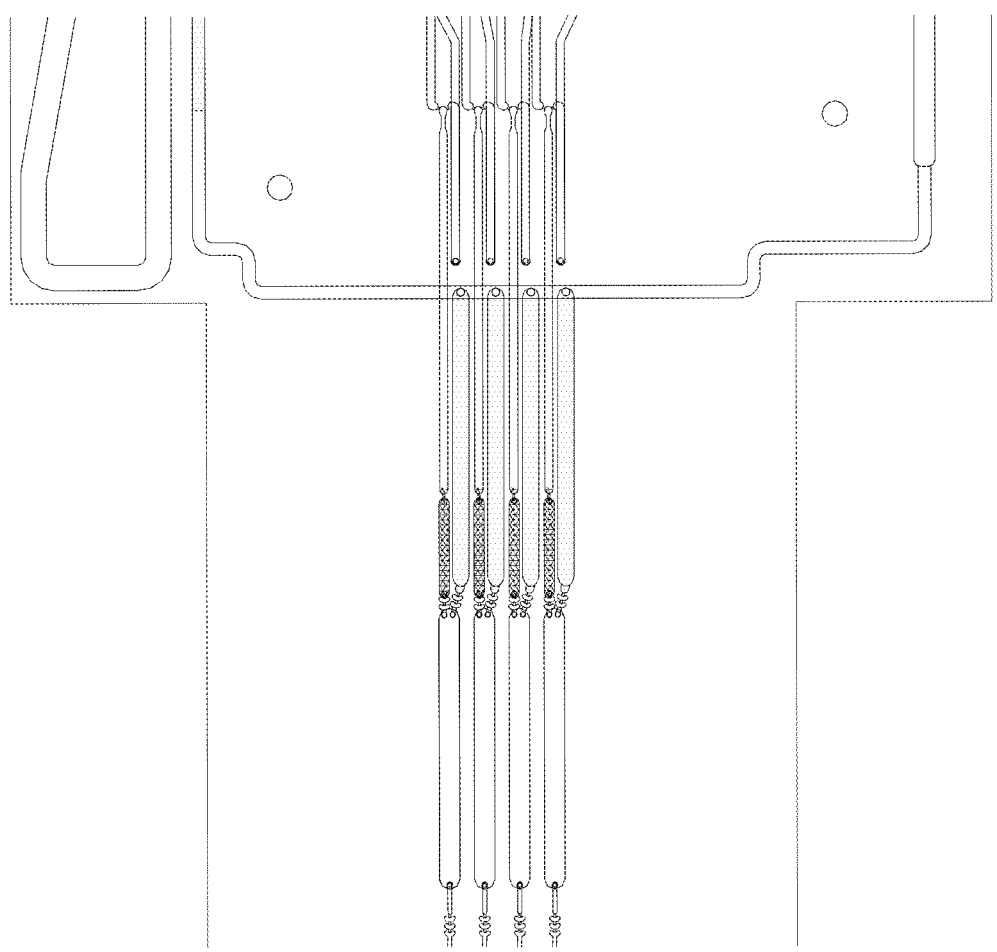

4. A pressure of 0.1 psig was applied to port 108 with port 106 open to atmosphere for 1 sec to drive excess cycle sequencing reagent backwards into chamber 101, leaving channel 310 empty (see, FIG. 9e).

Figure 9F:
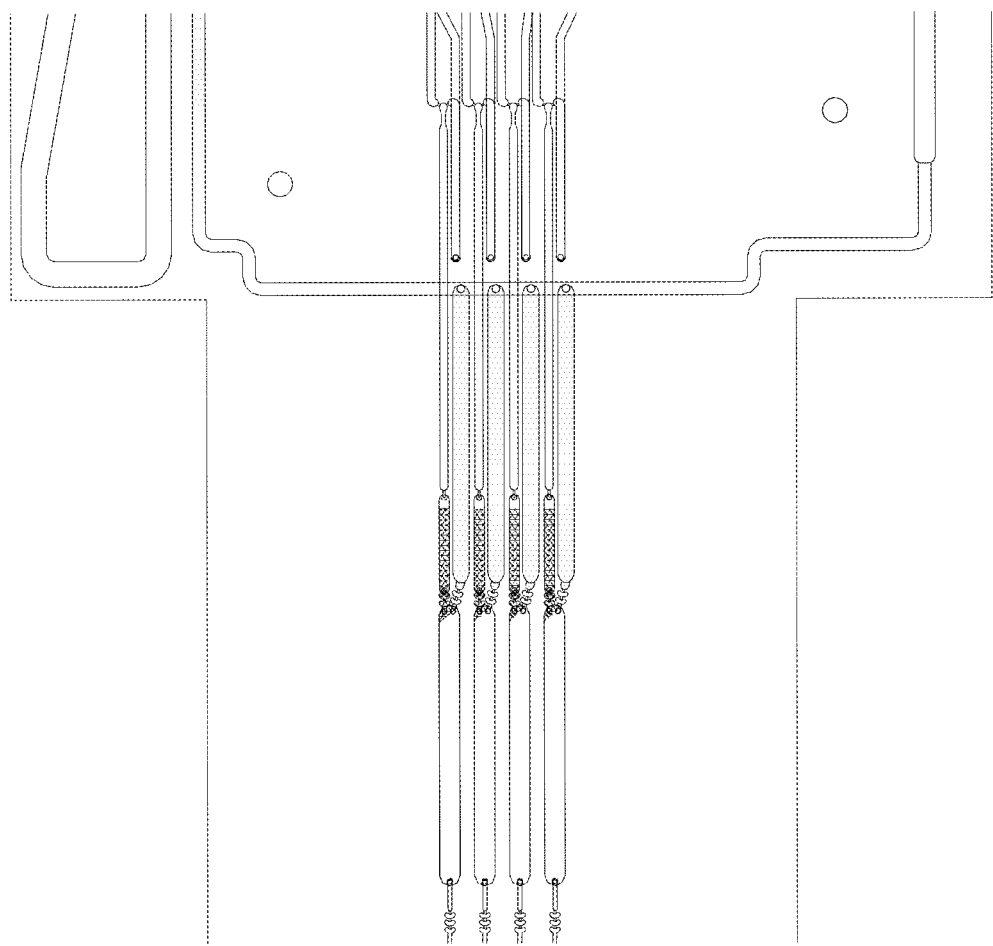
FIGS. 9*f* and 9*g* are illustrations showing the introduction of PCR product into a Sanger reaction chamber.

5. A pressure of 0.7 psig was applied to ports 104 and 107 for 0.1 sec with ports 109 open to atmosphere to drive PCR product past capillary valve 220 and into through hole 317, passing through the body of layer 2 and through-hole 404 in layer 3, and into the cycle sequencing chamber 503 of layer 4 (see, FIG. 9f).

Figure 9G:
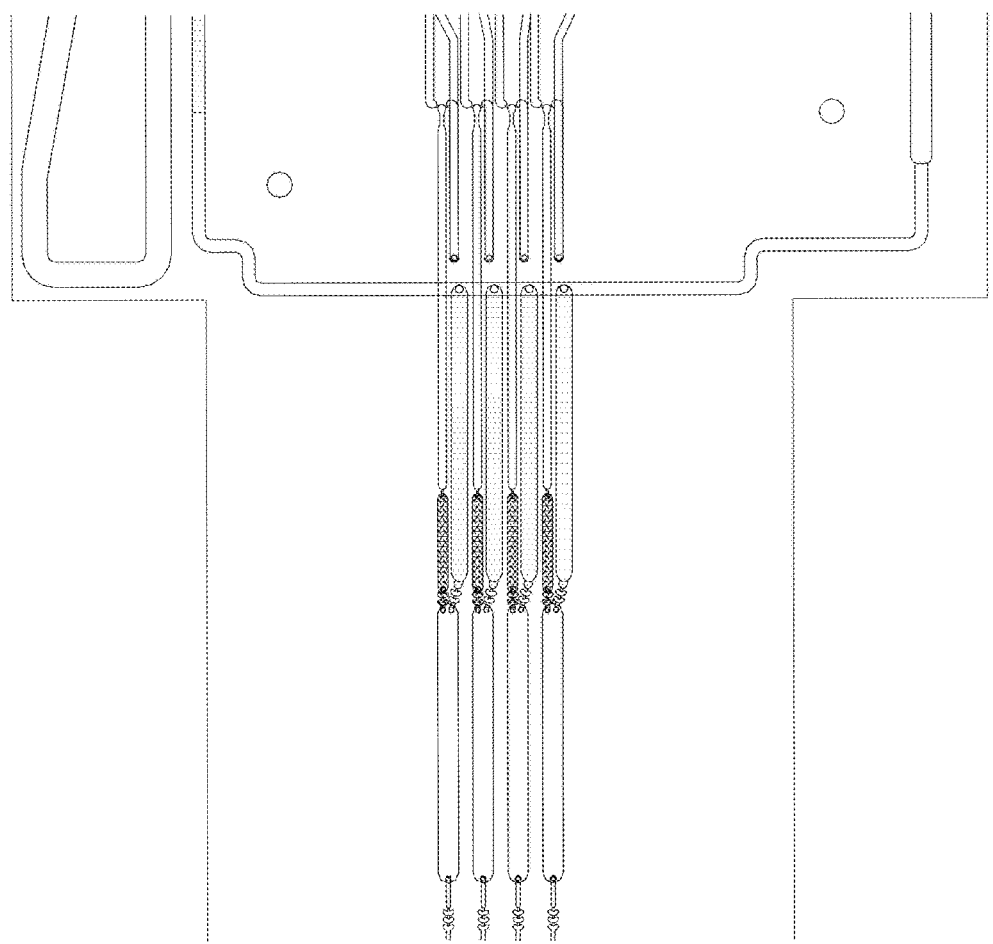

6. A pressure of 0.1 psig was applied to ports 109 with ports 104 and 107 open to atmosphere for 5 sec to drive PCR sample back to the through-holes. Capillary action retained the liquids at the entrance of the through-hole, preventing a trapped air bubble from appearing between the PCR product and chamber 503 (see, FIG. 9g).

Figure 9H:
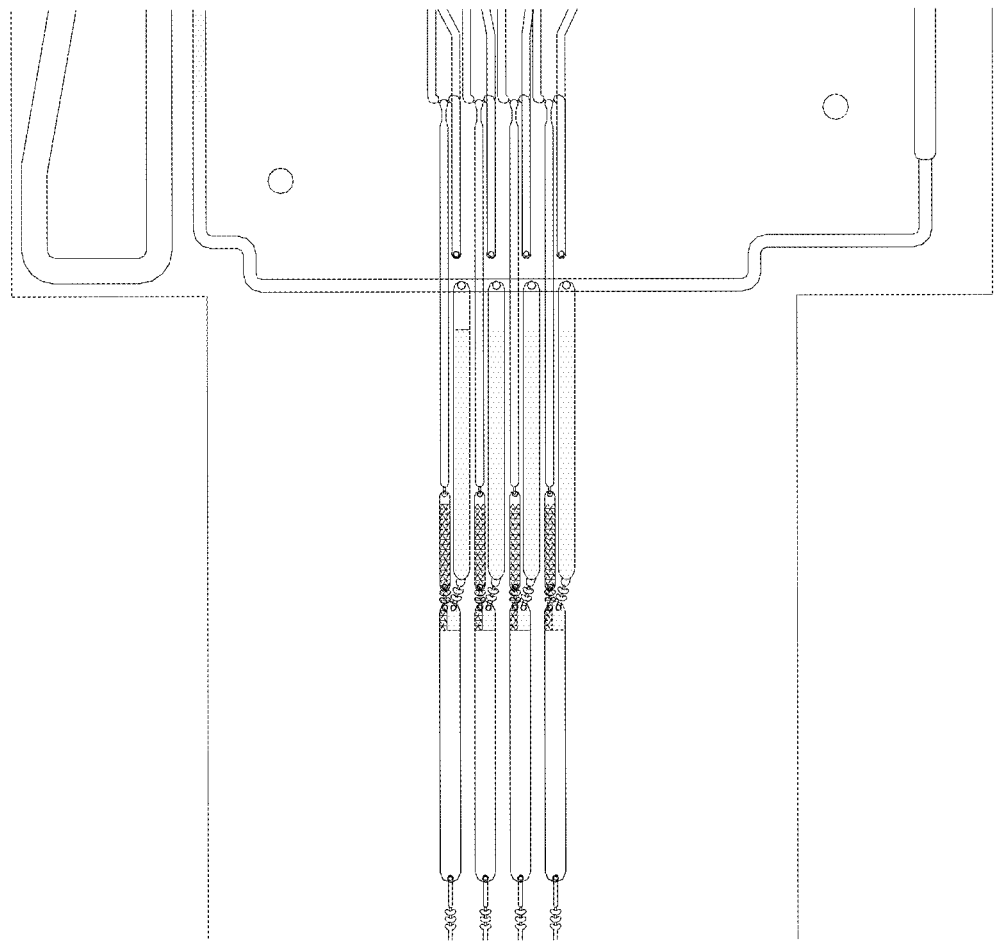
FIG. 9*h*-9*k* are illustrations showing mixing of Sanger reagent with PCR product by reciprocal motion.

7. A pressure of 0.7 psig was applied to port 108 for 0.2 sec with ports 109 open to atmosphere to drive cycle sequencing reagent into chamber 503, while simultaneously applying 0.1 psig to ports 104 and 107, to contact the PCR product with the sequencing reagent (see, FIG. 9h).

Figure 9I:
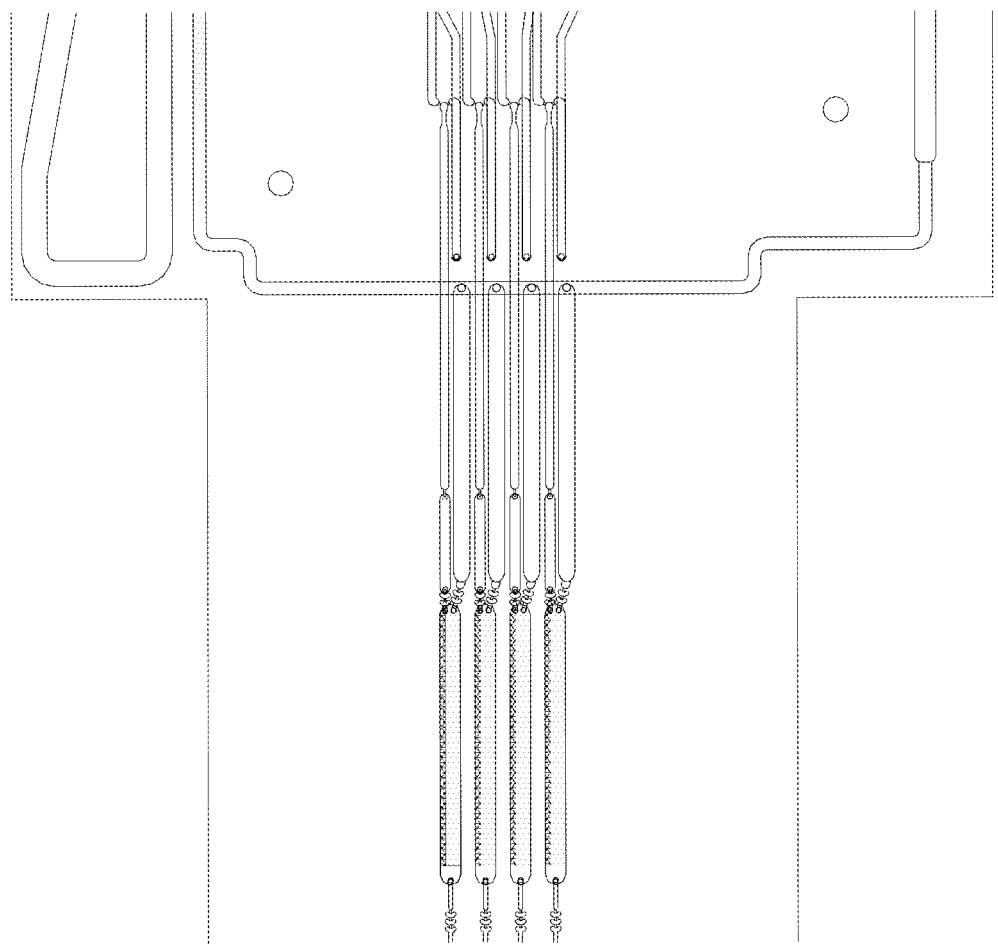

8. A pressure of 0.1 psig was applied for 10 sec to ports 104, 107 and 108 with ports 109 open to atmosphere to drive PCR product and Sanger reagent into the chamber. The trailing meniscus of the PCR product and that of the sequencing reagent were pinned at the capillary valves 220 and 221 (see, FIG. 9i).

Figure 9J:
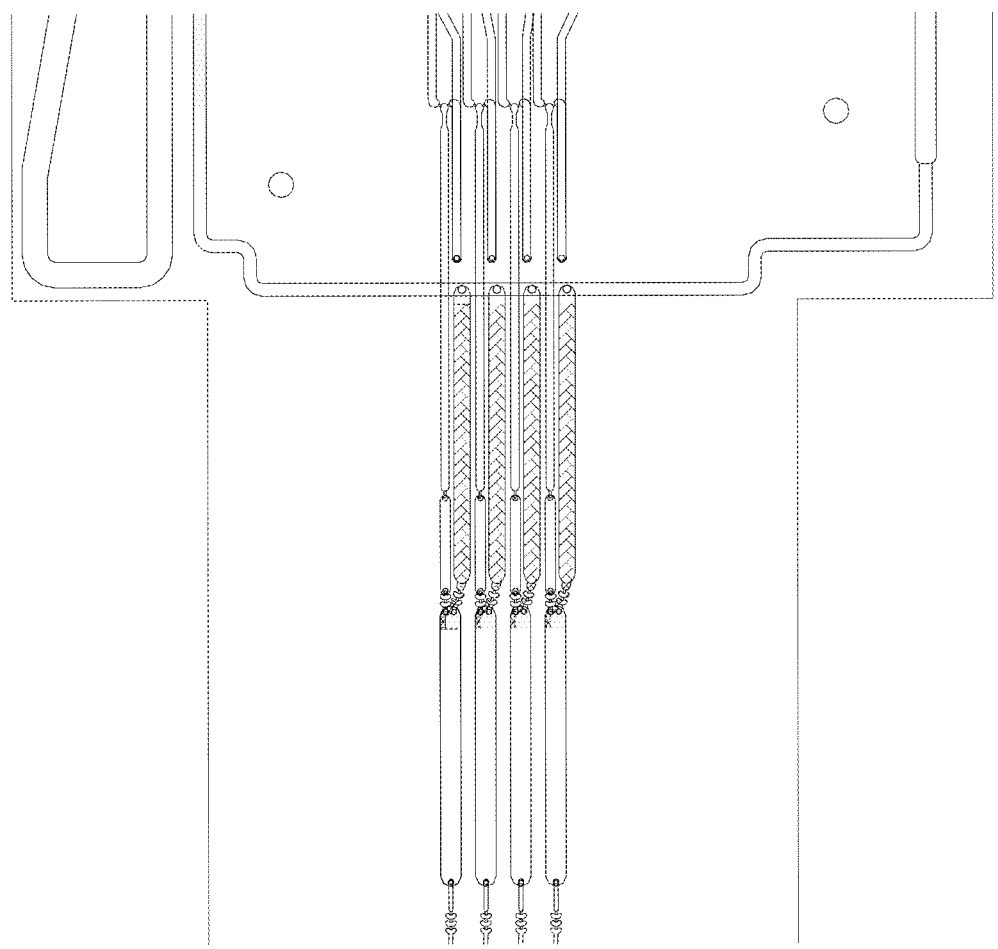

9. 5 vacuum pulses of 0.25 psig vacuum and duration 0.1 sec were applied to port 108 with ports 109 open to atmosphere to draw both liquids partially backwards into reagent metering chamber 218 (see, FIG. 9j).

Figure 9K:
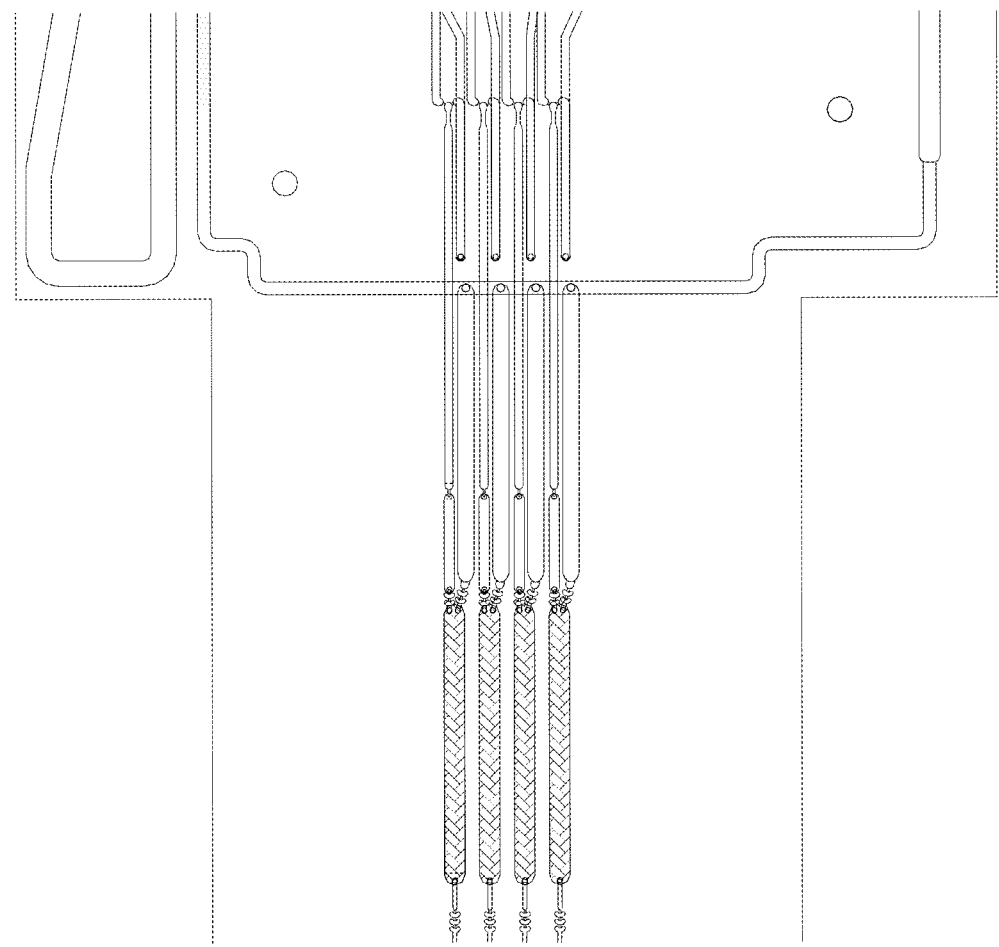

10. A pressure of 0.1 psig was applied to ports 104, 107, and 108 with ports 109 open to atmosphere for 10 sec to pump the mixture back into chamber 503, with the trailing meniscus being pinned at capillary valves as in step 8. (see, FIG. 9k).

Steps 9-10 were repeated an additional two times to effect mixing of the sequencing reagent and PCR product.

Figure 9L:
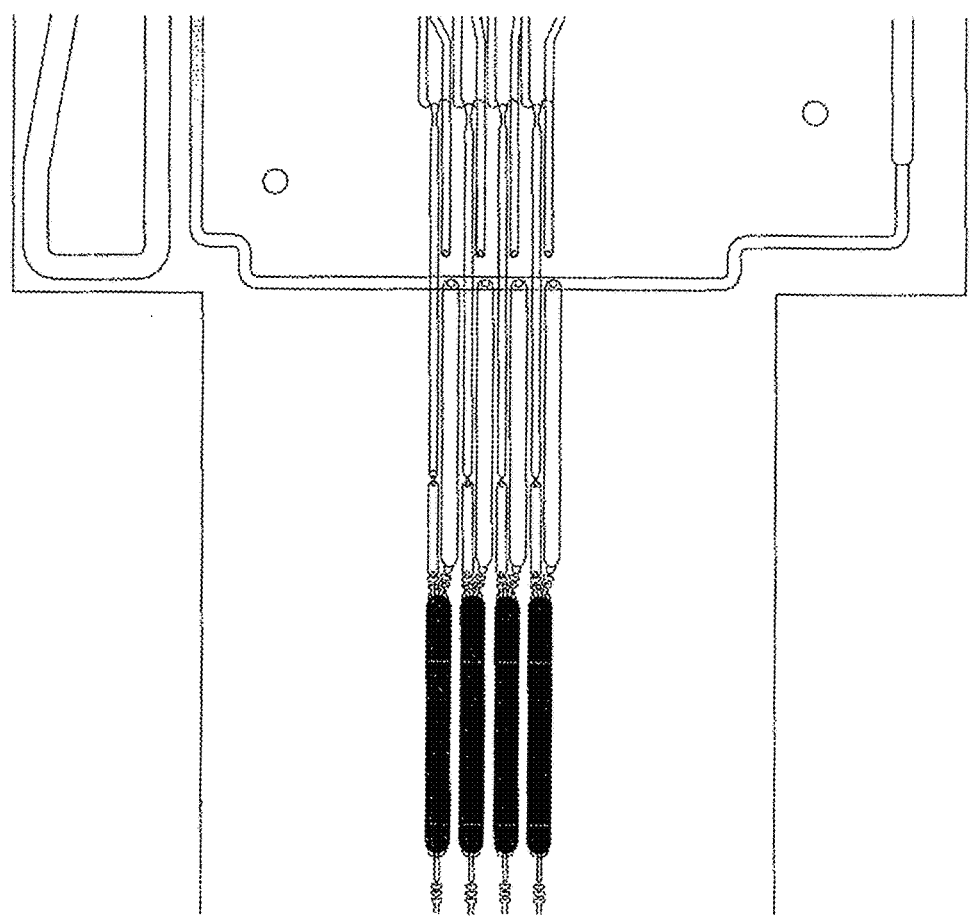
FIG. 9*l* is an illustration showing cycled product in that can be removed for analysis.
Figure 10A:
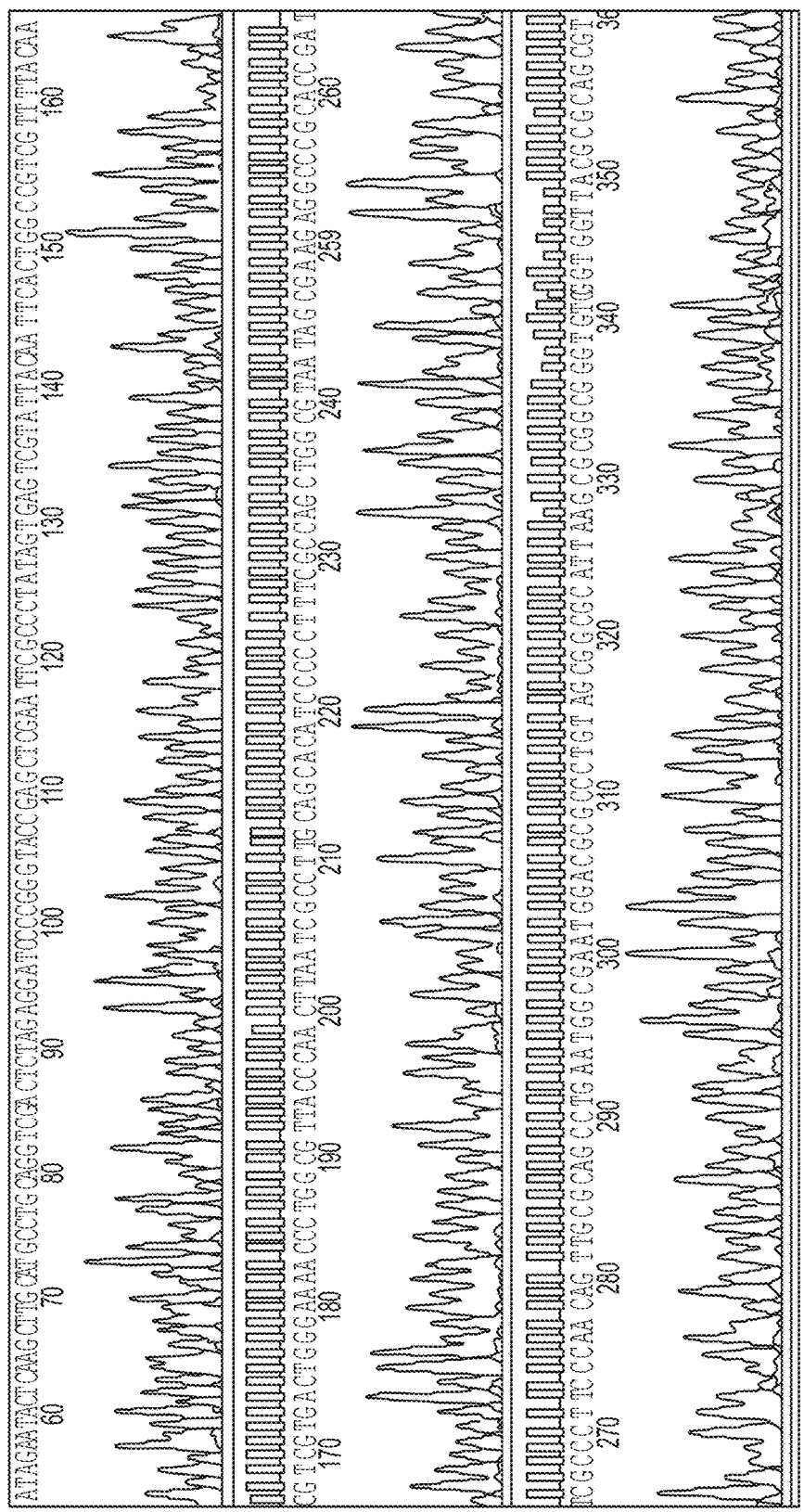
FIG. 10 is a sequencing trace (electropherograms) for sequencing product produced in the biochip of FIG. 1.
Figure 10B:
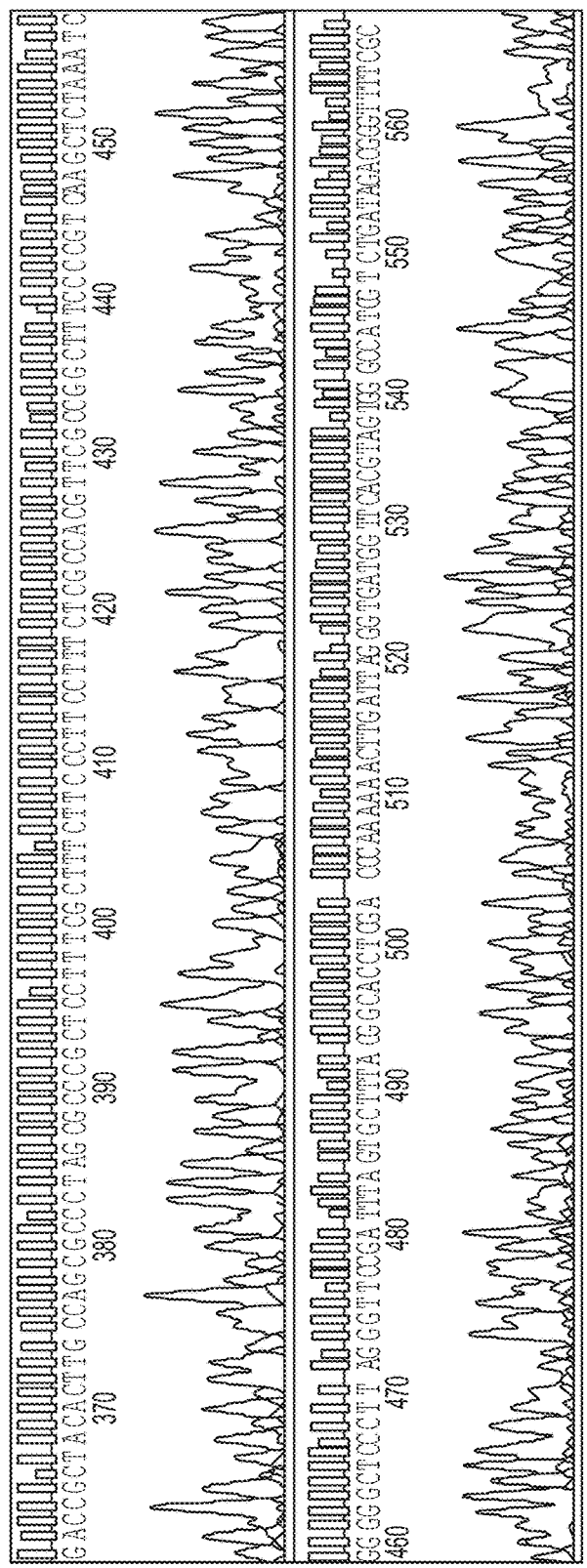

The biochip was then pressurized to 30 psig $N_2$ and thermally cycled using the following temperature profile:
95° C./1 min initial denaturation
30 cycles of the following
Denaturation at 95° C. for 5 sec
Annealing at 50° C. for 10 sec
Extension at 60° C. for 1 min Samples (see, FIG. 9l) were retrieved and purified by ethanol precipitation and analyzed by electrophoretic separation and laser-induced fluorescence detection on the Genebench™ instrument as described infra (Part II, Example 5). Phred quality analysis yielded 408+/−57 QV20 bases per sample.

Example 3

Ultrafiltration in 4-Sample Biochips

Figure 11:
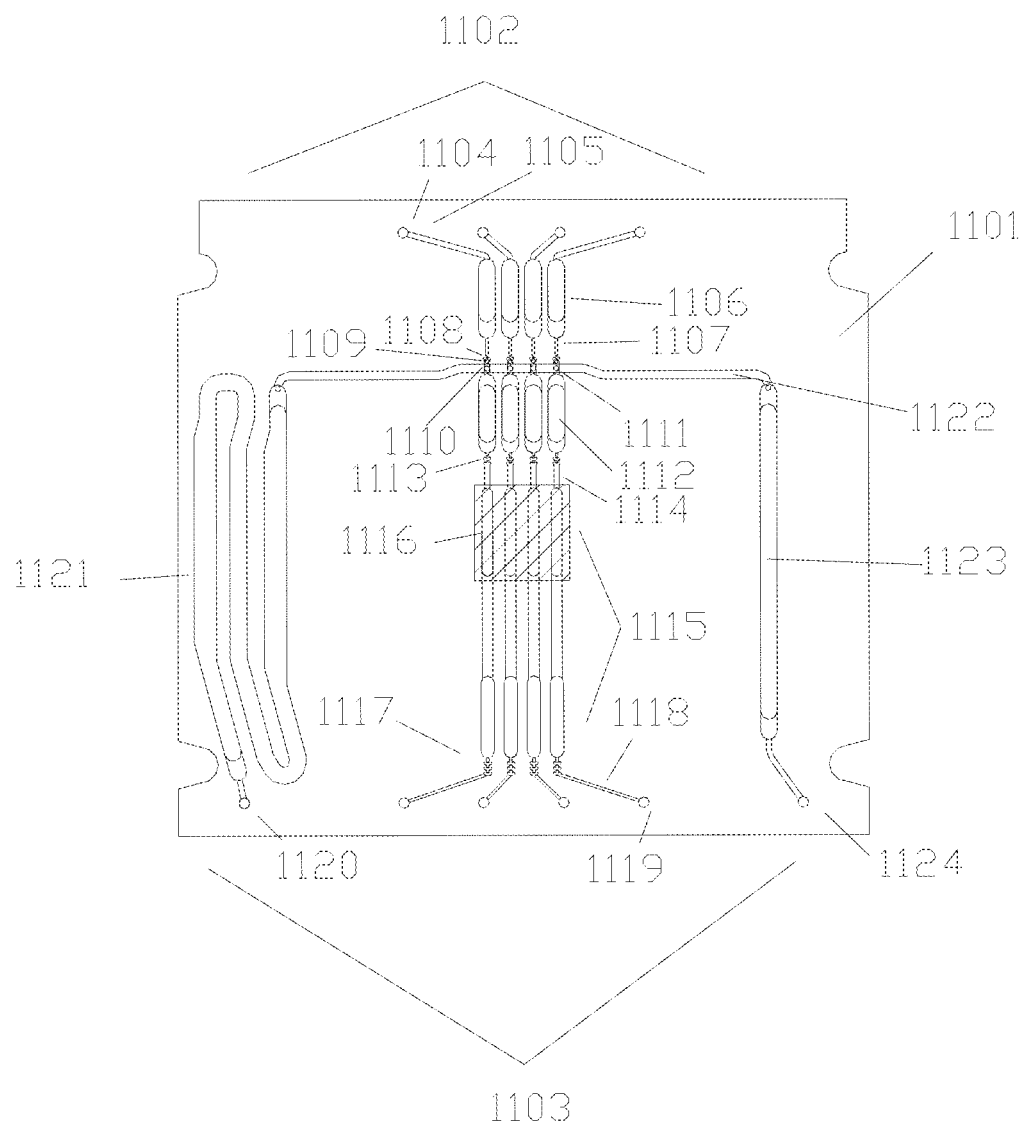
FIG. 11 is an illustration showing an embodiment of an integrated biochip for the performance of ultrafiltration of a cycle sequencing product. The chip assembly is similar to that in biochip 1 except for the addition of an ultra-filtration (UF) filter 1116 between layers 3 and 4.

A 4-sample biochip for the performance of sequencing product purification was constructed of four layers, as discussed in Example 1, and is shown in FIG. 11. One additional element in construction was the ultra-filtration (UF) filter 1116, which is cut to size and placed between layers 3 and 4 prior to thermal bonding. The creation of a good bond around the UF filter necessitated the use of layer 3. Layers 3 and 4 create uninterrupted perimeters around the filter, because all channels leading to and from the filter are in the bottom of layer 2. (Bonding directly between layer 2 and 4, for example, leaves a poor bond to the filter where channels cross the filter.) In this example, a regenerated cellulose (RC) filter of molecular weight cut-off (MWCO) 30 kD was used (Sartorius, Goettingen, Germany). A variety of other MWCOs (10 kD, 50 kD, and 100 kD) have been examined, as has an alternative material, polyethersulfone (Pall Corporation, East Hills, N.Y.).

1. Four 10 μL samples of cycle sequencing product generated in tube reactions using pUC18 template and KOD enzyme were added to ports 1104 in the first layer and driven through channel 1105 in the second layer to the chamber 1106 in the second layer. 200 μL of deionized water was added to port 1120 (a through-hole in the first layer) to reservoir 1121 in the second layer. The biochip was then installed in two pneumatic interfaces.

The following pressure profile was carried out using the pneumatic system software. All solenoid valves corresponding to biochip ports were closed unless otherwise noted.

2. A pressure of 0.09 psig was applied to ports 1104 with ports 1119 open to atmosphere for 5 sec to drive the sequencing product to capillary valves 1108 in layer 1, where they were retained.

3. A pressure of 0.6 psig was applied to ports 1104 with ports 1119 open to atmosphere for 0.1 sec to burst the samples through capillary valves 1108 in layer 1 and deliver them through through-holes 1111 in layer 2 into UF input chambers 1112 in layer 2.

Figure 12:
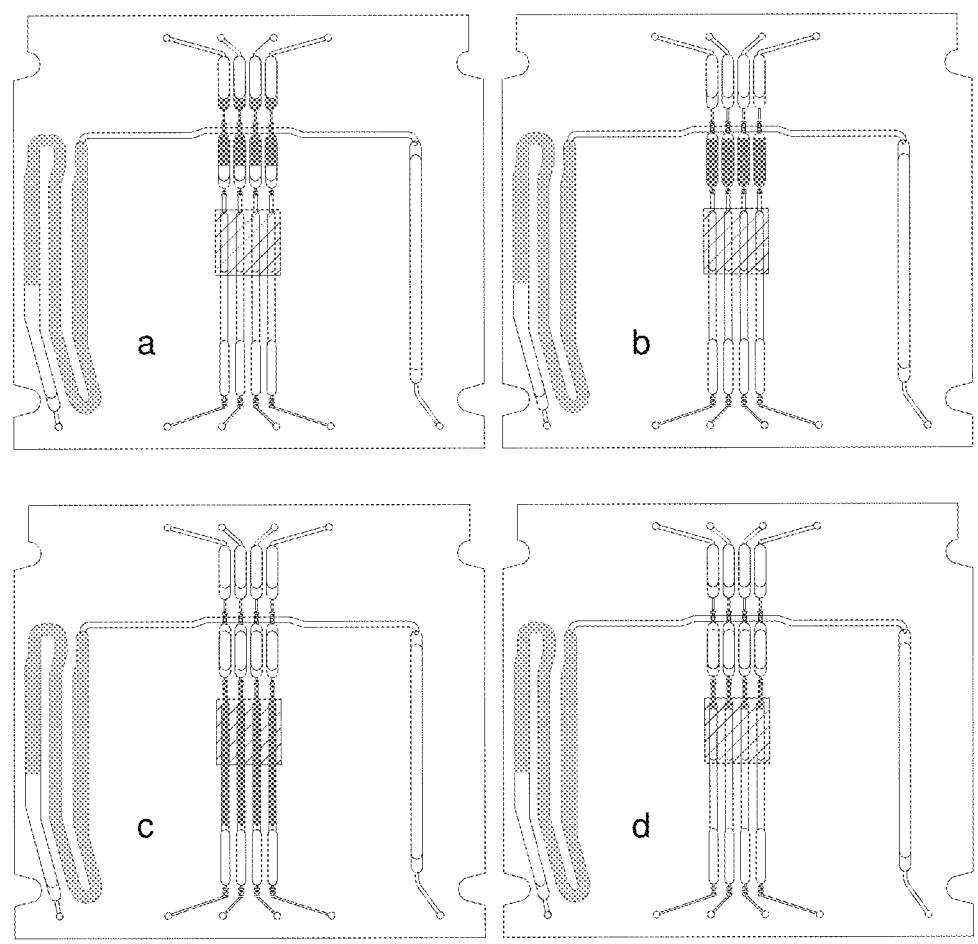
FIG. 12 is an illustration showing the fluidic steps of the biochip of FIG. 11 during purification of sequencing product.
Figure 12:
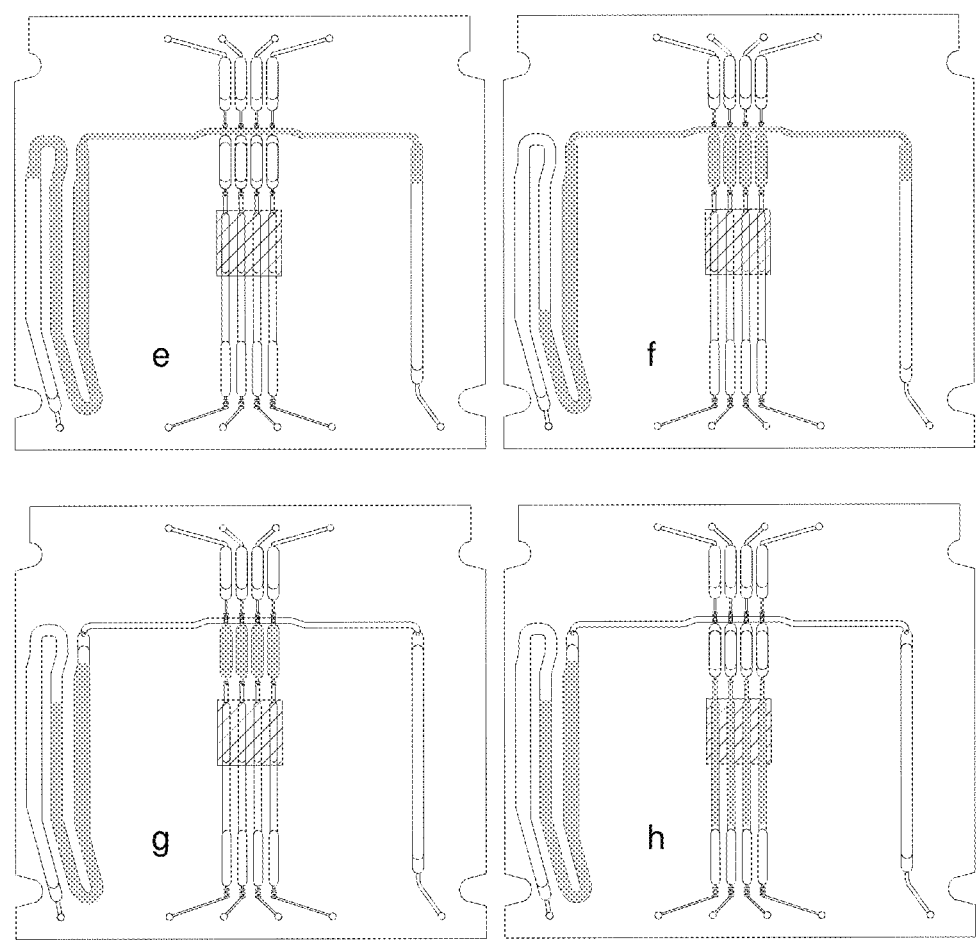
Figure 12:
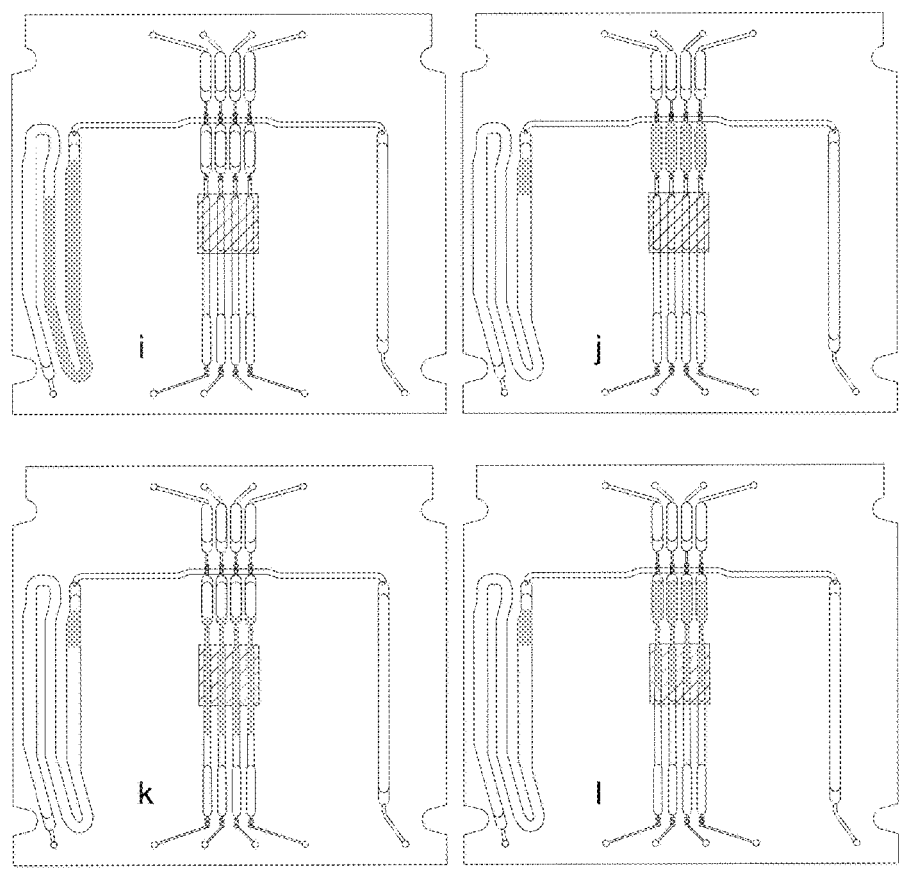
Figure 12:
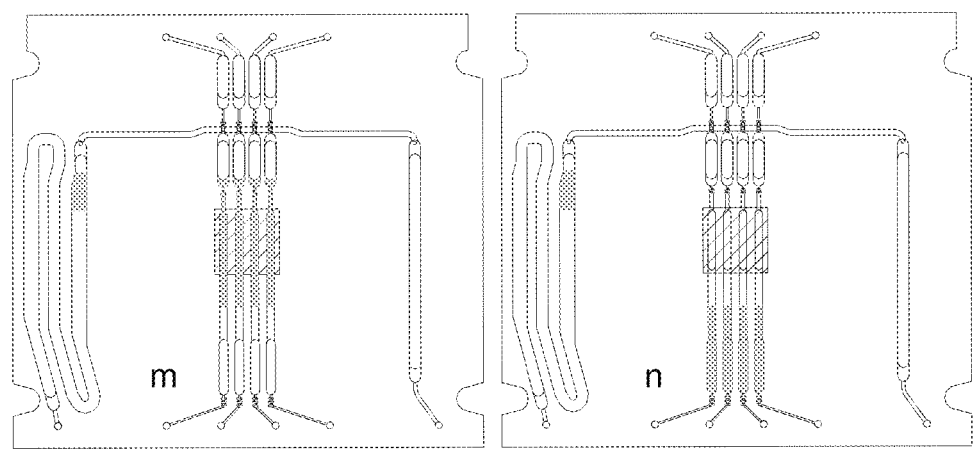
Figure 12A:
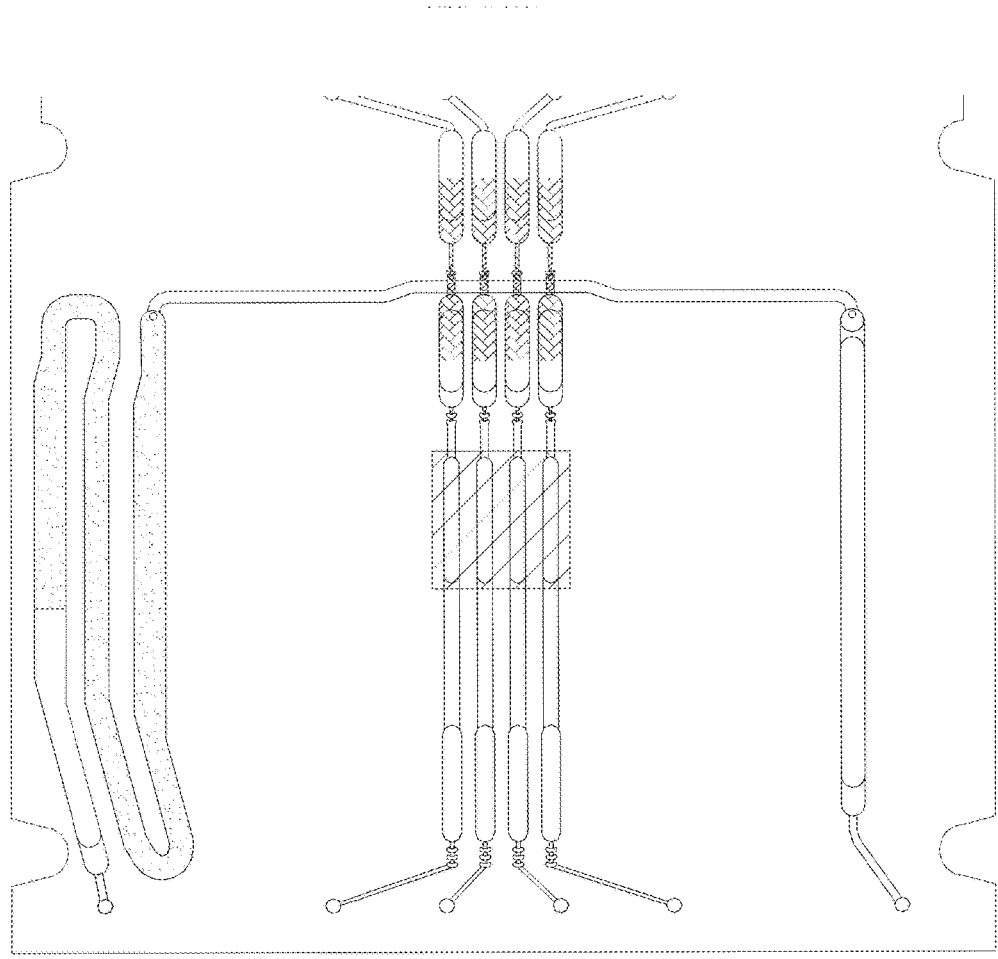
FIGS. 12*a* and 12*b* are illustrations showing delivery of a Sanger product to the UF input chambers.
Figure 12B:
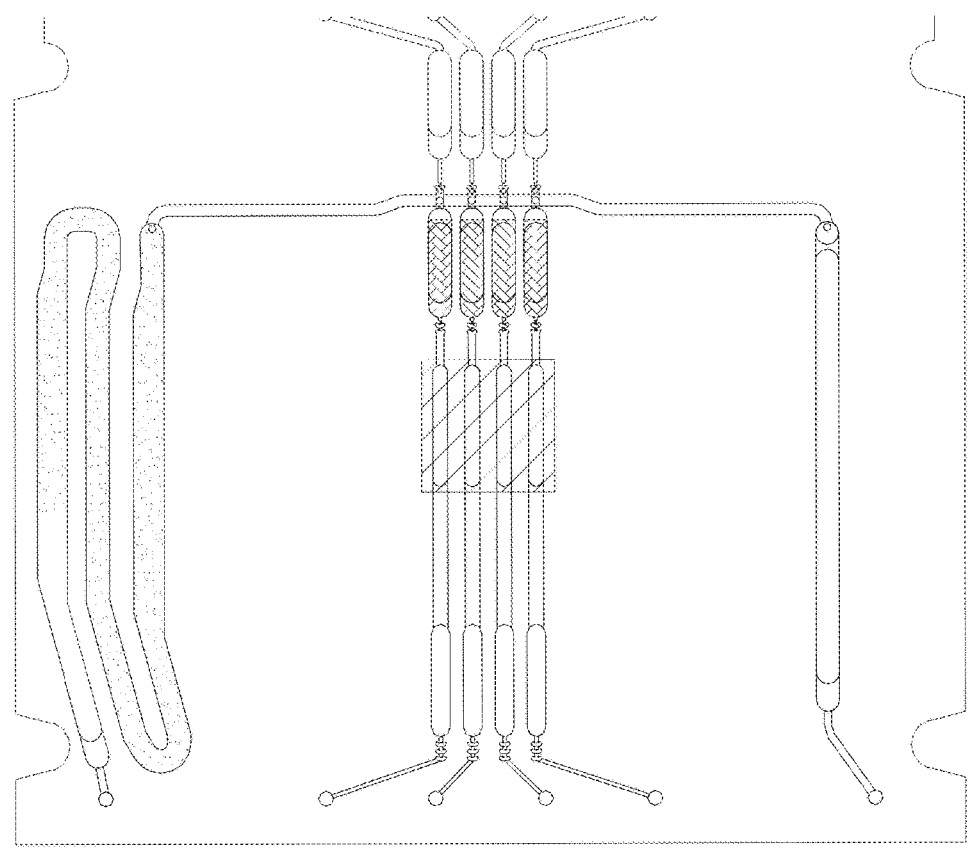

4. A pressure of 0.09 psig was applied for to ports 1104 with ports 1119 open to atmosphere for 10-30 sec (different times were used in different experiments) to complete delivery of sequencing product to chambers 1112. Sequencing product was retained by capillary valves 1113 in layer 2 (see FIGS. 12a and 12b).

5. A pressure of 0.8 psig was applied to port 1124 with ports 1119 and 1104 open to atmosphere for 0.5 sec to drive sequencing product through valves 113 into filtration chambers 1115. This also cleared input capillary valves 1108 of retained liquid.

Figure 12C:
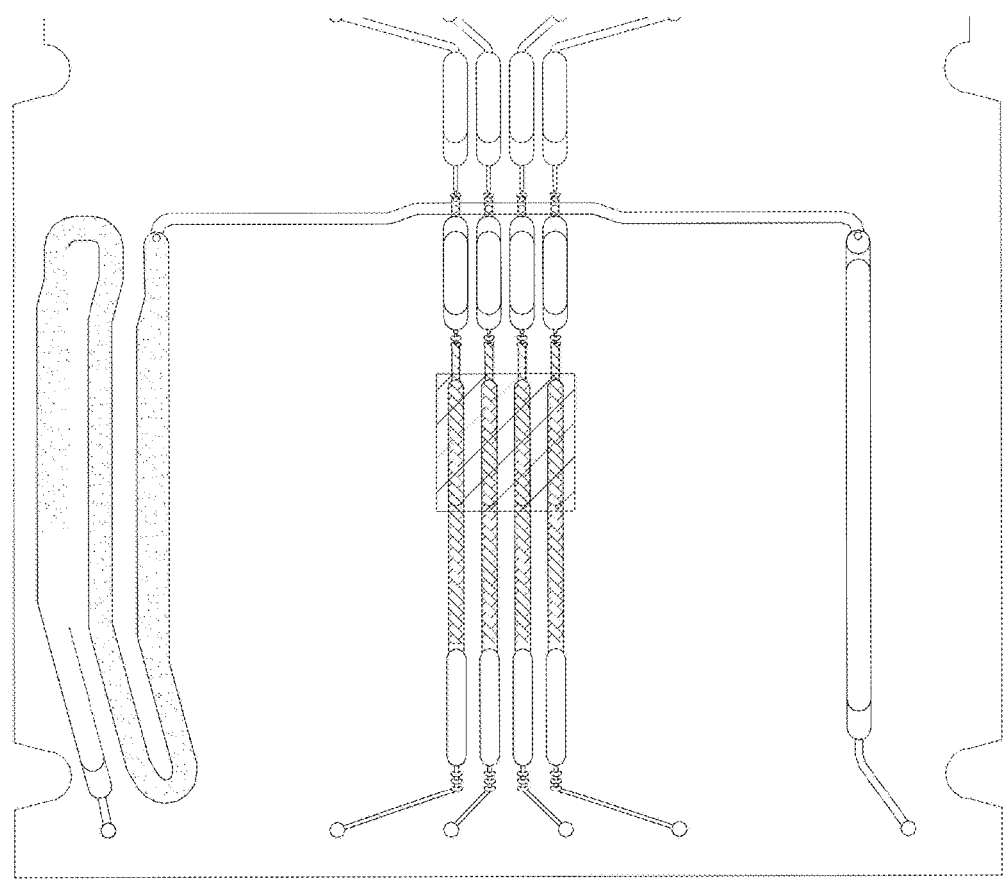
FIG. 12*c* is an illustration showing the sequencing product delivered to the filtration chamber.

6. A pressure of 0.09 psig was applied to port 1124 with ports 1119 open to atmosphere for 10-30 sec to complete delivery of the sequencing product to chamber 1115. Sequencing product was retained at valve 1113 (see, FIG. 12c).

Figure 12D:
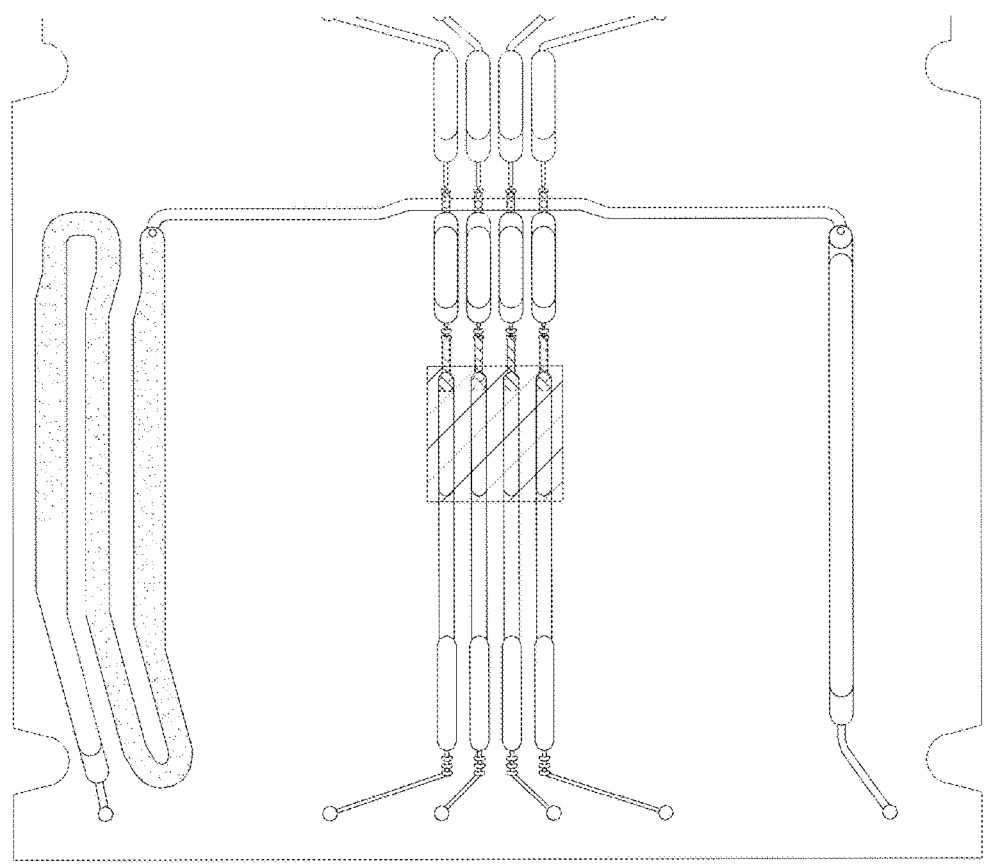
FIG. 12*d* is an illustration showing is nearly complete filtration of the sequencing product.

7. A pressure of 7.5 psig was slowly applied to all ports of the chip for ultrafiltration. During ultrafiltration, the sequencing product meniscus remains pinned at 1113 while the leading edge of the liquid "retracts" as liquid was driven through the filter 1116. 10 µL of sequencing product required ~120 sec for filtration. The pressure was released after filtration (see, FIGS. 12c and 12d).

Figure 12E:
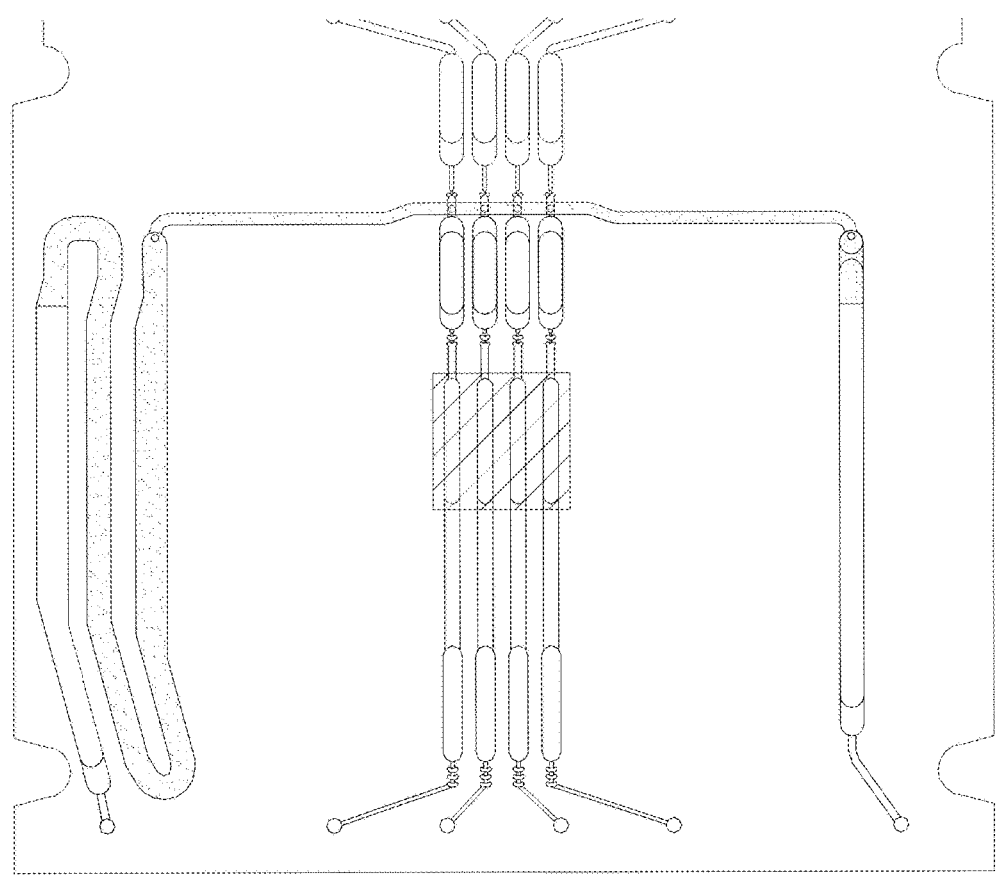
FIGS. 12*e* through 12*g* are illustrations showing delivery of wash to the UF input chambers and subsequent removal of excess wash from the delivery channel.

8. A pressure of 0.09 psig was applied to port 1120 with port 1124 open to atmosphere for 3 sec to drive water into channel 1122 (in layer 4) and partially-fill overflow chamber 1123 (see, FIG. 12e).

9. A pressure of 0.8 psig was applied to ports 1120 and 1124 with ports 1119 open to atmosphere to drive water through through-hole capillary valves 1110 in channel 1122 into chambers 1112.

Figure 12F:
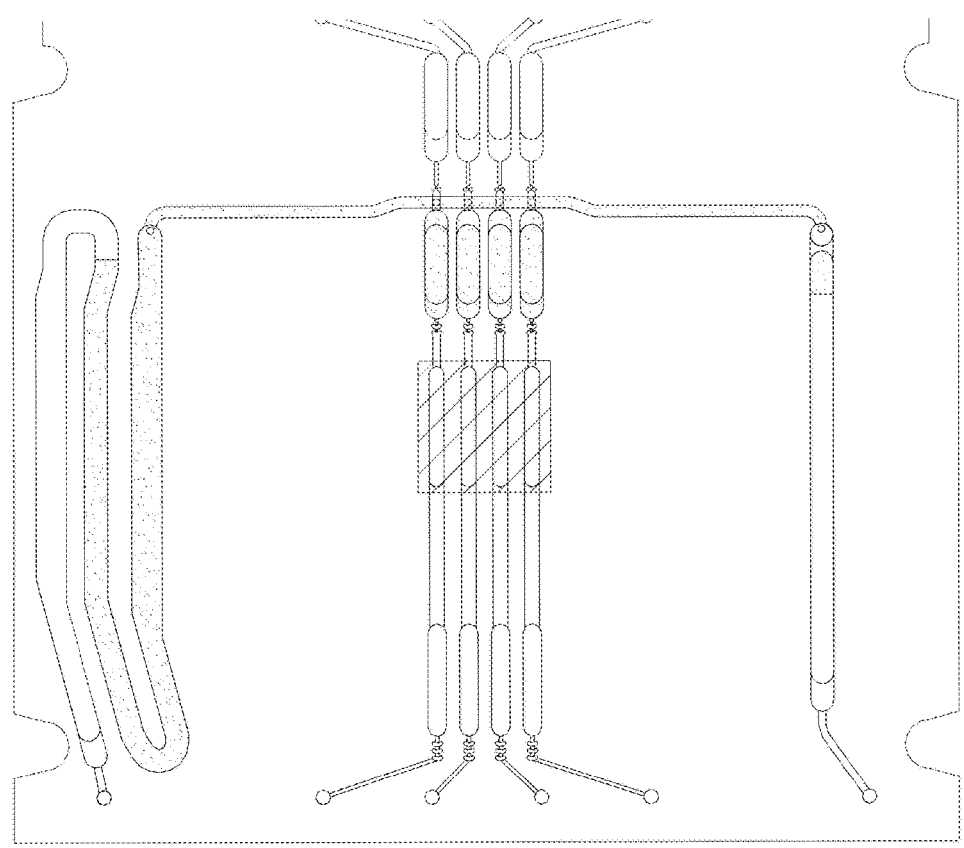

10. A pressure of 0.09 psig was applied to port 1120 with ports 1119 open to atmosphere for 10-30 sec to complete delivery of liquid to chambers 1112, where it was retained by valves 1113. (see, FIG. 12f).

Figure 12G:
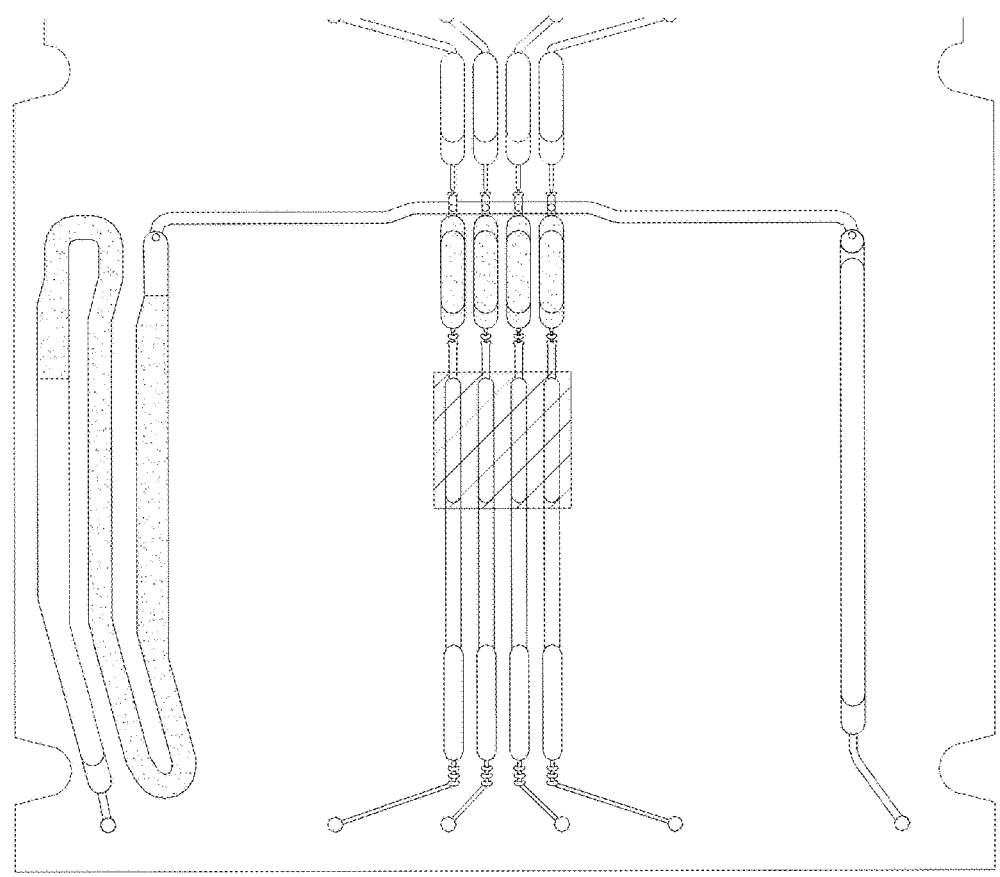

11. A pressure of 0.09 psig was applied to port 1124 with port 1120 open to drive water in chamber 1123 and channel 1122 back into chamber 1121 (see, FIG. 12g).

12. A pressure of 0.8 psig was applied to port 1124 with ports 1119 and 1104 open to atmosphere for 0.5 sec to drive water through valves 113 into filtration chambers 1115. This also cleared input capillary valves 1108 of retained liquid.

Figure 12H:
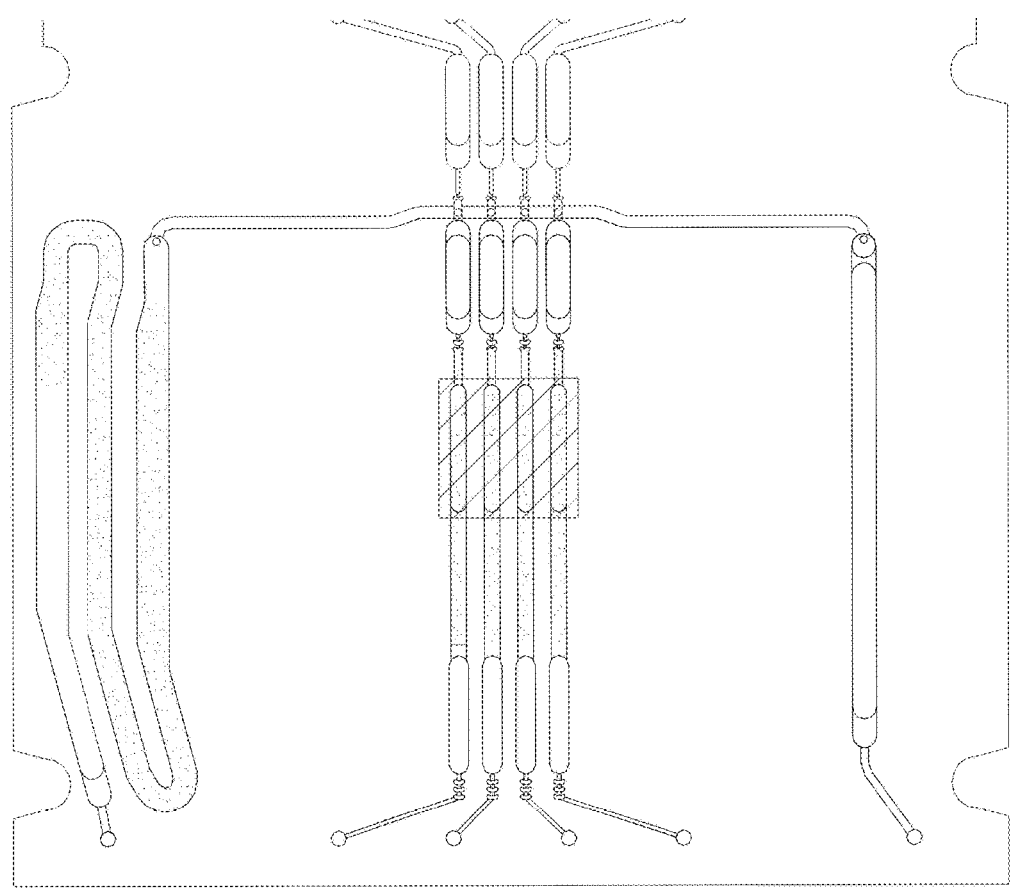
FIG. 12*h* is an illustration showing the beginning of the first wash cycle; it is followed by filtration as in FIG. 12*d* and a subsequent wash cycle.
Figure 12I:
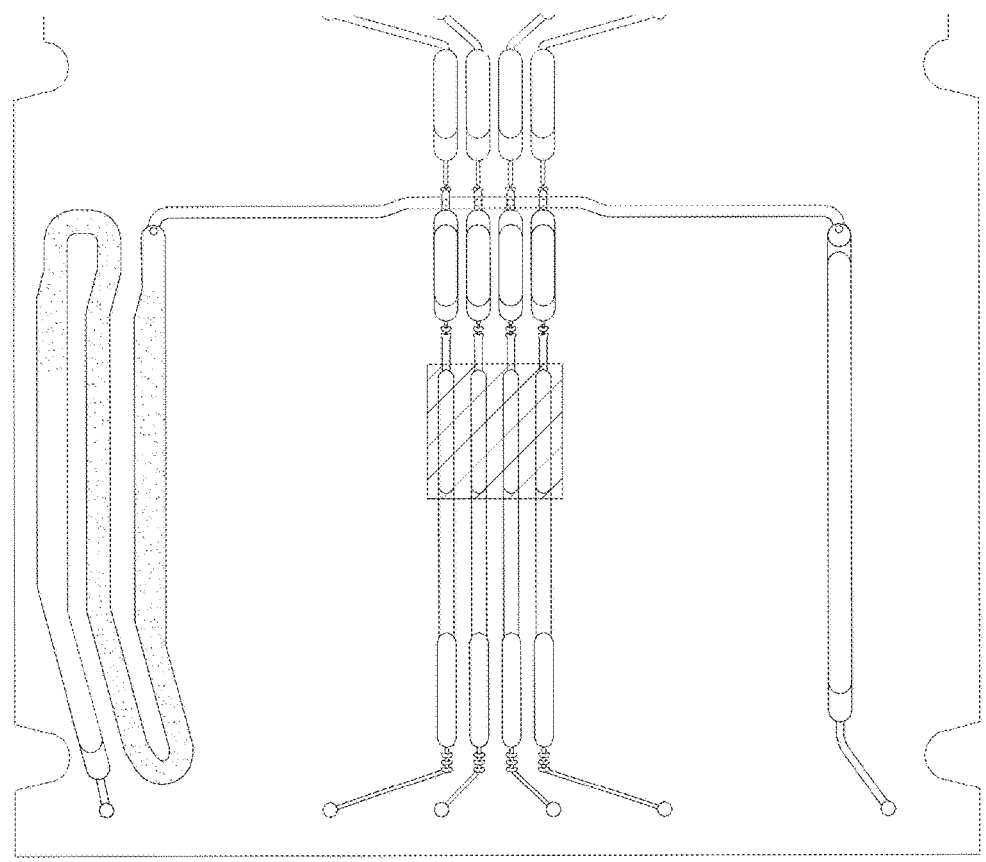
FIGS. 12*i* and 12*j* are illustrations showing elution liquid (the same liquid as the wash) being delivered to the UF input chambers.
Figure 12J:
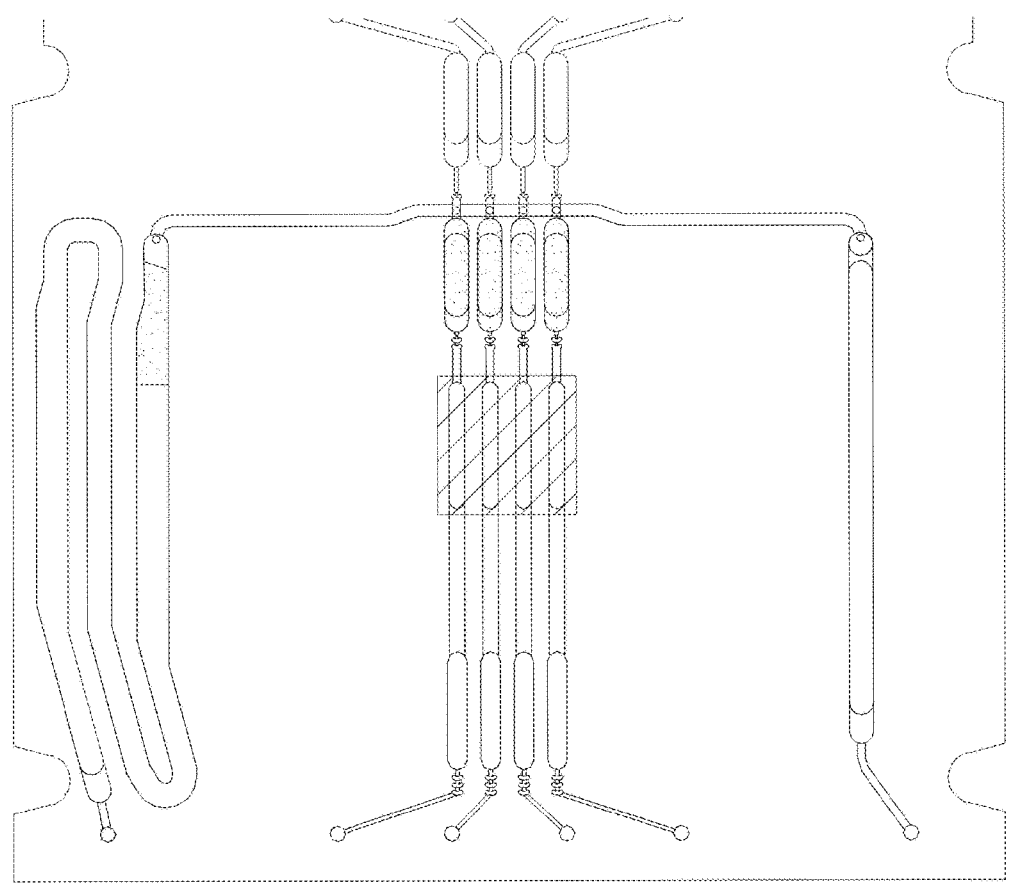

13. A pressure of 0.09 psig was applied to port 1124 with ports 1119 open to atmosphere for 10-30 sec to complete delivery of water to chamber 1115. Sequencing product was retained at valve 1113 (see, FIG. 12h).

The water was driven through the UF filter as in step 6 above, completing the first wash Steps 8-13 were repeated one additional time.

Figure 12K:
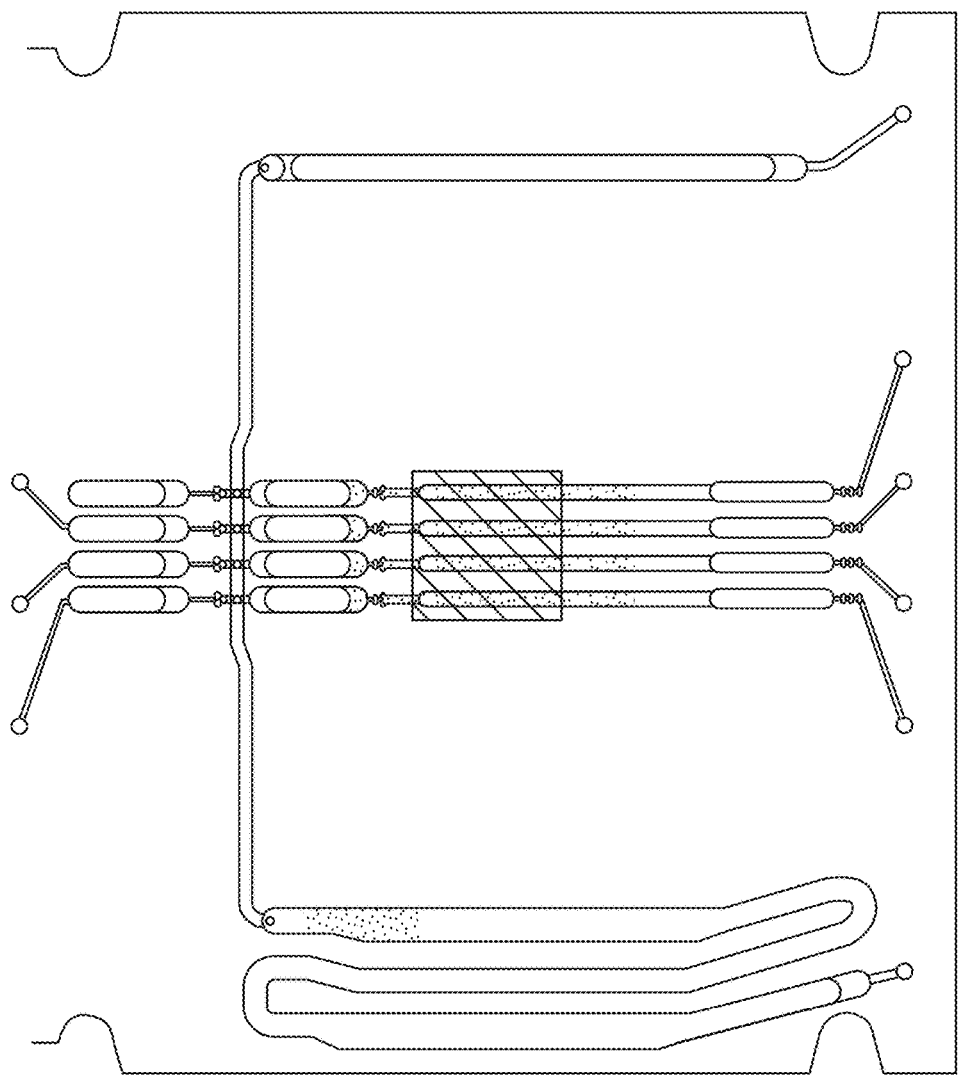
FIGS. 12*k* through 12*m* are illustrations showing a single cycle of pressurizing the UF input chambers with the output ports closed, and then releasing the pressure to cause reciprocal motion.

Steps 8-12 were repeated to partially-fill chambers 1115 with a final volume of water used for elution (see, FIG. 12k).

Figure 12L:
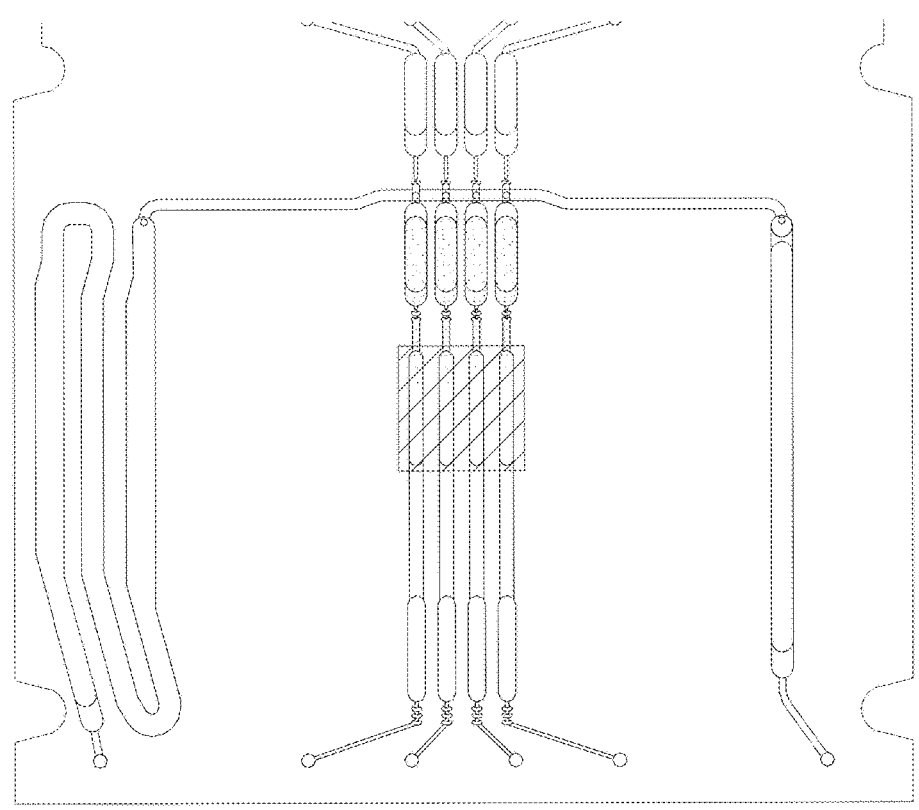

Vacuum of 1.6 psig was applied to ports 1104 with all other ports closed for 1 sec, drawing some water from chambers 1115 into chambers 1112 (the maximum motion being dictated by the creation of a vacuum of equal magnitude in the dead-space between the meniscus of the liquid and the solenoid valves corresponding to ports 1119), (see, FIG. 12l).

Figure 12M:
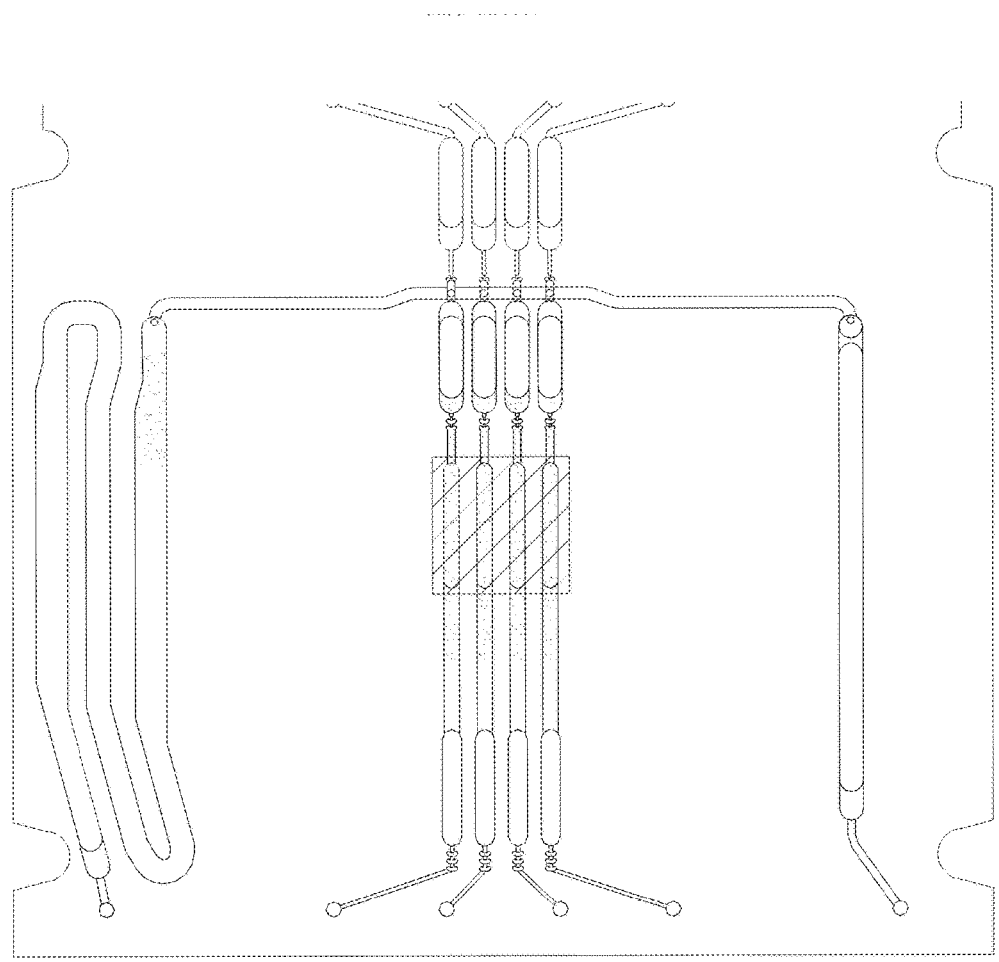

Ports 1104 were opened to atmosphere for 1 sec, allowing the liquid to move back into chamber 1115 due to the partial vacuum generated between the liquid and the valves corresponding to ports 1119 (see, FIG. 12m).

16-17 was repeated 50× to create 50 elution cycles.

A pressure of 0.09 psig was applied to port 1124 for 10 sec with ports 1119 open to atmosphere to drive liquids such that its trailing meniscus was pinned at 1113.

Figure 12N:
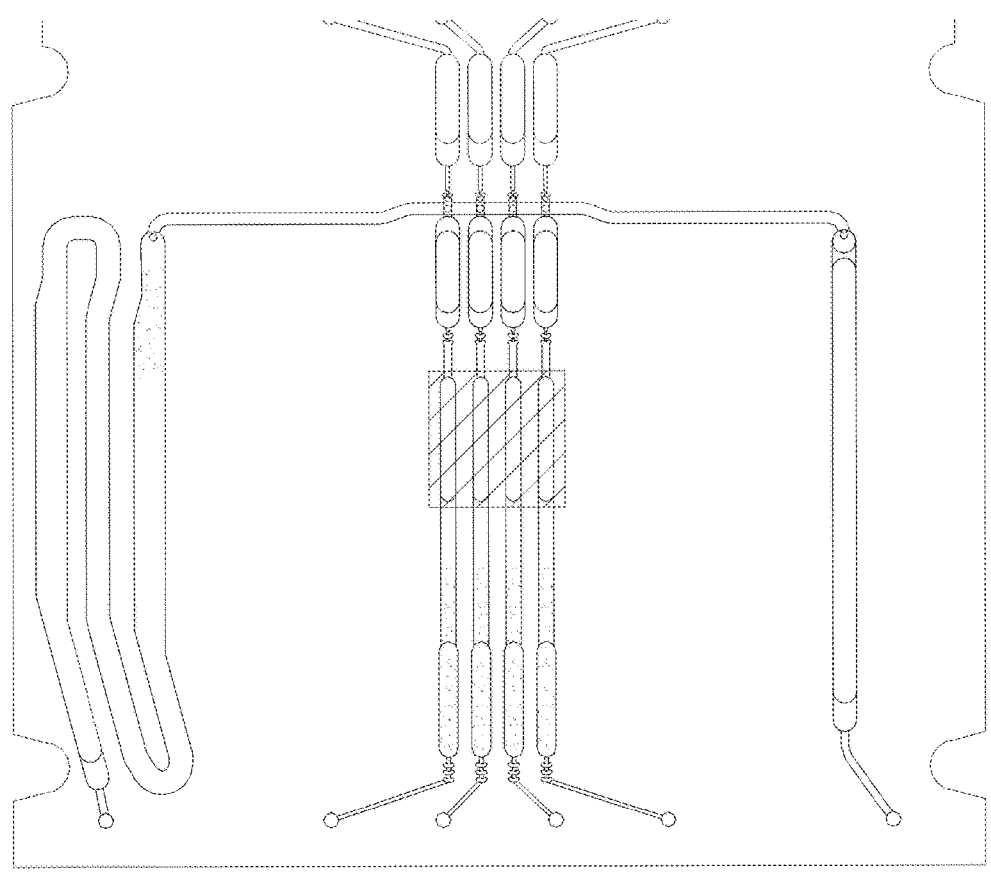
FIG. 12*n* is an illustration showing purified product ready for further processing or removal.

A pressure of 0.7 psig/0.05 sec was applied to port 1124 with ports 1119 open to atmosphere to detach the eluent (see, FIG. 12n).

The samples were retrieved and run directly on Genebench™ as described, yielding up to 479 QV20 bases.

Example 4

Fully Integrated Biochip for Nucleic Acid Extraction, Template Amplification, Cycle Sequencing, Purification of Sequencing Product, and Electrophoretic Separation and Detection of Purified Product FIG. 13 illustrates an embodiment of a 16-sample biochip, 1301, which combines the lysis and extraction, template amplification, and cycle sequencing functions of the biochip of FIG. 1; the ultrafiltration function of the chip of FIG. 11; and electrophoretic separation and detection. The process through ultrafiltration is carried out by sub-component 1302 and can be performed as described in examples 1, 2, and 3; transfer points 1304 on the bottom surface of 1302 are aligned with input wells 1305 on the separation sub-component 1303.

Injection is performed electrokinetically with a pre-concentration step using counterelectrodes. The input well 1305, illustrated in FIG. 14, consists of a liquid receiving well 1401; a main separation electrode, 1402; and a counterelectrode 1403. Separation channel 1306 opens into the bottom of well reservoir 1401. The separation electrode is typically platinum or gold coated, and is preferably a planar gold-coated electrode that substantially covers 1, 3, or 4 of the internal surfaces of 1401. The counterelectrode is a thin gold, steel, or platinum wire (typically 0.25 mm in diameter) that has been coated with a thin layer (~10 µm) of cross-linked polyacrylamide. This forms a hydrogel protection layer on the electrode. In panel d, purified sequencing product (black dots within 1401) have been transferred to the well. Applying positive potential between 1402 and 1403, negatively charged sequencing product is drawn toward 1403, as in panels c-d. The hydrogel layer on 1403 prevents sequencing product from contacting the metal electrode and thus prevents electrochemistry and damage of the sequencing product. The counterelectrode 1403 is then allowed to float with respect to 1402. A positive potential is then applied between main separation electrode 1402 and the anode (not shown) at the far end of separation channel 1306. This allows product to be injected (panel e) and to electrophoresis down 1306 for separation and detection (panel f). As illustrated in FIG. 14, this scheme allows the concentration of sequencing product in the vicinity of the end of channel 1306 to be increased significantly relative to the concentration with that it is delivered from ultrafiltration. While such concentration is desirable for some applications, it is not necessary in all cases. In such cases, the well of FIG. 14 without the counterelectrode 1403 can be used to perform EKI directly. Alternatively, the single electrode in the loading well may be one half of a cross-T or double-T injector (see, for example, the U.S. patent application entitled, "PLASTIC MICROFLUIDIC SEPARATION AND DETECTION PLATFORMS", U.S. Ser. No. 12/080,745, filed on Apr. 4, 2008).

Separation occurs in separation channels 1306, and detection occurs via laser-induced fluorescence in the detection region 1307. In this biochip, a recess 1308 is provided to allow, for example, a Peltier block (not shown) to mate with the lower surface of 1301 to provide thermal cycling for PCR and cycle sequencing. Pneumatic interfaces (not shown) within the instrument clamp to the ends of the chip to provide microfluidic control.

II. Separation and Detection Systems

A. Detailed Description of Separation and Detection Components and their Uses

1. Separation Instrument

DNA separation is carried out on a biochip and instrumentation as described in U.S. Patent Application Publication No. US2006-0260941-A1. Separation chips can be glass (see, U.S. Patent Application Publication No. US2006-0260941-A1) or plastic (the U.S. patent application entitled, "PLASTIC MICROFLUIDIC SEPARATION AND DETECTION PLATFORMS", U.S. Ser. No. 12/080,745, filed on Apr. 4, 2008), each of which are hereby incorporated by reference in their entirety.

2. Excitation and Detection Instrumentation

The instrument comprises excitation and detection subsystems for interacting with and interrogating a sample. Samples typically include one or more biological molecules (including but not limited to DNA, RNA, and proteins) that are labeled with dyes (e.g., fluorescent dyes). The excitation subsystem comprises an excitation source or sources and an excitation beam path with optical elements including lenses, pinholes, mirrors and objectives, to condition and focus the excitation source in an excitation/detection window. Optical excitation of a sample can be accomplished by a series of laser types, with emission wavelengths in the visible region, between 400 to 650 nm. Solid state lasers can provide emission wavelengths of approximately 460 nm, 488 nm, and 532 nm. These lasers include, for example, the Compass, Sapphire and Verdi products from Coherent (Santa Clara, Calif.). Gas lasers include argon-ion and helium neon with emission in the visible wavelengths at approximately 488 nm, 514 nm, 543 nm, 595 nm, and 632 nm. Other lasers with emission wavelengths in the visible region are available from CrystaLaser (Reno, Nev.). In one embodiment, a 488 nm solid state laser Sapphire 488-200 (Coherent, Santa Clara, Calif.) can be utilized. In another embodiment, a light source with wavelength beyond the visible range can be used for exciting dyes having absorption and/or emission spectra beyond the visible range (e.g., infrared or ultra-violet emitting dyes). Alternatively optical excitation can be achieved by the use of non-laser light sources with emission wavelengths appropriate for dye excitation, including light emitting diodes, and lamps.

The detection subsystem comprises one or more optical detectors, a wavelength dispersion device (which performs wavelength separation), and one or a series of optical elements including, but not limited to, lenses, pinholes, mirrors and objectives to collect emitted fluorescence from fluorophore-labeled DNA fragments that are present at the excitation/detection window. The fluorescence emitted can be from a single dye or a combination of dyes. In order to discriminate the signal to determine its contribution from the emitting dye, wavelength separation of the fluorescence can be utilized. This can be achieved by the use of dichroic mirrors and bandpass filter elements (available from numerous vendors including Chroma, Rockingham, Vt.; and Omega Optical, Brattleboro, Vt.). In this configuration, the emitted fluorescence passes through a series of dichroic mirrors where one portion of the wavelength will be reflected by the mirror to continue traveling down the path, and the other portion will pass through. A series of discrete photodetectors, each one positioned at the end of the dichroic mirror will detect light over a specific range of wavelengths. A bandpass filter can be positioned between the dichroic mirror and photodetector to further narrow the wavelength range prior to detection. Optical detectors that can be utilized to detect the wavelength-separated signals include photodiodes, avalanche photodiodes, photomultiplier modules, and CCD cameras. These optical detectors are available from suppliers such as Hamamatsu (Bridgewater, N.J.).

Figure 15:
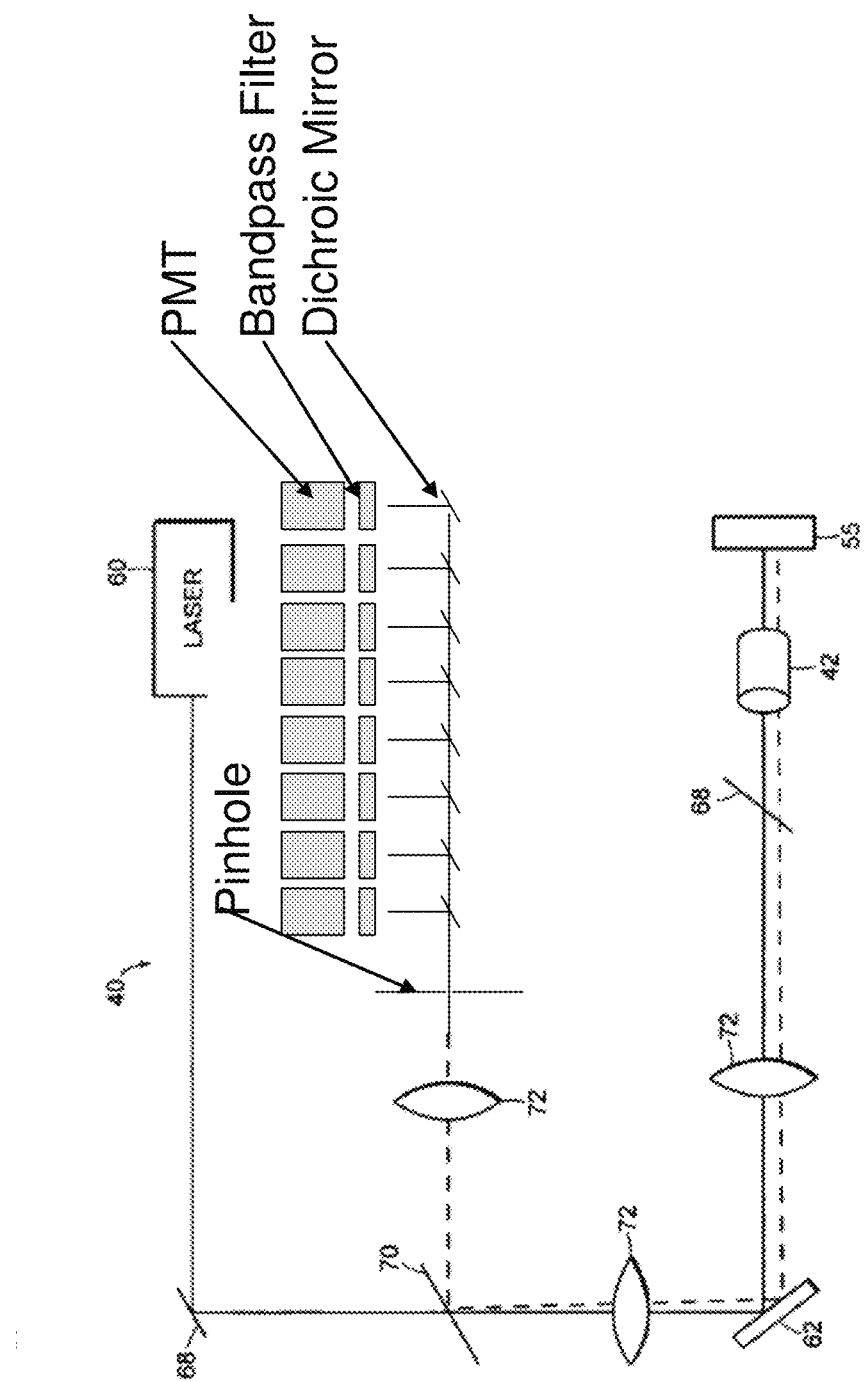
FIG. 15 is an illustration showing an embodiment of an excitation and detection system.

In one embodiment, wavelength components are separated by the use of dichroic mirrors and bandpass filters and these wavelength components are detected with Photomultiplier Tube (PMT) detectors (H7732-10, Hamamatsu). The dichroic mirror and bandpass components can be selected such that incident light on each of the PMTs consists of a narrow wavelength band corresponding to the emission wavelength of the fluorescent dye. The band pass is typically selected to be centered about the fluorescent emission peak with a band pass of wavelength range of between 1 and 50 nm. The system is capable of eight color detection and can be designed with eight PMTs and a corresponding set of dichroic mirrors and bandpass filters to divide the emitted fluorescence into eight distinct colors. More than eight dyes can be detected by applying additional dichroic mirrors, bandpass filters and PMT. FIG. 15 shows the beam path for discrete bandpass filter and dichroic filter implementation. An integrated version of this wavelength discrimination and detection configuration is the H9797R, Hamamatsu, Bridgewater, N.J.

Another method of discriminating the dyes that make up the fluorescence signal involves the use of wavelength dispersive elements and systems such as prisms, diffraction gratings, transmission gratings (available from numerous vendors including ThorLabs, Newton, N.J.; and Newport, Irvine, Calif.; and spectrographs (available from numerous vendors including Horiba Jobin-Yvon, Edison, N.J.). In this mode of operation, the wavelength components of the fluorescence are dispersed over a physical space. Detector elements placed along this physical space detect light and allow the correlation of the physical location of the detector element with the wavelength. Detectors suitable for this function are array-based and include multi-element photodiodes, CCD cameras, back-side thinned CCD cameras, multi-anode PMT. One skilled in the art will be able to apply a combination of wavelength dispersion elements and optical detector elements to yield a system that is capable of discriminating wavelengths from the dyes used in the system.

Figure 16:
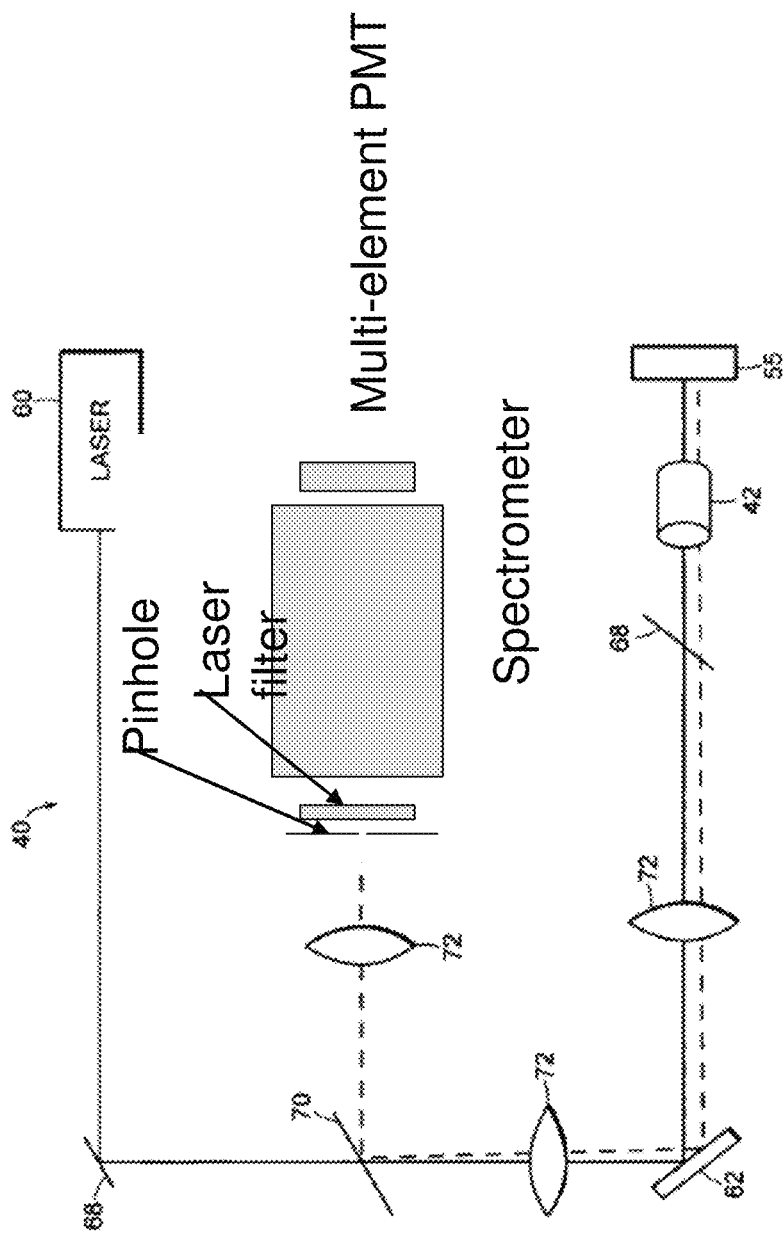
FIG. 16 is an illustration showing an embodiment of an excitation and detection system.

In another embodiment, a spectrograph is used in place of the dichroic and bandpass filters to separate the wavelength components from the excited fluorescence. Details on spectrograph design is available in John James, *Spectrograph Design Fundamental*, Cambridge, UK: Cambridge University Press, 2007. The spectrograph P/N MF-34 with a concave holographic grating with a spectral range of 505-670 nm (P/N 532.00.570) (HORIBA Jobin Yvon Inc, Edison, N.J.) is used in this application. Detection can be accomplished with a linear 32-element PMT detector array (H7260-20, Hamamatsu, Bridgewater, N.J.). Collected fluorescence is imaged on the pinhole, reflected, dispersed, and imaged by the concave holographic grating onto the linear PMT detector that is mounted at the output port of the spectrograph. The use of a PMT-based detector takes advantage of the low dark noise, high sensitivity, high dynamic range, and rapid response characteristic of PMT detectors. The use of a spectrograph and multi-element PMT detector for detection of excited fluorescence allows for flexibility in the number of dyes and the emission wavelength of dyes that can be applied within the systems and within the lane, without the need for physically reconfiguring the detection system (dichroic, bandpass and detectors) of the instrument. The data collected from this configuration is a wavelength dependent spectra across the visible wavelength range for each scan for each lane. Generating a full spectrum per scan provides dye flexibility both in terms of dye emission wavelength and number of dyes that can be present within a sample. In addition, the use of the spectrometer and linear multi-element PMT detector also allows for extremely fast read-out rates as all the PMT elements in the array are read-out in parallel. FIG. 16 shows the beam path for multi-element PMT and spectrograph implementation.

Instruments may employ a staring mode of operation, to detect multiple lanes simultaneously and multiple wavelengths simultaneously. In one configuration, the excitation beam is simultaneously impinged on all lanes at the same time. The fluorescence from this is collected by a two dimensional detector such as a CCD camera or array. In this staring mode of collection, a wavelength dispersive element is used. One dimension of the detector represents the physical wavelength separation, while the other dimension represents the spatial or lane-lane separation.

For simultaneous excitation and detection of multiple samples, a scanning mirror system (62) (P/N 6240HA, 67124-H-0 and 6M2420X40S100S1, Cambridge technology, Cambridge Mass.) is utilized to steer both the excitation and detection beam paths in order to image each of the lanes of the biochip. In this mode of operation, the scanning mirror steers the beam paths, scanning sequentially from lane to lane from the first lane to the last lane, and the repeating the process again from the first lane to the last lane again. A lane-finding algorithm such as that described in U.S. Patent Application Publication No. US2006-0260941-A1 is used to identify location of lane.

An embodiment of an optical detection system for simultaneous multiple lane and multi dye detection is shown in FIG. 16. The fluorescence excitation and detection system 40 excites the components separated by electrophoresis of a DNA sample (e.g., containing DNA fragments following amplification of a set of STR loci) by scanning an energy source (e.g. a laser beam) through a portion of each of the microchannels while collecting and transmitting the induced fluorescence from the dye to one or more light detectors for recordation, and ultimately analysis.

In one embodiment, the fluorescence excitation and detection assembly 40 includes a laser 60, a scanner 62, one or more light detectors 64, and various mirrors 68, spectrograph, and lenses 72 for transmitting a laser beam emitted from the laser 60 through opening 42 to the test module 55 and back to the light detectors 64. The scanner 62 moves the incoming laser beam to various scanning positions relative to the test module 55. Specifically, the scanner 62 moves the laser beam to a pertinent portion of each micro channel within the test module 55 to detect respective separate components. The multi element PMT 64 collects data (e.g. the fluorescent signals from DNA fragments of varying length) from the test module 55 and provides the data electronically through a cable attached to a port to a data acquisition and storage system located outside the protective cover. In one embodiment, the data acquisition and storage system can include a ruggedized computer available from Option Industrial Computers (13 audreuil-Dorion, Quebec, Canada).

In another embodiment (a "staring mode"), the excitation source is incident on all the detection spots simultaneously, and fluorescence from all detection spots is collected simultaneously. Simultaneous spectral dispersion (wavelength spectra of detected fluorescence) and spatial dispersion (detection spots) can be performed with a two dimensional detector array. In this configuration, the 2-dimensional detector array is positioned in the system such that spectral components are imaged and detected across one dimension of the array detector (row), while spatial components are imaged and detected across the other dimension of the array detector.

A preferred instrument utilizes a scanning mode of operation, rather than a "staring" mode. In scanning mode, signal for each channel is required to be collected, integrated, and read-out while the scanner is coincident with the lane being interrogated and before it is incident on the next channel. A detector with fast readout allows for optimal light collection and integration, translating into higher signal to noise performance. Ideally, the read-out time of the detector should be significantly less than the total time which the scanner is coincident with the channel. The multi-element PMT can be read-out in less than 0.7 ms and this read-out time is far less than the integration time for detection for each individual channel.

Fluorescence incident on the pinhole can be dispersed by the grating according to its wavelength composition and focused onto the linear multi-anode PMT detector array. The detector provides 32 current outputs, one for each of the elements in the array that correspond to the number of photons incident on the element. During multiple samples (or lanes) detection, when the laser is in position exciting the selected lane, the integrator circuitry will integrate the PMT output current to generate an output voltage proportional to the integrated PMT current. At the same time, the single ended output voltage is converted to differential mode using the Analog Devices (Norwood, Mass.) differential driver IC (P/N SSM2142). At the end of the integration time (defined by scan rate and number of lane), the data acquisition system will read the differential signal and save the data in its buffer. After the data have been saved, the data acquisition system will move the scanner to shift the laser beam to the next selected lane, at the same time resetting the integrator circuitry.

Each single element PMT module has its own integrator circuitry. For an 8 color detection system, there are 8 PMT modules and 8 integrator circuitries. Additional colors can be added using corresponding numbers of PMT modules and integrator circuitry.

Since each of the PMT elements (H77260-20, Hamamatsu, Japan) has a similar or more rapid signal response as a single PMT tube (H7732-10, Hamamatsu, Japan), and the readout is in parallel, this detector is able to operate very rapidly. When coupled with the spectrometer, this spectrometer and multi-anode detector system is able to provide full spectral scans across the visible spectrum (450 nm to 650 nm) with readout-times of less than 0.1 ms.

The ability to provide fast refresh rates allows this spectrometer/detector system to be applied to scanning mode implementation of detection of multiple lanes sequentially within a single run. The use of PMT based detectors provides for low noise, high sensitivity and high dynamic range, and fast response. The 140 mm spectrometer with a concave holographic grating (Horiba Jobin-Yvon) and multianode PMT detector is the H7260-20 detector (Hamamatsu, Japan). Other spectrometers configurations and multi-anode PMT detectors can also be used for this application.

Determination of nucleotide bases from the electrophoregrams was achieved using signal processing algorithms to correct, filter, and analyze the data. This process consisted of locating a callable signal, correcting the signal baseline, filtering out noise, removing color cross-talk, identifying signal peaks, and determining associated bases. Locating the callable signal was performed to remove extraneous data from the beginning and end of the signal and accomplished by employing a threshold. Next, the background was removed from the signal, so that the signal had a common baseline for all detected colors. Finally, a lowpass filter was applied to remove high frequency noise from the signal.

To disambiguate the detected colors, a weighted matrix was calculated and applied to the signal to amplify the color-space of the nucleotide-dye spectrum. Calculation of this color separation matrix was accomplished using the methods of Li et al. *Electrophoresis* 1999, 20, 1433-1442. In this adaptation, a "m×n" color separation matrix is calculated from correlating the "m" number of dyes utilized in the assay with the "n" number of detector elements. The conversion of the signal from the detector space (PMT elements), to the dye space is performed by matrix manipulation as follows: D=CSM×PMT, where D is the signal in dye space for each of the m dyes, CSM is the color separation matrix, and PMT is a matrix with the signal from each of the n elements of the detector.

Next, the peaks in the color separated signal were identified using a combination of zero-crossing filters and frequency analysis. Finally, for fragment sizing applications, the corrected traces were allele-called to identify each fragment and to assign a fragment size based on a sizing standard. For DNA sequencing applications, the corrected traces were base-called to associate one of the four nucleotides with each peak in the trace. A detailed description of base calling can be found in Ewing et al. *Genome Research,* 1998, 8, 175-185, and Ewing et al., *Genome Research,* 1998, 8, 186-194, the disclosures of that are hereby incorporated by reference in their entirety.

3. Dye Labels

Dye labels attached to oligonucleotides and modified oligonucleotides can be synthesized or obtained commercially (e.g. Operon Biotechnologies, Huntsville, Ala.). A large number of dyes (greater than 50) are available for application in fluorescence excitation applications. These dyes include those from the fluorescein, rhodamine AlexaFluor, Biodipy, Coumarin, and Cyanine dye families. Furthermore, quenchers are also available for labeling oligo sequences to minimize background fluorescence. Dyes with emission maxima from 410 nm (Cascade Blue) to 775 nm (Alexa Fluor 750) are available and can be used. Dyes ranging between 500 nm to 700 nm have the advantage of being in the visible spectrum and can be detected using conventional photomultiplier tubes. The broad range of available dyes allows selection of dye sets that have emission wavelengths that are spread across the detection range. Detection systems capable of distinguishing many dyes have been reported for flow cytometry applications (see, Perfetto et al., *Nat. Rev. Immunol.* 2004, 4, 648-55; and Robinson et al., *Proc of SPIE* 2005, 5692, 359-365).

Fluorescent dyes have peak excitation wavelengths that are typically 20 to 50 nm blue-shifted from their peak emission wavelength. As a result, use of dyes over a wide range of emission wavelengths may require the use of multiple excitation sources, with excitation wavelengths to achieve efficient excitation of the dyes over the emission wavelength range. Alternatively, energy transfer dyes can be utilized to enable a single laser, with a single emission wavelength, to be used for exciting all dyes of interest. This is achieved by attaching an energy transfer moiety to the dye label. This moiety is typically another fluorescent dye with an absorption wavelength that is compatible with the excitation wavelength of the light source (e.g. laser). Placement of this absorber in close proximity with an emitter allows the absorbed energy to be transferred from the absorber to the emitter, allowing for more efficient excitation of the long wavelength dyes (Ju et al., *Proc Natl Acad Sci USA* 1995, 92, 4347-51).

Dye labeled dideoxynucleuotides are available from Perkin Elmer, (Waltham, Mass.).

B. Examples

Example 5. Six-Color Separation and Detection of Nucleic Acids

The following example illustrates the separation and detection of nucleic acid fragments labeled with 6 fluorescent dyes, and demonstrates the color resolution capability of the spectrometer/multi element excitation/detection system. DNA fragments were labeled with 6-FAM, VIC, NED, PET dyes by applying fluorescently labeled primers in a multiplexed PCR amplification reaction. In this reaction, 1 ng of human genomic DNA (9947A) was amplified in a 25 µL reaction in according to the manufacturers recommended conditions (AmpFlSTR Identifiler, Applied Biosystems). 2.7 µL of the PCR product was removed and mixed with 0.3 µL of GS500-LIZ sizing standard (Applied Biosystems) and 0.3 µL of HD400-ROX sizing standard. HiDi (Applied Biosystems) was added to a total of 13 µL and the sample was inserted into the sample well of the separation biochip and subjected to electrophoresis.

Electrophoretic separation of DNA using Genebench consists of a series of four operations: pre-electrophoresis, loading, injection and separation. These operations are carried out on a microfluidic biochip, which is heated to a uniform temperature of 50° C. The biochip contains 16 channel systems for separation and detection multiple, each consisting of an injector channel and a separation channel. DNA for analysis is separated by electrophoretic transport of the DNA through a sieving matrix along the separation channel. The separation length of the biochips is ranges from 160 to 180 mm.

The first step is pre-electrophoresis, which is accomplished by applying a 160 V/cm field along the length of the channel for six (6) minutes. Separation buffer (TTE1X) is pipetted into the anode, cathode and waste wells. Samples for analysis are pipetted into the sample wells and a 175 V applied from the sample well to the waste well for 18 seconds, followed by the application of 175 V across the sample and waste well and 390 V at the cathode for 72 seconds, to load the sample into the separation channel. Injection of the sample is accomplished by applying a 160 V/cm field along the length of the separation channel while fields of 50 V/cm and 40 V/cm are applied across the sample and waste wells respectively. Separation is continued with the injection voltage parameters for 30 min during that an optical system detects the separating bands of DNA. The data collection rate is 5 Hz and PMT gains are set to −800 V.

Figure 17:
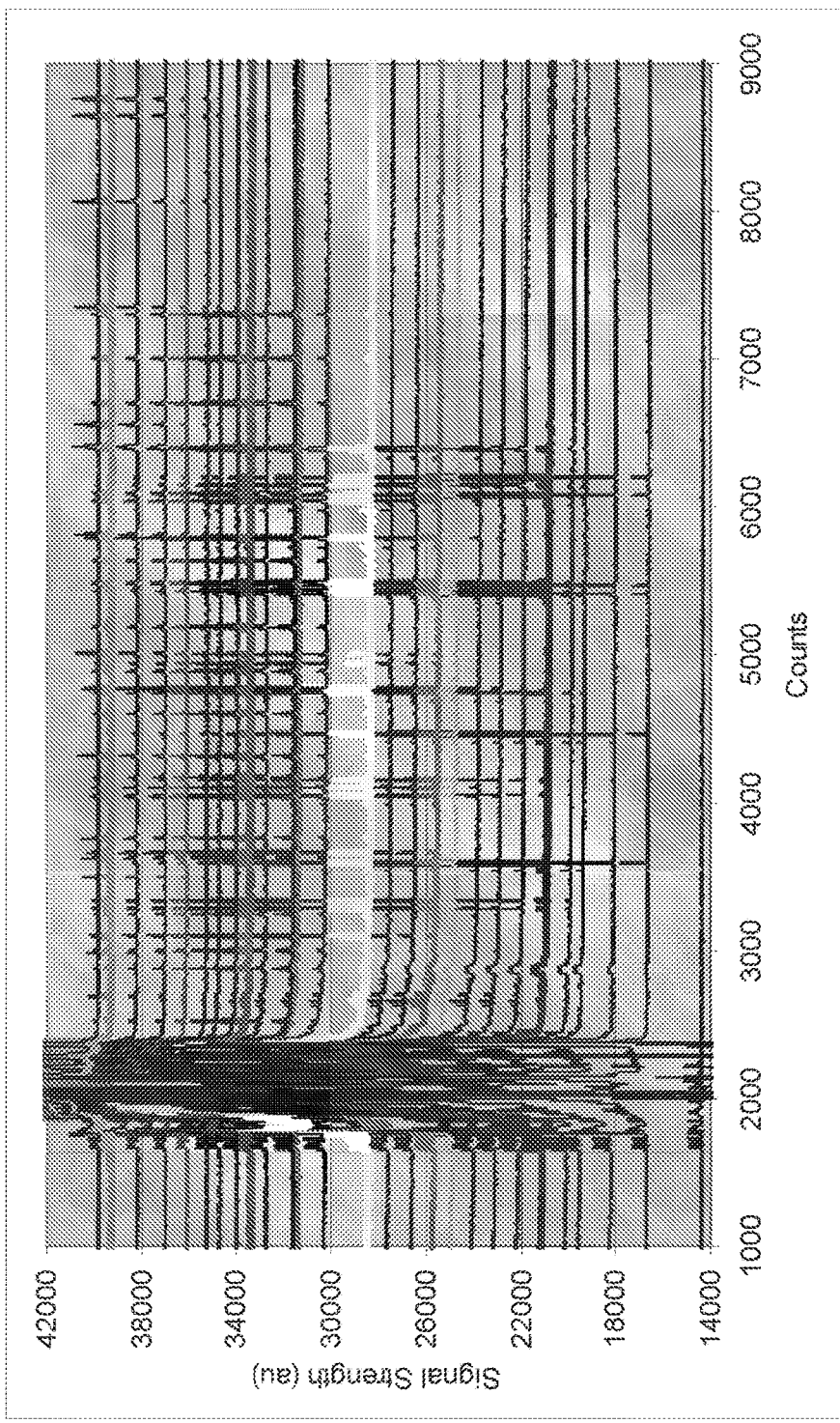
FIG. 17 is an electrophoregram generated for separation and detection of a 6 dye sample. Each trace in the graph represents the signal from each of the each of the 32 elements of a 32-anode PMT. Each trace is offset relative to each other to allow easy viewing of data.
Figure 18:
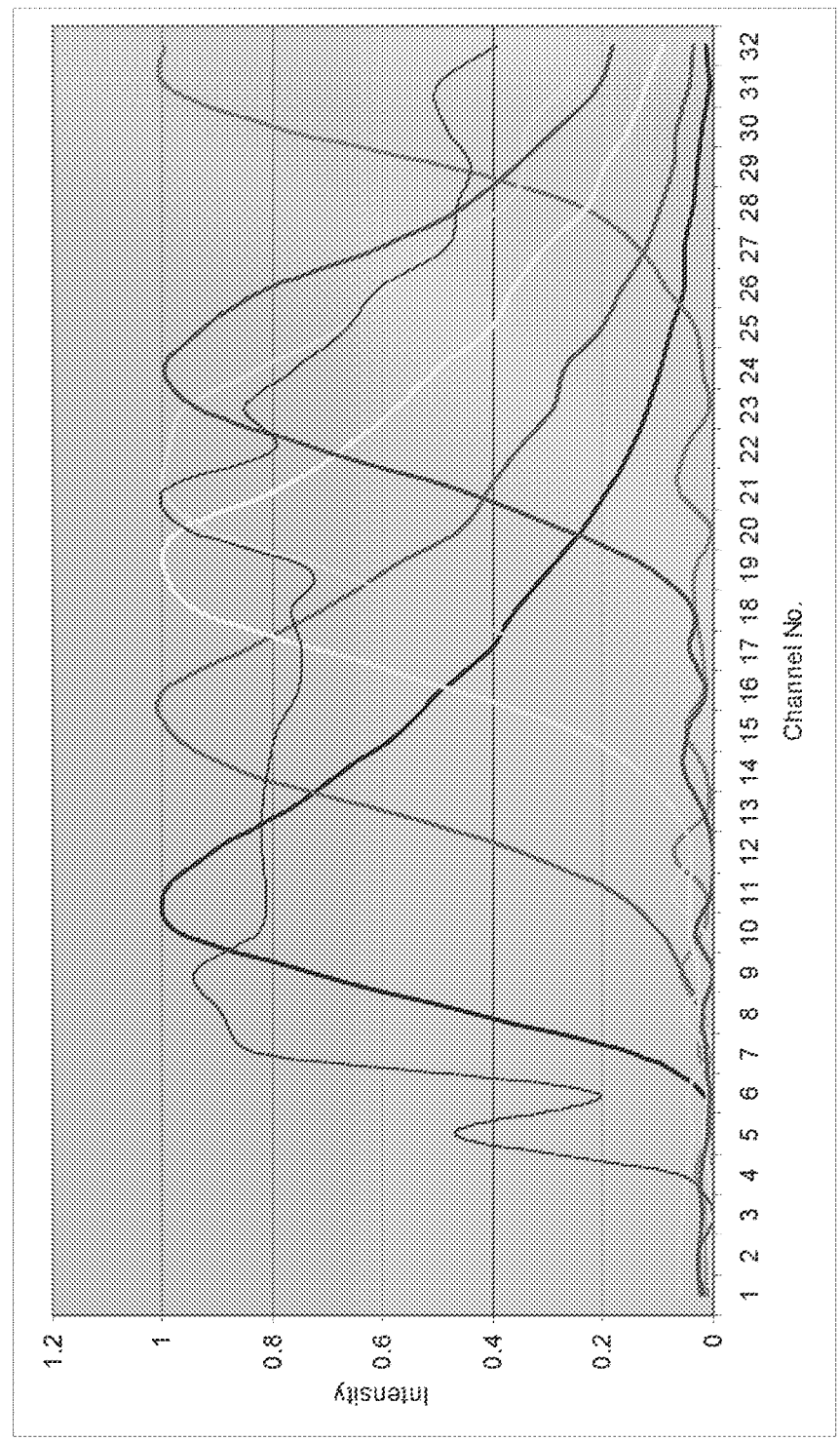
FIG. 18 is a graph showing the dye spectra of each of the 6 dyes, extracted from the electrophoregram; also shown is the background fluorescence spectra.
Figure 19:
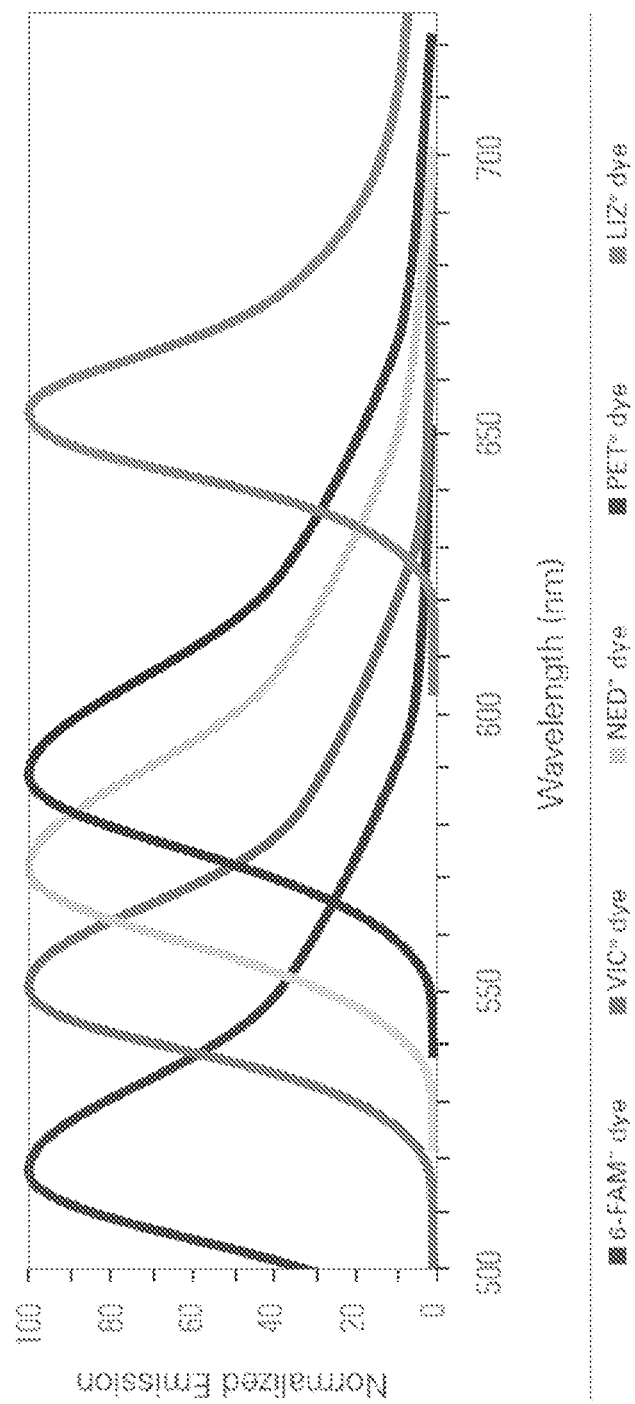
FIG. 19 is a graph showing the dye emission spectra for 6-FAM, VIC, NED, PET and LIZ dyes.
Figure 20:
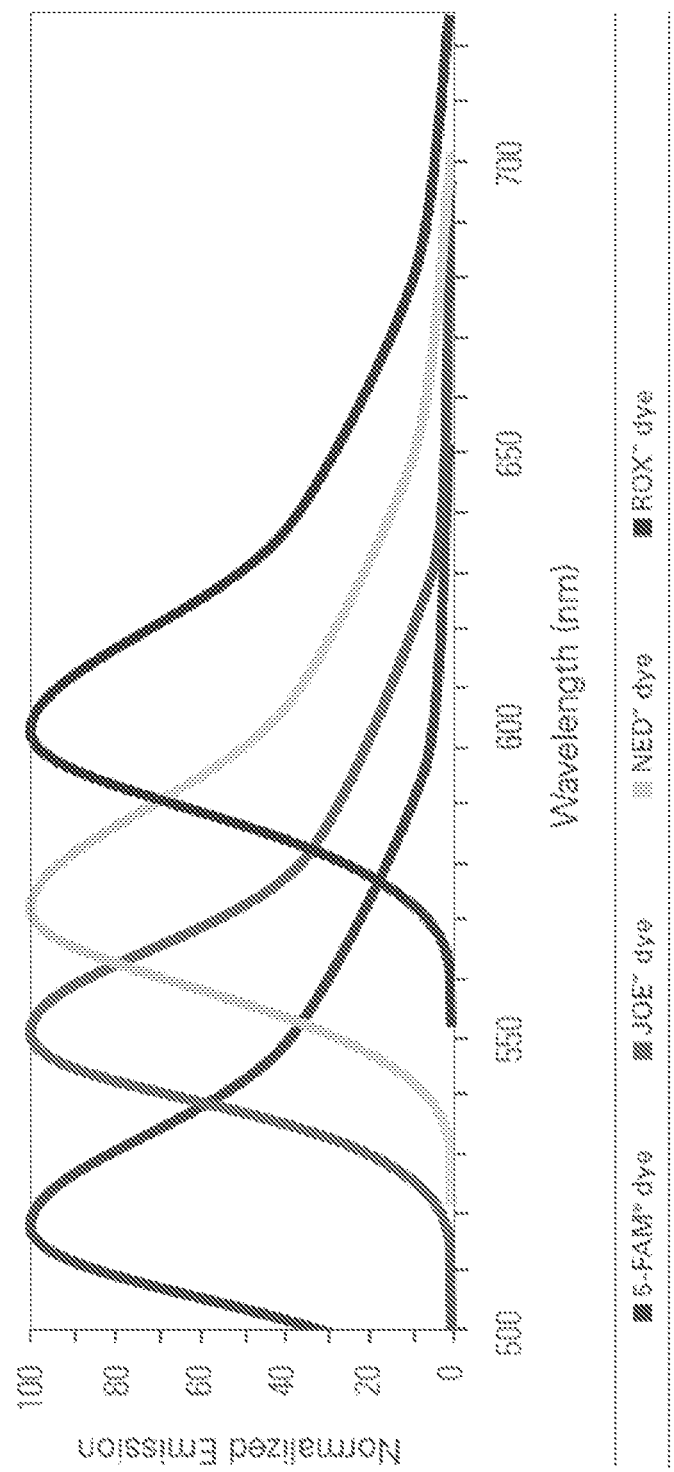
FIG. 20 is a graph showing the dye emission spectra for 5-FAM, JOE, NED, and ROX dyes.

Sixteen samples containing amplified DNA were loaded for simultaneous separation and detection. The signals from each of the 32-elements of the PMT were collected as a function of time to generate an electrophoregram. The resulting electrophoregram (FIG. 17) shows peaks corresponding to the presence of a DNA fragment at the excitation/detection window for one of the 16 lanes. Furthermore, the relative signal strength of each element of the 32-element PMT for each peak corresponds to the spectral content of the dye (or dyes if more than one dye is present at the detection window) associated with the DNA fragment. FIG. 18 shows the emission spectra of the dyes detected, and the background spectra of the substrate. The substrate background spectra is subtracted from the spectra from each of the peaks. Performing this exercise results in the identification of 6 distinct dye spectra. The spectra of the 6-dyes are superimposed on the same plot. A comparison of this data with the actual published dye spectra shows that the relative of the dyes are similar to the published data. This example demonstrates that the system is able to detect and differentiate the 6 dyes in the reaction solution. The spectral output of this is used to generate the color correction matrix and convert the signals from detector space to dye space representation (FIGS. 19 and 20).

Example 6. Eight Color Separation and Detection of Nucleic Acids

In this example, an 8 dye separation and detection of acids labeled with fluorescent dyes is shown. Forward and reverse primer pair sequences for 8 loci are selected from the published sequences (Butler et al., *J Forensic Sci* 2003, 48, 1054-64).

The loci selected are CSF1P0, FGA, THO1, TPOX, vWA, D3S1358, D5S818 and D7S820, although any of the loci and hence primer pairs described in the paper can also be used in this example. Each of the forward primers for the primer pairs is labeled with a separate fluorescent dye (Operon Biotechnologies, Huntsville, Ala.). Dyes selected for attachment to the primers include Alexa Fluor Dyes 488, 430, 555, 568, 594, 633, 647, and Tamra. Numerous other dyes are available and can also be used as labels. Each locus is amplified separately following the PCR reaction protocols of (Butler, 2003, Id.) to yield a reaction solution with fragments labeled with their respective dyes. Template for PCR reaction is 1 ng of human genomic DNA (type 9947A from Promega, Madison Wis.).

Each PCR reaction was purified by cleaning up through a PCR cleanup column, where primers (labeled and dye-labeled primers) and enzymes are removed, and the PCR buffer is exchanged by the DI eluant. The resulting product of clean is a solution of labeled DNA fragments in DI water. Cleanup of dye labeled products follows the protocol of Smith using MinElute™ columns (Qiagen, Valencia, Calif.). A total of eight reactions are performed. Eight cleaned up PCR reactions were mixed together in a ratio to generate peaks of equivalent signal strengths, generating a mixture containing fragments labeled with 8 different dyes. Alternatively, primers for 8 loci can be mixed together to form a master primer mix for multiplexed amplification.

This solution is separated and detected with the instrument and protocol as described in Example 1. The grating of the spectrograph is adjusted such that the emission of the 8 dyes falls across the 32 pixels of the detector elements. The amount of sample loaded for analysis is to be adjusted such that detected signals fall within the dynamic range of the detection system.

Example 7. Spectrometer/Multi-Element PMT System

Figure 21:
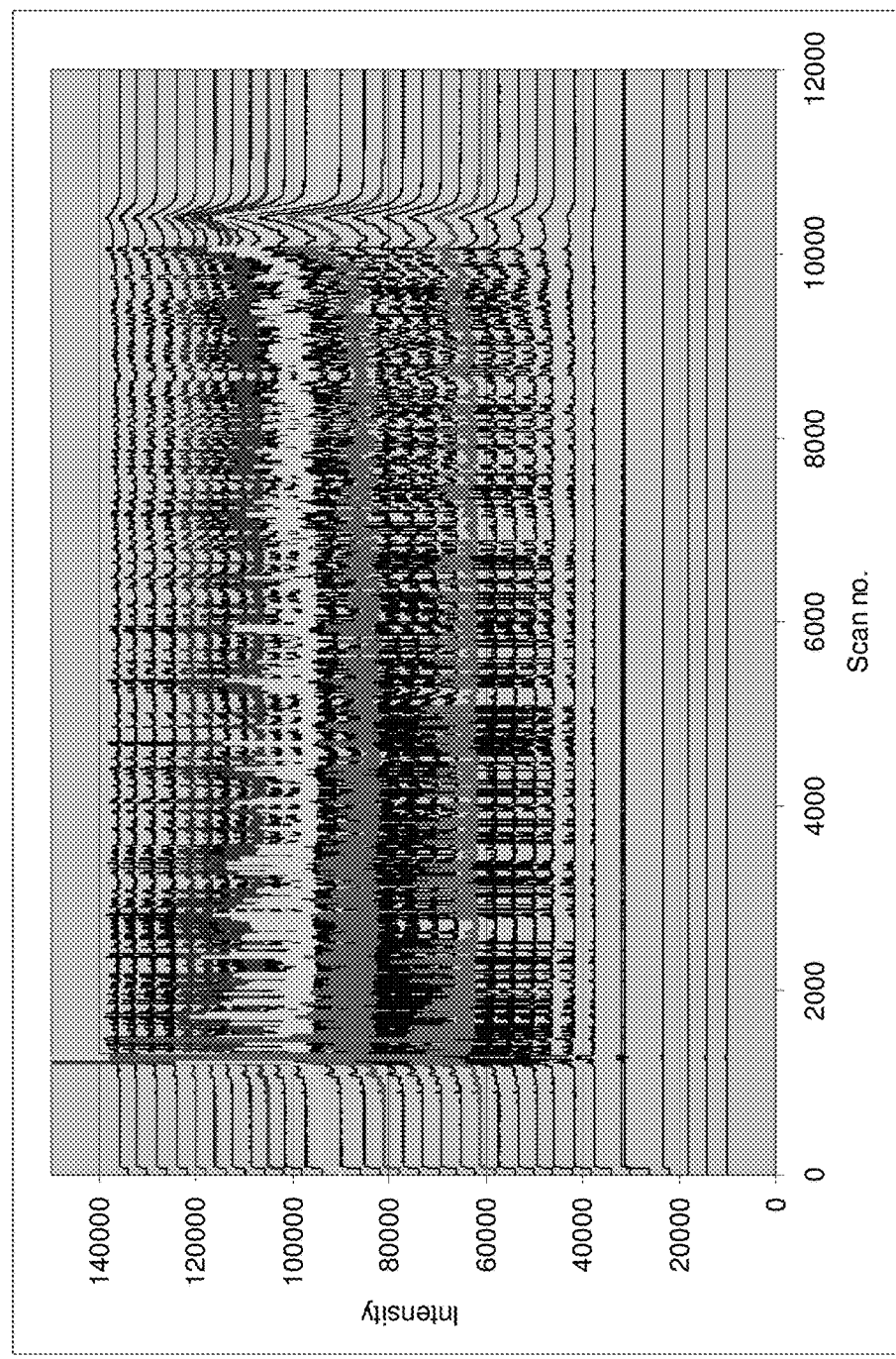
FIG. 21 is an electrophoregram generated for separation and detection of a 4 dye sample. Each trace in the graph represents the signal from each of the each of the 32 elements of a 32-anode PMT. Each trace is offset relative to each other to allow easy viewing of data.
Figure 22:
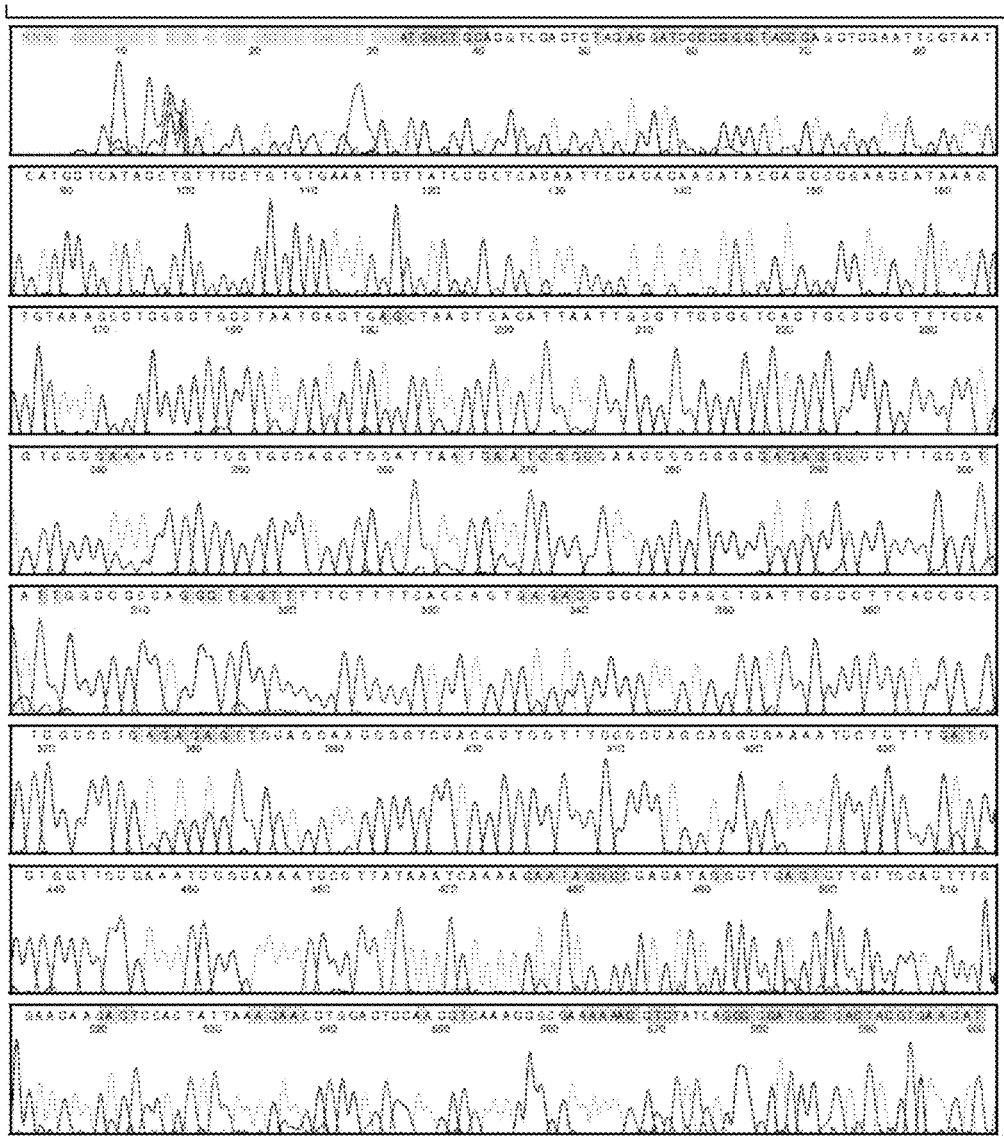
FIG. 22 is a sequencing trace.

The following example illustrates separation/detection of labeled DNA fragments with the spectrometer/multi-element PMT system of FIG. 16, specifically for identifying sequence of a DNA template. In this reaction, 0.1 pmol of DNA template M13 and M13 sequencing primer was amplified with the GE Amersham BigDye™ sequencing kit, according to the recommended reaction conditions. The reaction mix was cleaned up by ethanol precipitation and resuspended in 13 µL of DI water. The sample was separated following the electrophoretic separation condition as described in example 5. Sample loading conditions were modified and was carried out by applying 175 V across the sample well to the waste well for 105 seconds. FIG. 21 shows an electrophoregram for the DNA sequence, with colored traces representing the detector element corresponding to the spectral maximum for each of the 4 dyes used. The sequence obtained was base called with Phred quality score of >20 for 519 bases and QV30 of 435 bases (FIG. 22).

Example 8. Simultaneous Separation and Detection of Products of Two Sequencing Reactions In this example, separation and detection of fragments from cycle sequencing of two DNA templates are carried out simultaneously in a single separation channel. The cycle sequencing reactions can be prepared by either dye labeled terminator reactions or dye labeled primer reactions as follows:

For Dye Labeled Terminator Reactions:

Cycle sequencing reaction for each template fragment consisting of a sequencing primer appropriate for the template sequence of interest, and reagents for conducting DNA sequencing including cycle sequencing buffer, polymerase, oligonucleotides, dideoxynucleotides and labeled dideoxynucleotides is prepared. Eight different dyes are utilized for the labeling. In the first cycle sequencing reaction, one set of 4 dye labeled dideoxy nucleotides is used. In the second cycle sequencing reaction, another set of 4 dye labeled dideoxy nucleotides (with emission wavelengths different than those of the four used in the first cycle sequencing reaction) is used. Each cycle sequencing reaction is carried out separately following a protocol that thermally cycles each reaction multiple times. Each thermal cycle includes a denature, anneal and extension step with temperatures and times following the protocols of Sanger (see, Sanger et al., *Proc Natl Acad Sci USA* 1977, 74, 5463-7). The cycle sequencing product from the two reactions are combined to form a sample that consist of labeled DNA fragments, with a total of eight unique dyes, from each of the two DNA templates.

For Dye Labeled Primer Reactions:

Alternatively, the sample for separation and detection can be fabricated by using primer labeled cycle sequencing. Four cycle sequencing reactions are carried out for each DNA template. Each reaction is a cycle sequencing reaction consisting of a labeled sequencing primer, and reagents for conducting DNA sequencing including cycle sequencing buffer, polymerase, oligonucleotides. In addition, each reaction will include one of the dideoxynucleuotides (ddATP, ddTTP, ddCTP, or ddGTP) and one labeled primer. Each dye associated with the primer is unique in emission wavelength and is correlated with the type of dideoxy nucleotide in the cycle sequencing solution (ddATP, ddTTP, ddCTP, or ddGTP). Each cycle sequencing reaction is carried out separately following a protocol that thermally cycles each reaction multiple times. Each thermal cycle includes a denature, anneal and extension step with temperatures and times following the protocols of Sanger (see, Sanger, 1977, Id.). For cycle sequencing the second DNA template, another set of 4 dyes (with emission wavelength different to that of the four used in the first cycle sequencing reaction) is applied. The product of all eight reactions (each with a different dye) are mixed together to form a sample that consist of DNA fragments from each of the two DNA templates.

Sample for Separation and Detection:

Each of the sequencing reactions is cleaned up by ethanol precipitation. Separation and detection of the sample follows the protocol of Example 8. The result of the separation and detection is the generation of two distinct DNA sequences, corresponding to each of the two template DNA fragments.

The methods of this example can be modified to allow the use of dyes in multiples of four to allow detection of that multiple of DNA sequences in a single separation channel (e.g. 12 dyes for the detection of 3 sequences simultaneously, 16 dyes for the detection of 4 sequences simultaneously, 20 dyes for the detection of five sequences simultaneously, and so on). Finally, separation of the labeled fragments need not be limited to electrophoresis.

Example 9

Separation and Detection of 500 or More Loci in a Single Channel

There are several applications of nucleic acid analysis that can be applied to clinical diagnostics, including DNA and RNA sequencing and fragment size determination. In this example, the use of simultaneous detection of 10 colors allows the interrogation of up to 500 loci. Analysis of the size of large number of fragments can be utilized to identify pathogens or to characterize many loci within an individual's genome, for example. In the setting of prenatal and pre-implantation genetic diagnosis, aneuploidy is currently diagnosed by karyotyping and by fluorescent in situ hybridization (FISH). In FISH studies, the presence of two signals per cell indicates that two copies of a given locus are present within that cell, one signal indicates monosomy or partial monosomy, and three signals indicates trisomy or partial trisomy. FISH typically utilizes approximately 10 probes to assess whether or not a cell contains a normal chromosomal complement. This approach does not allow a detailed view of the entire genome, however, and cells that appear normal by FISH may well have major abnormalities that are not detected by the technique.

The teachings of the present invention make use of multicolor separation and detection to allow approximately 500 chromosomal loci widely dispersed about across all chromosomes to be assessed to allow a much more detailed analysis of chromosomal structure. In this example, primer pair sequences for approximately 500 loci are selected from published sequences, with each locus present as a single copy per haploid genome. In addition, 10 sets of 50 primer pairs are selected such that each set defines a corresponding set of DNA fragments such that none of the fragments are of the identical size. For each set, the forward primers for the primer pairs are labeled with one fluorescent dye, and no two sets share the same dye. Dyes selected for attachment to the primers are Alexa Fluor Dyes 488, 430, 555, 568, 594, 633, 647, 680, 700, and Tamra. Numerous other dyes are available and can also be used as labels. The loci can be amplified in one or several parallel PCR reactions as described in "METHODS FOR RAPID MULTIPLEXED AMPLIFICATION OF TARGET NUCLEIC ACIDS", supra. The amplified primers are separated and detected using the methods described herein. In a single separation channel, all 500 fragments can be precisely identified by size, 50 for each of ten dyes.

The number of loci, dyes, and separation channels can be varied based on the desired application. Smaller numbers of fragments can be detected if desired by utilizing a smaller number of dye labels or generating fewer DNA fragments per label; in this way, less than 500, less than 400, less than 300, less than 200, less than 100, less than 75, less than 50, less than 40, less than 30, or less than 20 fragments can be detected as desired. The maximum number of loci that can be identified per lane is based on the read length and resolution of the separation system (e.g., single base pair resolution of DNA fragments ranging from 20 to 1500 base pairs results in hundreds of fragments) multiplied by the number of distinct dyes that can be detected (as noted supra, dozens are available). Accordingly, thousands of loci can be identified in a single separation channel, and the number will increase as additional dyes are developed.

We claim:

1. An optical detector comprising;
one or more light sources positioned for illuminating one or a plurality of detection positions on a substrate, said substrate comprising a thermal cycling chamber adapted for multiplexed amplification in one PCR reaction, such that primers labeled with 6 or more fluorescent dyes each having a unique peak emission wavelength are used to generate amplified nucleic acid fragments labeled with said 6 or more fluorescent dyes, said thermal cycling chamber in fluid communication with at least one channel on said substrate, wherein each channel comprises a detection position;
a mirror to scan said one or more light sources sequentially between detection positions;
one or a plurality of first optical elements positioned for collecting and directing light emanating from the detection positions on the substrate; and
a light detector positioned to accept light directed from the one or plurality of first optical elements, wherein the light detector comprises a wavelength dispersive element to disperse the light from the one or plurality of first optical elements according to light wavelength into at least 6 wavelength components and, the wavelength dispersive element is positioned to provide at least a portion of the dispersed at least 6 wavelength components to at least 6 detection elements, wherein each of the detection elements are in communication with a first control element for simultaneously collecting detection information from each of the detection elements and, wherein said light detector detects fluorescence from at least 6 dyes labeled to one or more biological molecules, each dye having a unique peak emission wavelength.

2. The optical detector of claim 1, wherein the biological molecules are nucleic acids.

3. The optical detector of claim 2 wherein the nucleic acid is DNA.

4. The optical detector of claim 3, wherein said light detector detects fluorescence from at least 8 different dyes, each dyes being members of at least two 4-dye containing subsets, such that the subsets are capable of distinguishing at least two DNA sequences at a single detection position on the substrate, wherein the number of dyes is a multiple of four, and the number of DNA sequences to be detected is equal to that multiple, such that each of the different dyes is present in only one subset.

5. The optical detector of claim 1, wherein the biological molecules are proteins.

6. The optical detector of claim 1, wherein the biological molecules are nucleic acid fragments.

7. The optical detector of claim 1, wherein said at least one light source is a laser.

8. The optical detector of claim 1, wherein each detection element is capable of detecting ultraviolet light, visible light, infrared light, or a combination thereof.

9. The optical detector of claim 1, further comprising a two dimensional optical detector element, said element comprising at least two rows for the detection of optical spectra, wherein a first row detects the optical spectra of a first independent lane and said second row detects the optical spectra of a second independent lane.

10. The optical detector of claim 1, wherein each of said at least 6 detection elements is a single-anode photomultiplier tube and the wavelength dispersive element is composed of one or a plurality of dichroic mirrors positioned to provide at least a portion of the dispersed at least 6 wavelength components from said one or a plurality of first optical elements to each of said at least 6 detection elements, wherein each dichroic mirror reflects an independently predetermined wavelength of light.

11. The optical detector of claim 10, further comprising a bandpass filter wherein each independently predetermined wavelength of light essentially corresponds to a fluorescence emission maximum of a fluorescent dye present in at least one of the detection positions.

12. The optical detector of claim 10, wherein the wavelength dispersive element is a prism, diffraction grating, transmission grating, spectrograph or holographic diffraction grating.

13. The optical detector of claim 1 wherein each of the said at least 6 detection elements is a linear multi-anode photomultiplier tube.

* * * * *

SEQUENCE LISTING

```
<160> NUMBER OF SEQ ID NOS: 2

<210> SEQ ID NO 1
<211> LENGTH: 517
<212> TYPE: DNA
<213> ORGANISM: Artificial Sequence
<220> FEATURE:
<223> OTHER INFORMATION: Synthetic

<400> SEQUENCE: 1
atagaatact caagcttgca tgcctgcagg tcgactctag aggatccccg ggtaccgagc      60
tcgaattcgc cctatagtga gtcgtattac aattcactgg ccgtcgtttt acaacgtcgt     120
gactgggaaa accctggcgt tacccaactt aatcgccttg cagcacatcc ccctttcgcc    180
agctggcgta atagcgaaga ggcccgcacc gatcgccct tcccaacagt tgcgcagcct     240
gaatggcgaa tggacgcgcc ctgtagcggc gcattaagcg cggcgggtgt cggtggttac    300
gcgcagcgtg accgctacac ttgccagcgc cctagcgccc gctcctttcg ctttcttccc    360
```

```
ttcctttctc gccacgttcg ccggctttcc ccgtcaagct ctaaatcggg ggctcccttB    420
gggttccgat ttagtgcttt acggcacctc gacccaaaaa acttgattag ggtgatggtt    480
cacgtagtgg gccatcgtct gatagacggg ttttcgc                            517
```

<210> SEQ ID NO 2
<211> LENGTH: 600
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (482)..(482)
<223> OTHER INFORMATION: n is a, c, g, or t

<400> SEQUENCE: 2

```
nnncggcgcc gttccaaggc agtgcaagtt acatgnctgc aggtcgactc tagaggatcc     60
ccgggtaccg agctcgaatt cgtaatcatg gtcatagctg tttcctgtgt gaaattgtta    120
tccgctcaca attccacaca acatacgagc cggaagcata aagtgtaaag cctggggtgc    180
ctaatgagtg agctaactca cattaattgc gttgcgctca ctgcccgctt tccagtcggg    240
aaacctgtcg tgccagctgc attaatgaat cggccaacgc gcggggagag gcggtttgcg    300
tattgggcgc cagggtggtt tttcttttca ccagtgagac gggcaacagc tgattgccct    360
tcaccgcctg gccctgagag agttgcagca agcggtccac gctggtttgc cccagcaggc    420
gaaaatcctg tttgatggtg gttccgaaat cggcaaaatc ccttataaat caaaagaata    480
gnccgagata gggttgagtg ttgttccagt ttggaacaag agtccactat taaagaacgt    540
ggactccaac gtcaaagggc gaaaaaacgt ctatcagggc gatggccact acgtgaacat    600
```